(12) United States Patent
Cornelius et al.

(10) Patent No.: US 9,808,375 B2
(45) Date of Patent: *Nov. 7, 2017

(54) POWER-SAVING METHOD FOR DEFOGGING AN EYE-SHIELD

(71) Applicant: Abominable Labs, LLC, Lake Oswego, OR (US)

(72) Inventors: Jack C. Cornelius, Lake Oswego, OR (US); Vincent O'Malley, Portland, OR (US)

(73) Assignee: Abominable Labs, LLC, Lake Oswego, OR (US)

(*) Notice: Subject to any disclaimer, the term of this patent is extended or adjusted under 35 U.S.C. 154(b) by 734 days.

This patent is subject to a terminal disclaimer.

(21) Appl. No.: 14/479,247

(22) Filed: Sep. 5, 2014

(65) Prior Publication Data
US 2014/0374402 A1 Dec. 25, 2014

Related U.S. Application Data

(63) Continuation-in-part of application No. 14/046,969, filed on Oct. 6, 2013, now Pat. No. 9,419,520, which
(Continued)

(51) Int. Cl.
| | |
|---|---|
| F41H 1/04 | (2006.01) |
| A61F 9/02 | (2006.01) |
| A42B 3/22 | (2006.01) |
| G02C 11/08 | (2006.01) |
| G02B 27/00 | (2006.01) |
| A42B 3/24 | (2006.01) |

(Continued)

(52) U.S. Cl.
CPC .............. *A61F 9/028* (2013.01); *A42B 3/228* (2013.01); *G02B 27/0006* (2013.01);
(Continued)

(58) Field of Classification Search
CPC .. A41F 9/04; A42B 3/228; G02C 7/16; G02C 11/08; H05B 2203/036; G02B 7/1815
See application file for complete search history.

(56) References Cited

U.S. PATENT DOCUMENTS

| | | | |
|---|---|---|---|
| 4,209,234 A | 6/1980 | McCooeye | |
| 4,584,721 A | 4/1986 | Yamamoto | |

(Continued)

FOREIGN PATENT DOCUMENTS

| | | |
|---|---|---|
| JP | 2001221984 A | 8/2001 |
| KR | 1020050115027 A | 12/2005 |
| WO | 2013096449 A1 | 6/2013 |

*Primary Examiner* — Tejash Patel
(74) *Attorney, Agent, or Firm* — Howard Russell

(57) ABSTRACT

Power saving method providing a burst of power for defogging an eye-shield apparatus with a thin-film heater, comprising: activating the heater from an off power level to an on-demand mode or from a preliminary intermediate power level during an active-on mode to a max power level and continuing heating for a predetermined first period of time, automatically reducing power after the first period of time and sustaining the lesser power for a second predetermined period of time, after which program control automatically turns off the heater, or automatically reduces the heat back to the preliminary intermediate power level depending upon the initial state of the heater upon activating the burst of power, whether on or off. The method may be repeated as often as necessary from off level in the on-demand mode, or from within a continuous active-on mode.

20 Claims, 25 Drawing Sheets

Related U.S. Application Data is a continuation-in-part of application No. 13/397,691, filed on Feb. 16, 2012, now Pat. No. 8,566,962.

(51) Int. Cl.
 B63C 11/12 (2006.01)
 B63C 11/28 (2006.01)

(52) U.S. Cl.
 CPC .............. *G02C 11/08* (2013.01); *A42B 3/245* (2013.01); *A61F 9/022* (2013.01); *B63C 11/12* (2013.01); *B63C 11/28* (2013.01)

(56) References Cited

U.S. PATENT DOCUMENTS

| | | | |
|---|---|---|---|
| 4,868,929 A | 9/1989 | Curcio | |
| 4,942,629 A | 7/1990 | Stadlmann | |
| 5,105,067 A | 4/1992 | Brekkestran et al. | |
| 5,351,339 A | 10/1994 | Reuber et al. | |
| 5,778,689 A | 7/1998 | Beatenbough | |
| 6,470,696 B1 | 10/2002 | Palfy et al. | |
| 6,704,944 B2 | 3/2004 | Kawainshi et al. | |
| 6,896,366 B2 | 5/2005 | Rice et al. | |
| 6,927,368 B2 | 8/2005 | Cao et al. | |
| 7,387,022 B1 | 6/2008 | Korniyenko et al. | |
| 7,648,234 B2 | 1/2010 | Welchel et al. | |
| 8,566,962 B2 * | 10/2013 | Cornelius | A42B 3/245 2/15 |
| 9,419,520 B2 * | 8/2016 | O'Malley | H02M 3/1563 |
| 2003/0091089 A1 | 5/2003 | Krausse | |
| 2004/0050072 A1 | 3/2004 | Palfy et al. | |
| 2004/0050076 A1 | 3/2004 | Palfy et al. | |
| 2006/0289458 A1 | 12/2006 | Kim et al. | |
| 2008/0290081 A1 | 11/2008 | Biddell | |

\* cited by examiner

1500

| Watts | 2.0 | 4.0 | 6.0 | 8.0 | 10.0 |
|---|---|---|---|---|---|
| Voltage | | | Duty Cycle | | |
| 8.4 | 11.3 | 22.7 | 34.0 | 45.4 | 56.7 |
| 8.3 | 11.6 | 23.2 | 34.8 | 46.5 | 58.1 |
| 8.2 | 11.9 | 23.8 | 35.7 | 47.6 | 59.5 |
| 8.1 | 12.2 | 24.4 | 36.6 | 48.8 | 61.0 |
| 8.0 | 12.5 | 25.0 | 37.5 | 50.0 | 62.5 |
| 7.9 | 12.8 | 25.6 | 38.5 | 51.3 | 64.1 |
| 7.8 | 13.1 | 26.3 | 39.4 | 52.6 | 65.7 |
| 7.7 | 13.5 | 27.0 | 40.5 | 54.0 | 67.5 |
| 7.6 | 13.9 | 27.7 | 41.6 | 55.4 | 69.3 |
| 7.5 | 14.2 | 28.4 | 42.7 | 56.9 | 71.1 |
| 7.4 | 14.6 | 29.2 | 43.8 | 58.4 | 73.0 |
| 7.3 | 15.0 | 30.0 | 45.0 | 60.0 | 75.1 |
| 7.2 | 15.4 | 30.9 | 46.3 | 61.7 | 77.2 |
| 7.1 | 15.9 | 31.7 | 47.6 | 63.5 | 79.3 |
| 7.0 | 16.3 | 32.7 | 49.0 | 65.3 | 81.6 |
| 6.9 | 16.8 | 33.6 | 50.4 | 67.2 | 84.0 |
| 6.8 | 17.3 | 34.6 | 51.9 | 69.2 | 86.5 |

| Watts Voltage | 1.5 | 3.0 | 4.5 Duty Cycle | 6.0 | 7.5 |
|---|---|---|---|---|---|
| 8.4 | 8.5 | 17.0 | 25.5 | 34.0 | 42.5 |
| 8.3 | 8.7 | 17.4 | 26.1 | 34.8 | 43.5 |
| 8.2 | 8.9 | 17.8 | 26.8 | 35.7 | 44.6 |
| 8.1 | 9.1 | 18.3 | 27.4 | 36.6 | 45.7 |
| 8.0 | 9.4 | 18.8 | 28.1 | 37.5 | 46.9 |
| 7.9 | 9.6 | 19.2 | 28.8 | 38.5 | 48.1 |
| 7.8 | 9.9 | 19.7 | 29.6 | 39.4 | 49.3 |
| 7.7 | 10.1 | 20.2 | 30.4 | 40.5 | 50.6 |
| 7.6 | 10.4 | 20.8 | 31.2 | 41.6 | 51.9 |
| 7.5 | 10.7 | 21.3 | 32.0 | 42.7 | 53.3 |
| 7.4 | 11.0 | 21.9 | 32.9 | 43.8 | 54.8 |
| 7.3 | 11.3 | 22.5 | 33.8 | 45.0 | 56.3 |
| 7.2 | 11.6 | 23.1 | 34.7 | 46.3 | 57.9 |
| 7.1 | 11.9 | 23.8 | 35.7 | 47.6 | 59.5 |
| 7.0 | 12.2 | 24.5 | 36.7 | 49.0 | 61.2 |
| 6.9 | 12.6 | 25.2 | 37.8 | 50.4 | 63.0 |
| 6.8 | 13.0 | 26.0 | 38.9 | 51.9 | 64.9 |

Fig. 17

POWER-SAVING METHOD FOR DEFOGGING AN EYE-SHIELD

CROSS-REFERENCE TO AND INCORPORATION BY REFERENCE OF RELATED APPLICATIONS

This application is a continuation-in-part of prior co-pending U.S. patent application Ser. No. 14/046,969, filed 6 Oct. 2013, for Battery Compensation System Using PWM (hereafter also referred to as "the Parent Application"), which is a continuation-in-part of U.S. patent application Ser. No. 13/397,691, filed 18 Feb. 2012, for PWM Heating System for Eye-shield (U.S. Pat. No. 8,566,962, issued 29 Oct. 2013) (hereafter also referred to as "the PWM Patent" or "the PWM Application"). This application claims the benefit of the priority date of the Parent Application. The Parent Application and the PWM Application are hereby incorporated by reference in this application.

FIELD OF INVENTION

This invention relates generally to a method for regulating power from a battery to a heating member on an eye-shield to prevent fogging, and more particularly to a method for regulating power from a battery to an eye-shield to prevent fogging, to conserve battery life, increase efficiency and promote consistent heating levels despite battery depletion over time.

BACKGROUND OF THE INVENTION

It is often desirable to use goggles or a protective eye-shield for protecting one's vision when engaged in any number of activities or occupations such as outdoor winter sports, skiing, hiking, sledding, tubing, mountaineering, ice climbing, snowboarding, snowmobiling, paintballing, swimming, scuba diving, snorkeling, skydiving, hazardous activities requiring safety eye protection, industrial use, target shooting, police work, tactical operations, riot control, corrections or military use. Additionally, it is also often necessary to use goggles or eye-shields in environmental conditions which contribute to condensation build-up on the eye-shield, causing fogging and vision impairment. In this and similar environments, where the temperature of an eye-shield has dropped below a dew-point temperature, fogging can occur, obscuring the vision of a user, and possibly contributing to a hazardous environment.

A common characteristic of portable eye-shield devices is the fact that they are light weight enough to be carried on a user's body, e.g., worn on a user's head. Examples of fog-prone sport goggles intended for use during winter activities, have included goggles for downhill skiing, cross-country skiing, snowboarding, snowmobiling, sledding, tubing, mountaineering, ice climbing and the like, and are widely known and widely utilized by sports enthusiasts and others whose duties or activities require them to be outside in snowy and other inclement cold weather conditions. Examples of fog-prone dive masks have included eye and nose masks independent of a breathing apparatus as well as full-face masks in which the breathing apparatus is integrated into the mask. Examples of fog-prone eye-protecting shields have included a face shield that a doctor or dentist would wear to prevent pathogens from getting into the user's mouth or eyes, or a transparent face shield portion of a motorcycle helmet. Fogging that impairs vision is a common problem with such goggles, dive masks and eye-protecting shields.

Anti-fog sport goggles, dive masks and other highly portable transparent anti-fog eye-protecting shields use batteries not only to power these devices but also to heat the devices to prevent fogging of an eye-shield or viewing screen. Lithium-Ion batteries have been used in the powering of such heated eye-shields. A known issue with these Lithium-Ion batteries is the fact that, as their charge decreases over time in use, the voltage output they provide also decreases over time in use. Thus, with conventional lithium-ion battery-powered devices, there has developed a need to regulate power applied as the battery has become depleted over time to provide consistent heating to the eye-shield to prevent fogging.

There have been various conductive apparatus devised for preventing condensation build-up on eye-shields. The purpose of these conductive apparatus has been to provide an eye-shield and viewing screen that may be maintained free of condensation so that the user would be able to enjoy unobstructed vision and viewing during various activities. Prior sports goggles have been primarily used in environments requiring a high degree of portability, that is, where a power source for powering the electronics for the device has been advantageously carried on a strap for the goggle itself as shown and described in co-pending U.S. Patent Application Ser. No. 61/563,738, by McCulloch, for Modular Anti-fog Goggle System. As a result, such systems have needed to be light weight.

While such battery-powered eye-shields, especially heating devices which consume extraordinary amounts of power from batteries, need to be judicious in the use of total power source, generally measured in amp-hours, to preserve power source life, it has also become important that the power circuitry of such systems provide even power, or customized power, distribution across an eye-shield, as well as a consistent level of power to the eye-shield. Thus, the ability to adjust the amount of current delivered to the eye-shield's resistive element, compensated for decreasing voltage as the battery charge is depleted, had also become desirable.

Responsive to these concerns there has been provided U.S. Pat. No. 8,566,962, for PWM Heating System for Eye-shield, to Cornelius (the "PWM Patent"), in part to allow application of different on-cycle PWM levels to an eye-shield, for example depending upon the heating requirements of different portions of the eye-shield, and also to enable even and consistent heating, or alternatively custom heating in accordance with a profile, over the entire eye-shield.

The PWM Patent has proven useful to allow a user to adjust power consumption, to enable even distribution of power across a divided eye-shield and to maximize battery life in an eye-shield, but the limitation of Lithium-Ion battery depletion and correspondent voltage depletion had nevertheless remained a problem. Thus, it was recognized that, where there is sufficiently available battery power to perform heating operations on an eye-shield device, an appropriate amount of additionally available power would have been useful to make power supplied to the device more consistent throughout the depletion cycle of the battery.

Accordingly, another problem with powered eye-shields to prevent fogging has been that, as available power to heat the eye-shield has decreased as the battery has worn down, a chosen power setting has been less effective to produce consistent heating of the eye-shield. Thus, in the Battery Compensation System Using PWM patent application Ser.

No. 14/046,969, to O'Malley and Cornelius, (the "Parent Application") a system has been provided for monitoring voltage output from the battery over time, together with compensation in the PWM circuit, to increase the percentage on-time of the system in order to increase power supplied to the heater to provide consistent heating of the eye-shield over time despite partial depletion of the battery.

As the battery to an eye-shield has become depleted over a cycle of use, especially with lithium-ion-type batteries, the power generated has decreased, and this has led to inconsistent application of power to heat the eye-shield over the cycle of use. These problems have resulted in limited usefulness of heating of goggle eye-shields. Because of the irregular shape of eye-shields, these problems have existed whether one is considering resistive wire applications or resistive-film applications.

No prior art goggle has made use of their battery supplies to provide evenly distributed and consistent power to the device despite depletion of battery charge. There have been no known methods or systems disclosed in the prior art for balanced, even heating of a resistive element on an eye-shield, while compensating to provide consistent power to the eye-shield, despite partial battery depletion and to enable effective and efficient defogging of the eye-shield over an extended period of time. U.S. Pat. No. 4,868,929, to Curcio, for Electrically Heated Ski Goggles, comprises an eye-shield with embedded resistive wires operatively connected via a switching device to an external power source pack adapted to produce heating of the eye-shield for anti-fog purposes. U.S. Pat. No. 7,648,234, to Welchel et al., for Eyewear With Heating Elements, discloses use of nichrome and thin film heating elements used for heating an eye-shield and discloses use of a control mechanism for turning on and off the heat to the eye-shield. Neither discusses the foregoing power regulation, power conservation and power distribution concepts for an eye-shield. Neither discusses the use of PWM circuitry to provide even, or custom, power distribution, consistent and efficiently-regulated power to an eye-shield, despite charge depletion.

Manual switching the power on to an eye-shield when a user has experienced fogging conditions, and then later manually switching it off when the user has suspected the fogging has dissipated and heat has been no longer required, as would have been required in the prior art to maximize battery life and still seek fog dissipation, has not been, and would not be, an efficient way to consistently and efficiently overcome fog and condensation. This method has not been efficient for prior art eye-shields in part because while the eye-shield has used full power while it has been turned on, hot spots have been created in the irregularly-shaped lens eye-shield, and this has led to attempts to adjust for the hot spots and a consequential inefficient use of battery resources. Additionally, it has been difficult to gauge power requirements for a fog-proof eye-shield, since users haven't been able to gauge the relative humidity and temperature within their goggle enclosures, and since existing fog has taken more power to dissipate, while maintaining an existing fog-free lens in a fog-free state has required a lesser application of power. Accordingly, users haven't known precisely when to turn off power to the heater, so at best, the user has had to guess when was an appropriate time to turn off the power. This, in turn has led to fogging if the device has been turned off too early, or on the other hand, has led to hot spots and wasted power usage if the device has been left on too long. When a user has been involved and concentrating on an activity at hand, it often has not been convenient to have to turn on, or to turn off, the power to heat the eye-shield.

Further, users have forgotten, indeed may even be prone to have forgotten, to turn off the power to their goggle devices, thus unduly and quickly depleting valuable power resources. Thus, manual switching on and off of devices as needed to prevent condensation has not allowed for precise fog dissipation, has not enabled a judicious use of power, nor has it allowed for intermediate power usage which would have been useful to sufficiently curtail fogging while still conserving battery life.

Thus, there has been discovered a need to provide a power-saving method for defogging a goggle, or eye-shield, which provides adequate power to meet the requirements of defogging the eye-shield under varying conditions, and which also maintains the eye-shield free of condensation, while striving in an overall method and system to conserve battery life. Similarly, there has been discovered a further need for a method to control an anti-fogging device on an eye-shield that would provide enough power to dissipate fog and condensation quickly, that would curtail future fogging and that would provide even, consistent heating despite battery depletion over time in use, and yet still strive to conserve battery life by providing for a judicious use of readily available, light weight, power resources.

SUMMARY OF THE INVENTION

In accordance with an aspect of the invention, there has been provided an eye-shield condensation preventing system comprising: an eye-shield adapted for protecting a user's eyes and adapted for defining at least a partially enclosed space between the user's eyes and the eye-shield, a power source, a pulse-width modulator (PWM), a switching means responsive to the pulse-width modulator, a heating element on the eye-shield, and a circuit interconnecting the power source, the pulse-width modulator, the switching means and the heating element for controlling heating of the eye-shield. Preferably, the switching means comprises a metal-oxide-semiconductor field-effect transistor.

The device of this aspect of the invention provides a single-PWM, single heating region eye-shield fog prevention device that enables efficient heating of the eye-shield or lens so that battery life is maximized, since PWM can be preset to an output having a percentage ratio of on to off cycles that is tailored specifically to the particular goggle lens to which power is being applied.

In accordance with another aspect of the invention, there has been provided an eye-shield condensation preventing system comprising: an irregular-shaped eye-shield comprising a surface area divisible into a plurality of regions of one or more sizes to facilitate divisible heating of the eye-shield, the eye-shield being adapted for protecting a user's eyes and adapted for defining at least a partially enclosed space between the user's eyes and the shield. The system further comprises a power source, a plurality of PWMs, each PWM operatively connected with the power source and a plurality of switching means, each switching means responsive to a corresponding PWM. With this aspect of the invention, there are a plurality of heating elements on the eye-shield, each the heating element extending to a corresponding size region of the eye-shield, and a plurality of circuits, each circuit interconnecting one of the PWMs with a corresponding one of the switching means and one of the corresponding heating elements. Each the PWM produces a duty cycle for providing an amount of current to the corresponding heating element such that the power output of each region of the eye-shield corresponds to a desired output for the region of the eye-shield.

In accordance with the aspects of the invention described above, there has been provided an eye-shield condensation preventing system comprising: an eye-shield adapted for protecting a user's eyes and adapted for defining at least a partially enclosed space between the user's eyes and the eye-shield, the eye-shield having a surface area divisible into at least one region for facilitating region heating of the eye-shield to a desired temperature, a power source, at least one PWM, at least one heating element on and corresponding with the at least one region for facilitating region heating of the eye-shield, the at least one heating element corresponding with the at least one PWM. In this embodiment, there is at least one circuit interconnecting the power source, the at least one PWM and the at least one corresponding heating element for heating the eye-shield, wherein the at least one PWM controls current to maintain the temperature of the at least one heating element region to a temperature above the anticipated dew point of an operating environment.

The device of the multiple-region aspect of the invention provides a multiple-PWM resistive film heating system on the eye-shield or lens surface that is divided into multiple regions, for example regions according to irregular and differently-shaped portions of the lens such as directly over the bridge of the nose as compared to directly in front of the eyes, to enable even heating of differently-shaped or sized regions. Thus, for example, the regions may be used to divide the lens into a plurality of regions, each of similar area from one region to the next, to enable more even heating across the eye-shield. Or, conversely this division may be used to allow specific heating of a certain area of the eye-shield, for example to ensure proper function of an electronic display portion of the lens.

In accordance with another aspect of the invention building on the multiple-region aspect of the invention, the PWMs may be operated in accordance with a profile such that the power per square unit, i.e., power density, of each region of the eye-shield may be assured to be substantially equal and evenly distributed across the region regardless of the size of each region. Or, alternatively, heating of the regions may be independently adjusted to create a specific profile desired for a particular eye-shield to account for various pre-determined weather conditions, various activities or eye-shield types, shapes and sizes.

Preferably, the plurality of PWMs of this aspect of the invention comprises a microcomputer capable of simultaneously performing a plurality of various internal PWM functions corresponding to the plurality of PWMs, the microcomputer having a plurality of I/O ports for interconnecting the internal PWM functions with the plurality of circuits. Further, preferably, each of the switching means in accordance with this aspect of the invention comprises a metal-oxide-semiconductor field-effect transistor (MOSFET).

In accordance with another aspect of the invention, whether involving the single-region, single-PWM device, or whether involving the multiple-region, multiple-PWM device, there has been provided an eye-shield condensation preventing system as previously summarized which further comprises a current adjustment means (CAM) operatively connected to each PWM (whether a single-PWM embodiment or a multiple PWM embodiment) for varying duty cycle of the power source via each PWM in turn varying the amount of current delivered to each heating element.

The device of this aspect of the invention provides the ability of the CAM for efficient managing of the temperature of the eye-shield lens at a temperature that is just above the dew point temperature to effectively prevent fogging with a minimum of attention by the user. This, in turn, allows power savings to enable longer battery life.

In accordance with another aspect of the invention, there has been provided an eye-shield condensation preventing system as previously described, whether a multiple-region, multiple-PWM embodiment, or a single-region, single-PWM embodiment, the device further comprising means for measuring ambient temperature and relative humidity and means for calculating dew point. The means for calculating dew point in this aspect of the invention is preferably operatively connected with the CAM (preferably further comprising microcomputer means) such that the CAM increases power to the electrical circuit when temperature within the space by the eye-shield falls below the dew point temperature threshold and reduces power to the electrical circuit when temperature within the space defined by the eye-shield climbs above the dew point temperature threshold. Thus the invention is capable of feeding a pulse to the resistive heating element, e.g., the film heating element, that is just enough to keep it at just above the dew point to effectively and automatically prevent fogging and to conserve battery life. The means for calculating dew point preferably comprises microcomputer means operatively connected with the temperature and relative humidity sensing means.

The eye-shield condensation preventing system of this aspect of the invention may further comprise a relative humidity sensor and a temperature sensor, each sensor located within the space defined by the eye-shield. Such a system further comprises means, for example microcomputer means, operatively connected with the relative humidity and temperature sensor for periodically calculating dew point temperature. Further, the at least one pulse-width modulator is responsive to the means for periodically calculating dew point temperature to control the at least one heating element such that the at least one heating element is maintained at a temperature at above dew point to assure prevention of fogging over time.

In accordance with another aspect of the invention, the eye-shield condensation preventing system of the previous two aspects of the invention, as pertaining to multiple-region embodiments of the invention, may further comprise region profiling logic enabling a single adjustment from the variable current adjustment mechanism to affect proportional adjustments to each region relative to other regions. Thus, the invention provides varying coordinated duty cycles to power multiple resistive regions of an eye-shield for the purpose of distributing heating evenly throughout the entire eye-shield by adjusting the power delivered to each segment based on a profile of the eye-shield. Further, the device of this aspect of the invention provides automated profile characteristics incorporated into the fog prevention system such that desired heating of the lens, whether it be even heating across multiple regions across the entire lens, or a pre-determined specific heating pattern, or heating footprint using different regions of the lens, may be maintained upon manual, or automated, adjustment of the heating power directed to the lens.

In accordance with yet another aspect of the invention, there has been provided an eye-shield condensation preventing system as described above in the single-region or the multiple-region aspects of the invention as described above, and further in accordance with the previous aspect of the invention comprising a plurality of predetermined data profiles and corresponding selection means enabling control of each region of the eye-shield in accordance with a user-selected one of the data profiles.

The device of this aspect of the invention provides selectable profile characteristics incorporated into the eye-shield fog preventing system such that appropriate heating may be selected by the user depending upon weather and activity level conditions, or eye-shield features employed, such as video recording, heads-up display, global positioning system, etc.

Each of the eye-shields disclosed herein are adapted for protecting a user's eyes from wind, debris, snow, rain, extreme temperatures and elements which could harm the eyes or otherwise impair vision. Each eye-shield is also adapted to form and define at least a partial enclosure around and in front of the eyes. This enclosure warms up relative to conditions outside of the enclosure as a result of body heat transmitted into the space defined by the eye-shield, and the enclosure also experiences higher relative humidity compared to outside conditions as a result of perspiration. When the temperature of the eye-shield drops below the temperature within the eye-shield at which dew, or condensation, would form on the inside of the eye-shield, fogging of the eye-shield occurs.

One purpose of the invention hereof is to provide an eye-shield fog prevention system that effectively prevents the eye-shield from fogging, regardless of weather conditions. Another purpose of the invention hereof is to provide an eye-shield fog prevention system that employs PWM in such a way that power and energy are conserved and battery life is extended. Another purpose of the invention is to provide an eye-shield fog prevention system that adjusts the power to the heater on the lens in accordance with current dew point conditions, either manually, or automatically, increases power to the eye-shield as temperature within the eye-shield is less than or falls below the dew point temperature, or so decreases power when temperature within the eye-shield is above the dew point temperature. Another purpose of the invention hereof is to provide an eye-shield fog preventing system that assures and simplifies the attainment of fog-free usage in varying weather and activity conditions, with a plurality of different sized and shaped eye-shields, by providing profiles that at least partially automate heating of the eye-shield. Yet another purpose of the invention hereof is to provide such profiles that are user selectable. Another purpose of the invention hereof is to provide means for compensating for reduced power from a battery as it depletes over time to provide consistent power to a device. Still another purpose of the invention hereof is to provide a method and system allowing convenient, quick and efficient defogging of an eye-shield, as well as maintaining the eye-shield fog free, all while conserving battery life. Another purpose of the invention hereof is to provide a means for preventing undue discharge of a portable power source of an eye-shield, whether by preventing application of excess power for requirements, or by preventing failure in turning off power due to forgetting, or otherwise being unaware, of a reduced need for power. The foregoing listing is not intended as an exclusive listing of purposes of the invention, there may be other purposes for which the invention may be suited which are not listed, and the presence or absence of any such purpose herein shall not necessarily limit the spirit and scopes of the invention as further defined and claimed herein.

The eye-shield condensation preventing system of the invention hereof may be adapted for use for heating in an anti-fog sport goggle or any protective eye-shield, such as for skiing, inner-tubing, tobogganing, ice-climbing, snowmobile riding, cycling, running, working with patients, in other medical or testing environments, and the like. Further, the system of any of the foregoing aspects of the invention may be adapted for use in a diving mask.

In accordance with another aspect of the invention, there has been provided a compensation system adapted for use with any of the foregoing battery-powered, PWM-driven eye-shields, to enable consistent power to the device load despite battery voltage drop resulting from battery depletion. The compensation system in accordance with this aspect of the invention comprises: a voltage divider circuit for proportionally adjusting the voltage to a measurable range; an analog to digital converter for receiving the output from the voltage divider and converting it into a digital voltage value; and means for receiving digital voltage input and user-determined power setting input for determining a compensating duty cycle for application to the PWM to drive the load consistently at the user-determined power setting despite decrease in battery voltage resulting from battery depletion. Preferably, the voltage divider circuit of an embodiment in accordance with this aspect of the invention comprises two precision resistors in series between positive and negative terminals of the battery for proportionally adjusting the voltage to a measurable range, the voltage divider circuit preferably having a tap between the two resistors adapted to provide the proportional voltage measurement to an I/O pin on an analog-to-digital converter. Preferably, the user-determined, or provided, power setting for this and another aspect of the invention comprises a power level setting set by a dial, a knob, or a push button system, together with some form of visual feedback to the user to further enable selection of the setting.

In accordance with an embodiment of the invention, there has been provided mode switching means for user selection of battery conservation mode or consistent power output mode. The battery conservation mode provides an off switch for the compensation system, whereas the consistent power mode provides an on switch for the compensation system. Though the battery conservation mode uses less battery power than the consistent power mode, for those times where there is sufficient battery power to use the consistent power mode, it may be preferable to a user to do so, since a user-determined power level in this latter mode would yield results consistent with what a user would expect with an otherwise fully-charged battery. The selection of battery conservation mode or consistent power mode depends upon the total battery charge available, the longevity of a particular battery as experienced by the user, and the anticipated level of heating required for a number of use hours anticipated by the user.

In accordance with an embodiment of the invention, the battery compensation system is adapted for use with at least one lithium-ion battery-powered, PWM-driven anti-fog eye-shield, such as for example a ski goggle, a diving mask, a motorcycle or snowmobile helmet visor, a tactical or military goggle, or a medical or testing visor.

In accordance with an embodiment of the invention, the compensation system of the invention further comprises a metal-oxide-semiconductor field-effect transistor switching means responsive to the pulse-width modulator. Further, in accordance with an embodiment of the invention, the compensation system of the invention further comprises current adjustment means operatively connected to the pulse-width modulator for varying duty cycle of the power source via the pulse-width modulator in turn varying the mount of current delivered to the load.

In accordance with an embodiment of the Parent Application invention, the means for receiving voltage input and user-determined power setting input for determining compensating duty cycle comprises a microprocessing unit for receiving voltage input and user-determined power setting input and executing software code to determine a compensating duty cycle for application by the software to the PWM to drive the load consistently at the user-determined power setting despite decrease in battery voltage resulting from battery depletion. For this embodiment of the invention, the microprocessing unit is preferably a battery-powered microprocessing unit. It will be appreciated by those of ordinary skill in the art that readily-available microprocessing units having on-board analog-to-digital conversion means may be used for the present invention.

Still further, determination of a compensating duty cycle may comprise a data lookup table of PWM duty cycle values organized according to power setting and battery depletion voltage drop and for use by the code steps run by the microprocessor to select a compensating duty cycle for application to the PWM to drive the load consistently at the user-determined power setting despite decrease in battery voltage resulting from battery depletion. This embodiment of the invention including a lookup table provides generally faster operation and is easier to code than using floating-point calculations, though it will be appreciated that either may be used to implement the invention in accordance with its true spirit and scope. Further, while conceivably a discrete logic circuit could be used to perform the functions of the compensation system of the invention, such would likely be unduly expensive to implement and no more effective than the software and data table lookup functions that are preferred for the invention.

In an alternate embodiment of the invention, the software steps themselves may be used to calculate a compensating duty cycle for application to the PWM to drive the load consistently at the user-determined power setting despite decrease in battery voltage resulting from battery depletion. The formula for determining the compensating duty cycle for this embodiment of the invention, which is the same formula used to determine data table duty cycle values (from user input power settings and measured voltage) used in a previous software embodiment is as follows:

$$\text{Duty Cycle} = \frac{\text{Desired Power} * \text{Load Resistance}}{(\text{Battery Voltage})^2} * 100$$

The compensation system in accordance with this aspect of the invention enables maintenance of a user-selected and/or desired power setting to drive a load to consistently heat the anti-fog eye-shields, despite partial depletion of a device battery, as long as there is sufficient battery charge to maintain the system-compensated power output. Thus, as the voltage from the battery drops resulting from battery depletion from use over time, the system compensates by increasing the duty cycle of the PWM driver for the device.

In accordance with another aspect of the invention, there has been provided an alternative embodiment compensation system adapted for use with a battery-powered, multi-channel PWM-driven portable electronic device having a plurality of loads corresponding to each PWM channel to enable consistent power to each of the loads of the device despite battery voltage drop resulting from battery depletion. The compensation system in accordance with this aspect of the invention comprises: a voltage divider circuit for proportionally adjusting the voltage to a measurable range; an analog to digital converter for receiving the output from the voltage divider and converting it into a digital voltage value; and a microprocessing unit for running software code steps for receiving digital voltage input and user-determined power setting input for each load for determining a compensating duty cycle for application by the software to each PWM channel to drive each corresponding load consistently at the user-determined power setting despite decrease in battery voltage resulting from battery depletion.

The compensation system in accordance with this aspect of the invention enables compensation for a depleting battery source for maintaining, with the use of a multi-channel PWM system, consistent power over time to each of a plurality of loads of a portable device (as long as there remains sufficient battery charge to power the device), such as a multi-region, anti-fog eye-shield powered by the system to evenly heat each of the regions across the eye-shield to a consistent temperature. Alternatively, such a system in accordance with this aspect of the invention may be used to provide consistent heating, despite battery depletion over time, to heat a multi-heating-element-region eye-shield to prevent fogging in each of the regions according to a custom heating profile applied to the eye-shield.

Thus, preferably the compensation system in accordance with this aspect of the invention is embodied wherein each of the plurality of loads comprises a heating element region on an eye-shield and each corresponding PWM channel is for providing the same power density to each heating element region for even heating across the entire eye-shield. This even heating embodiment of the invention further preferably comprises a data lookup table of PWM duty cycle values organized according to power setting and battery depletion voltage drop and for use by the code steps to select a compensating duty cycle for application to each PWM to drive each load consistently at the user-determined power setting despite decrease in battery voltage resulting from battery depletion.

Further, preferably, the compensation system in accordance with this aspect of the invention to provide consistent heating in accordance with a custom profile is embodied wherein each of the plurality of loads comprises a heating element region on an eye-shield and each corresponding PWM channel is for providing a power density to each heating element region in accordance with the custom heating profile across the eye-shield. This custom heating embodiment further comprises a plurality of data lookup tables of PWM duty cycle values, one data lookup table for each different power density specified by the custom heating profile, each data table being organized according to power setting and battery depletion voltage drop and for use by the code steps to select a compensating duty cycle for application to each PWM to drive each load consistently at the corresponding power setting despite decrease in battery voltage resulting from battery depletion.

Each of the aspects of the invention, whether single channel PWM-driven, or multi-channel PWM-driven, provides for consistent power to the load of a portable electronic device, despite charge/or power, depletion or dissipation of the battery over time in use. Thus, these aspects of the invention provide a consistent feedback to the user who is reinforced and supported in coming to expect that a certain power setting on the device, selected from a series of power settings such as 2 Watts, 4 Watts, 6 Watts, 8 Watts or 10 Watts, will effectively heat the eye-shield at the desired power level during anticipated weather conditions.

The compensation system of the invention, whether single-channel PWM or multi-channel PWM embodiments of the invention, further preferably comprises a data lookup table of PWM duty cycle values organized according to power setting and battery depletion voltage drop and for use by the code steps to select a compensating duty cycle for application to the PWM to drive the load consistently at the user-determined power setting despite decrease in battery voltage resulting from battery depletion.

In accordance with another aspect of the present invention, there is provided a program-automated, power-saving method and system for efficiently heating an eye-shield apparatus adapted for use with a thin-film heater powered by a power source to prevent fogging of the eye-shield comprising the microprocessor and program controlled steps of: activating the heater from an off power level to a substantially highest, substantially higher, or maximum, power level (hereafter "max power level") on the eye-shield apparatus, continuing heating at the max power level for a first duration of time, lessening power supplied to the heater after the first duration of time to an intermediate power level between the off power level and the max power level, continuing heating at the intermediate power level for a second duration of time, and turning or setting the power to the off power level after the second duration of time.

This aspect of the invention provides quick dissipation of fog and condensation from an eye-shield apparatus while still conserving power. Activating the power from an off power level to a substantially higher power level, substantially highest power level, or maximum power level (hereafter "max power level") provides a burst of power to the thin-film heater, quickly raising the temperature of the eye-shield to a level suitable for dissipating fog and condensation. Sustaining the max power level heat mode for a period of time facilitates full dissipation of the fog. After this first burst of power at the max power level, the power level is automatically lessened by program and microprocessor control to an intermediate power level. Lessening power for a second duration of time conserves total power available, and sustaining the intermediate power level for the second period of time facilitates preventing fog and condensation from reforming on the eye-shield. Using program and microprocessor control to automatically turn off the power after the second duration of time further conserves battery power and alleviates the likelihood that a user may forget to turn off power to the defogging system. This aspect of the invention may be thought of as an "on-demand" or "burst" power mode.

In accordance with one embodiment of this aspect of the present invention, the max power level comprises a maximum power level. Providing maximum power to the heater on the eye-shield accelerates heating of the eye-shield, and thus the rate at which fog and condensation dissipates.

In accordance with another embodiment of this aspect of the invention, there is provided a power-saving method and system for efficiently heating an eye-shield apparatus wherein the eye-shield apparatus further comprises a PWM system for regulating power from the power source to the heater. Preferably, the power-saving method further comprises the following steps: applying a desired pulse-width modulator duty cycle for at least one of the max power level, the intermediate power level, and the off power level. Applying a pulse-width modulator duty cycle facilitates distributing a desired amount of power to the eye-shield to create consistency of heating of the eye-shield. Another embodiment of the invention may, through use of the pulse-width modulator, provide for varying coordinated duty cycles to power multiple resistive regions of the eye-shield. This will more uniformly heat the eye-shield, preventing hot spots, and further conserve battery power.

In accordance with yet another embodiment of this aspect of the invention, there is provided an alternative automated, program-controlled power-saving method and system for efficiently heating an eye-shield apparatus, wherein the eye-shield apparatus further comprises a battery compensation system. In accordance with this embodiment of the invention, the power-saving method further comprises the steps of providing consistent power to the heater, despite battery voltage drop resulting from battery depletion through use of the battery compensation system. Using a battery compensation system to compensate for voltage drop which results from battery depletion assists in uniformly and consistently heating the eye-shield from time-to-time, over time and also over a single use cycle.

In accordance with this aspect of the invention, an embodiment of the invention is provided comprising a program controlled, automated power-saving method for efficiently heating an eye-shield apparatus, wherein the battery compensation system further comprises a voltage divider, an analog to digital converter, and a processor. The power-saving method and system of this embodiment further comprises the steps of: proportionally adjusting the voltage to a measurable range using the voltage divider, receiving an analog voltage signal from the voltage divider, converting the analog voltage output into a digital voltage signal, and determining a compensating duty cycle to apply power to the heater using the digital voltage signal.

The method and system of this aspect of the invention provides the ability to create consistency while heating the eye-shield. As power is used and the battery voltage supplied drops, the voltage level is measured and compensated for through adjusting the duty cycle of the power supplied. Adjusting the duty cycle based on the measurement of the power supplied allows for a more uniform temperature while heating the eye-shield.

In accordance with another aspect of the invention, there is provided an at-least partially automated and program-controlled power-saving method and system for efficiently continuing the heating of an eye-shield apparatus adapted for use with a powered thin-film heater to prevent fogging of an eye-shield. The power-saving method and system in accordance with this aspect of the invention comprises the program controlled steps of: activating the heater to a substantially highest, substantially higher, or maximum, power level ("max power level") from a desired preliminary intermediate power level between a power off level and a max power level on the eye-shield apparatus, continuing heating of the eye-shield heater at the max power level for a first duration of time, lessening power supplied to the eye-shield apparatus after the first duration of time to any power level intermediate between the off power level and the max power level, and continuing heating at the any power level intermediate between the off power level and the max power level until either a user turns off the eye-shield apparatus or battery power is substantially fully consumed and the eye-shield apparatus shuts off.

Alternatively, in accordance with another embodiment of this aspect of the invention, the method and system provided and enabling at least partially automated continuing power to the eye-shield after an initial substantially high power burst for a first period of time may also be implemented directly from a power off level, as for example with a longer button press by a user on a goggle. In accordance with this embodiment of this aspect of the invention, there is provided a power-saving method and system for efficiently heating an eye-shield apparatus adapted for use with a powered thin-film heater to prevent fogging of the eye-shield comprising the at-least partially program-controlled steps of: activating the heater to a substantially highest, substantially higher, or maximum power level ("max power level") from a power off level; continuing heating at the max power level for a first duration of time; lessening power supplied to the eye-shield apparatus after the first duration of time to an intermediate power level between the off power level and the max power level; continuing heating at the intermediate power level until either a user turns off the eye-shield apparatus or battery power is substantially fully consumed and the eye-shield apparatus shuts off.

This aspect of the invention provides quick dissipation of fog and condensation from an eye-shield apparatus and maintains a fog and condensation free eye-shield. Some power is continuously supplied to the heater in order to continue providing fog resistance for the entire duration of battery life, until a user chooses to turn off the device, or until the user chooses to enter the on-demand mode. Activating the power from an off power level, or a desired preliminary intermediate power level, such as with a user-supplied button press, to a max power level provides a burst of power to the thin-film heater, quickly raising the temperature of the eye-shield to a level suitable for dissipating fog and condensation. Sustaining the max power level for a period of time facilitates full dissipation of the fog. After this first burst of power at the max power level, the power level is automatically lessened to and maintained at an intermediate power level (either the desired preliminary intermediate power level, in the case of the first-mentioned embodiment of this aspect of the invention, or any other preferably pre-determined intermediate power level between the off power level and the max power level, in the case of either the first or the second above-mentioned embodiments of this aspect of the invention) in order to conserve power while still preventing fog and condensation from re-forming on the eye-shield. During the intermediate period of time, or second period of time, power is continuously supplied to the heating device for the life of the battery. This aspect of the invention may be thought of as a "constant-on" mode of operation. During the constant-on mode of operation, a user may override, as with a button press, to turn off the power to the device to conserve battery life, or the user may alternatively select the on-demand power mode.

In accordance with another aspect of the invention, an at-least partially automated, partially program-controlled power-saving method for efficiently heating an eye-shield apparatus adapted for use with a powered thin-film heater to prevent fogging of the eye-shield is provided comprising a step of: manually activating the heater, as with a button press, to a substantially highest, substantially higher, or maximum, power level (hereafter "max power level") from a desired preliminary intermediate power level between a power off level and the max power level on the eye-shield apparatus. This aspect of the invention further comprises the steps of: continuing heating at the max power level for a first duration of time; automatically lessening power supplied to the eye-shield apparatus after the first duration of time to a secondary power level intermediate between the preliminary intermediate power level and the max power level; continuing heating at the secondary power level for a second duration of time; again automatically lessening power supplied to the eye-shield apparatus after the second duration of time to substantially the preliminary intermediate power level until either a user turns off the eye-shield apparatus or battery power is substantially fully consumed and the eye-shield apparatus shuts off.

This aspect of the invention gives a user power over dissipating fogging and provides for flexibility in tailoring the power-saving bursts to given conditions to further enable customizing power usage in order to save power while providing efficient and effective defogging of a powered eye-shield. It will be appreciated, therefore, that further customization of the method and system by adding additional levels of heating for successive periods of time, as descried above, may be employed without departing from the true scope and spirit of the invention.

In accordance with yet another embodiment of either of these last two aspects of the invention, either of the previously described embodiments of the invention may be provided an at-least partially automated and program-controlled power-saving method for efficiently heating an eye-shield apparatus wherein the eye-shield apparatus further comprises a PWM system for regulating power from the power source to the heater. Additionally, the power-saving method further comprises the program-controlled steps of: applying a desired pulse-width modulator duty cycle for at least one of the max power level, the desired preliminary intermediate power level, the any power level intermediate between the off power level and the max power level, and the off power level, from a pulse-width modulator system for controlling the amount of heat applied to the eye-shield apparatus. A pulse-width modulator duty cycle facilitates in distributing a desired amount of power to the eye-shield in order to consistently heat the eye-shield. This is beneficial because by controlling the amount of power supplied, and in turn the amount of heat generated, the problem of hot spots and inconsistent heating over time can be avoided, and power savings may be achieved. Additionally, an embodiment of the invention may, through use of the pulse-width modulator, provide for varying coordinated duty cycles to power multiple resistive regions of the eye-shield. This will more uniformly heat the eye-shield to also prevent hot spots and conserve battery power.

In accordance with still another embodiment of either of these two last aspects of the invention, there is provided an at-least partially automated and program-controlled power-saving method for efficiently heating an eye-shield wherein the eye-shield apparatus further comprises a battery compensation system. The power-saving method of this embodiment of the invention may be applied to the embodiment relating to entering continuous power mode from an off power level, or alternatively from a desired preliminary intermediate power level, and further comprises the steps of providing consistent power to the heater, despite battery voltage drop resulting from battery depletion, through use of the battery compensation system. Without the system, as battery power is consumed and depleted over time to power the heater, the voltage output of the battery at a given on-cycle power setting also decreases. This causes the heat produced by the heating device to be lower, increasing the probability of fog and lending to an inconsistency in experience by a user at the given power setting. Providing consistent power to the heater despite battery voltage drop will keep the temperature of the heater constant, leading to a more desirable and predictable experience, and will reduce the probability of fogging on the eye-shield.

In accordance with either of these last two aspects of the invention, whether from an off power level or from a preliminary intermediate power level, a preferred embodiment of a power-saving method for efficiently heating an eye-shield apparatus is provided wherein the battery compensation system further comprises: a voltage divider, an analog to digital converter, and a processor such as a microprocessor. Additionally, the power-saving method of this embodiment and aspect of the invention further comprises the steps of: proportionally adjusting the voltage to a measurable range using the voltage divider, receiving an analog voltage signal from the voltage divider, converting the analog voltage output into a digital voltage signal, and determining a compensating duty cycle to apply power to the heater using the digital voltage signal.

These last two aspects of the invention provide the ability to create consistency while heating the eye-shield. Further, a user is enabled in maintaining the eye-shield fog free for an extended period of time in a constant on, versus on-demand, mode. As power is used and the battery voltage supplied drops, the voltage level is measured and compensated for through adjusting the duty cycle of the power supplied. Adjusting the duty cycle based on the measurement of the power supplied will allow for a more uniform temperature while heating the eye-shield.

BRIEF DESCRIPTION OF THE DRAWINGS

FIG. 15 is a sample data table of duty cycles to be applied by a PWM to a battery compensation system in accordance with the invention;

FIG. 17 is another sample data table of duty cycles to be applied by a PWM to a battery compensation system in accordance with the invention;

FIG. 21a is a graphical representation of an example of power supplied over time of a battery power-saving method and system in accordance with the aspect of the invention shown in FIG. 18a.

DETAILED DESCRIPTION OF THE INVENTION

Pulse-Width Modulation

Figure 1:
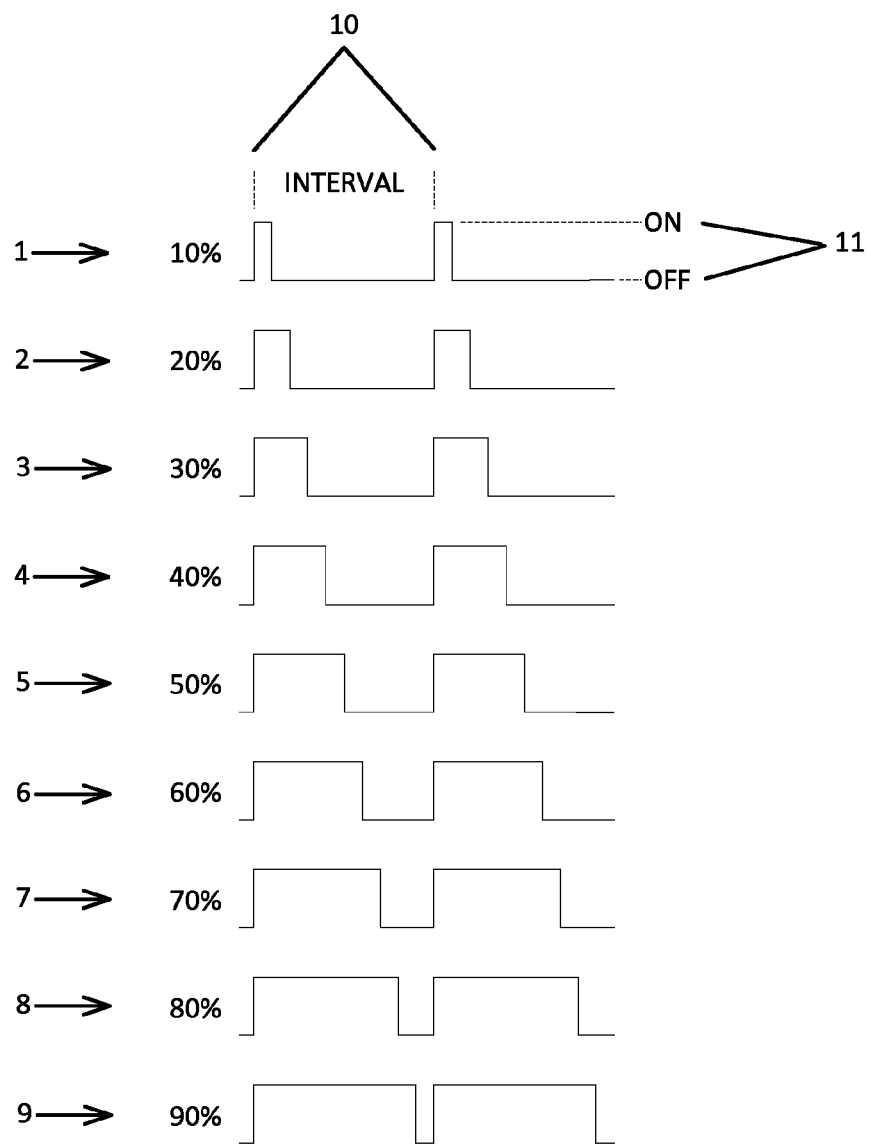
FIG. 1 is a graphic representation of a plurality of electrical signals emanating from a pulse-width modulator (PWM)

Pulse-Width Modulation (PWM) is used mostly in motor speed control applications for varying the speed of a motor. Referring to FIG. 1, PWM is characterized by either an analog or a digital signal generated by a pulse width modulator, such as an analog oscillator, or a digital logic device, which provides varying duty cycles that are a percentage on, for example such as 10%, 20%, 30%, and up to 90% or more, on, and a corresponding percentage off, such as 90%, 80%, 30%, and down to 10% or less, off, all as illustrated by numbers 1-9 on FIG. 1. Dotted lines 10 are used to point out the wavelength of the PWM signal, and dotted lines 11 are used to point out the constant voltage magnitude on (high) condition and the constant voltage magnitude off (low) condition. Thus, for example, where the PWM circuit connected to a 12-volt battery is 40% on and 60% off, one might say that the PWM signal represents a 12-volt PWM circuit at 40% power. Thus, the PWM circuit can run a motor at 40% of its maximum speed, or alternately another percentage of the motor's maximum speed, with a constant voltage source and without adjusting voltage, and this provides the effect of providing a continuous lower voltage by regulating the current delivered to the motor. PWM signals typically have a fixed frequency as is the case with those shown in FIG. 1, and they are typically of a constant full voltage at the full voltage level or a constant no voltage at the low voltage level, though this is not absolutely necessary.

Single-Region, Single-PWM Embodiment

Figure 2:
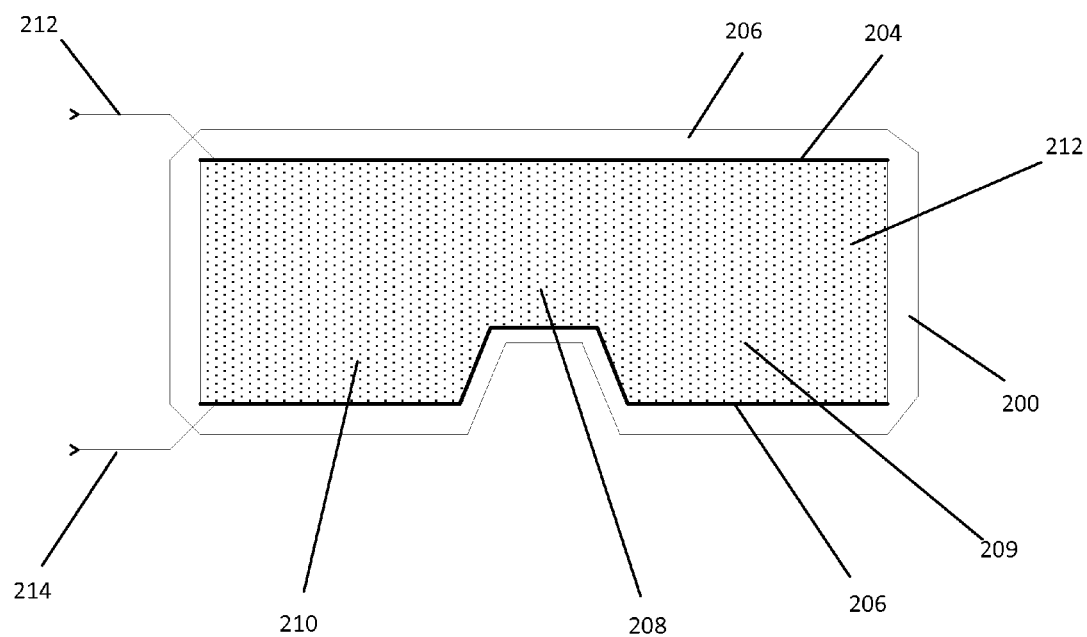
FIG. 2 is a front plan view schematic representation of an irregular-shaped eye-shield having a single-region, resistive heating element film heater thereon.

Referring to FIG. 2, there is provided in accordance with part of a first embodiment of the invention an eye-shield lens or protective eyewear 200 adapted for at least partially defining an enclosure around a user's eyes and having thereon a single-region resistive transparent conductive film heating member 202. Along an upper edge of the film heating member 202 there is a bus-bar heating element 204 interconnected with a power source (not shown) via a lead wire 212. The film heating member 202 may be comprised of indium-tin oxide (ITO) or other material designed in the form of a resistive element that generates heat when connected to an electrical circuit.

A lower buss-bar heating element 206 is provided along a lower edge of the film heating member 202 and which is interconnected with the power source via another lead wire 214. As is typical with many eye-shields, such as in the case of winter sports goggles, the eye-shield lens 200 is irregular shaped having two wider similarly shaped square, rectangular, circular or elliptical areas 209, 210, directly anterior of a user's eye during use, and a narrower area 208 above the bridge of the nose of the user during use. Because of the different shapes of the lens 200 at each of these regions, and since the area over the bridge of the nose is smaller than directly in front of the eyes, there would be a tendency for the lens to be hotter over the bridge of the nose since there would be lesser measured electrical resistance in this area.

Figure 5:
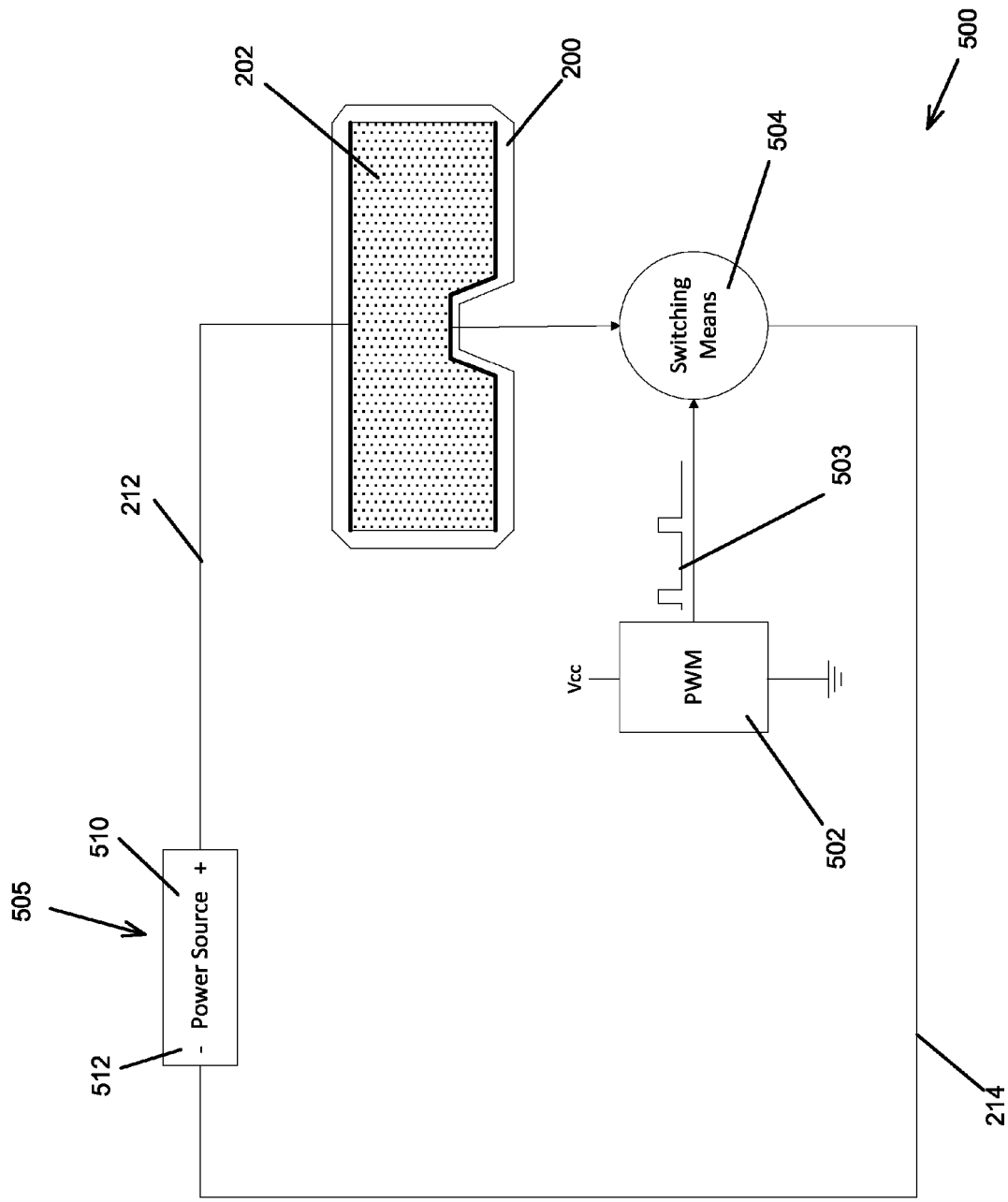
FIG. 5 is a schematic representation of a single-PWM, single-region eye-shield fog prevention system in accordance with an aspect of the invention.
Figure 6:
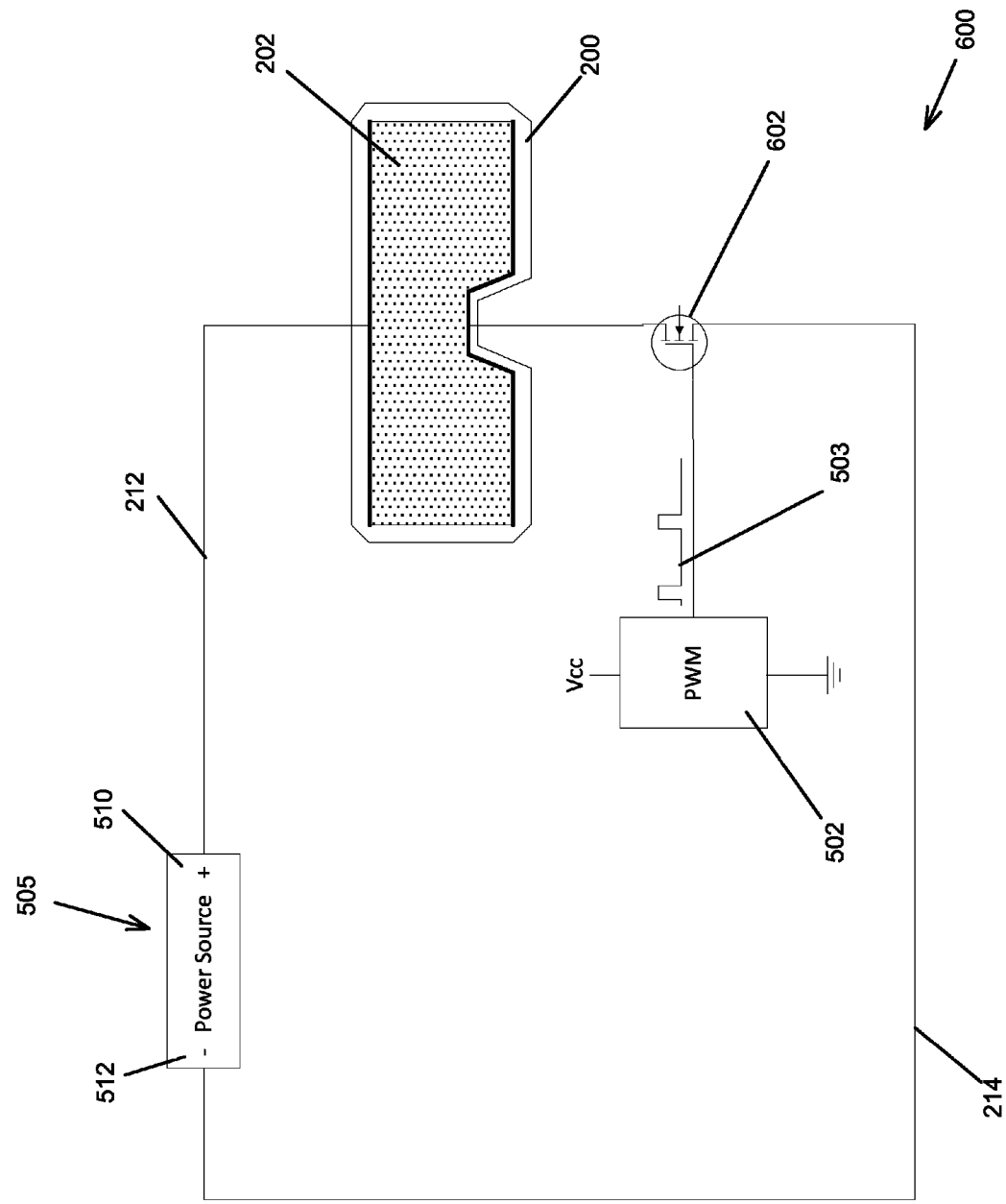
FIG. 6 is a schematic representation of a single-PWM, single-region eye-shield fog prevention system in accordance with an aspect of the invention.

As shown in FIG. 5, a first embodiment of the invention is provided as a single-PWM, single-region fog prevention system 500 in accordance with the first aspect of the invention. System 500 comprises a single PWM 502 for generating a constant ratio PWM signal 503, switching means 504, such as preferably a MOSFET switch as shown in FIG. 6, a heating element 202 deposited on a lens 200, and a power source 505 having positive and negative terminals 510, 512. The foregoing elements are interconnected in a circuit via a positive lead wire 212 and a negative lead wire 214. PWM signal 503 controls switching means 504 which controls power to the heating element 202. Since in this embodiment of the invention there is no means of varying input voltage to the PWM 502, the PWM is set to a constant ratio, on to off, that would allow for heating of a single-region heating element 202 on the lens 200 at a constant temperature. Referring to FIG. 6, a single-PWM, single-region fog prevention system 600 is shown comprising a battery power source 505 having positive and negative terminals 510, 512, circuit wires 212, 214, PWM 502 (which generates signal 503), eye-shield 200 and heating element 202 which is the same as system 500 except the generic switching means has been replaced with a MOSFET switch 602. While preferably a MOSFET switch is employed with the current invention, other switching means including relays, power transistors or other currently known switches may be used without departing from the true scope and spirit of the invention.

Current Adjustment Means (CAM)

Figure 7:
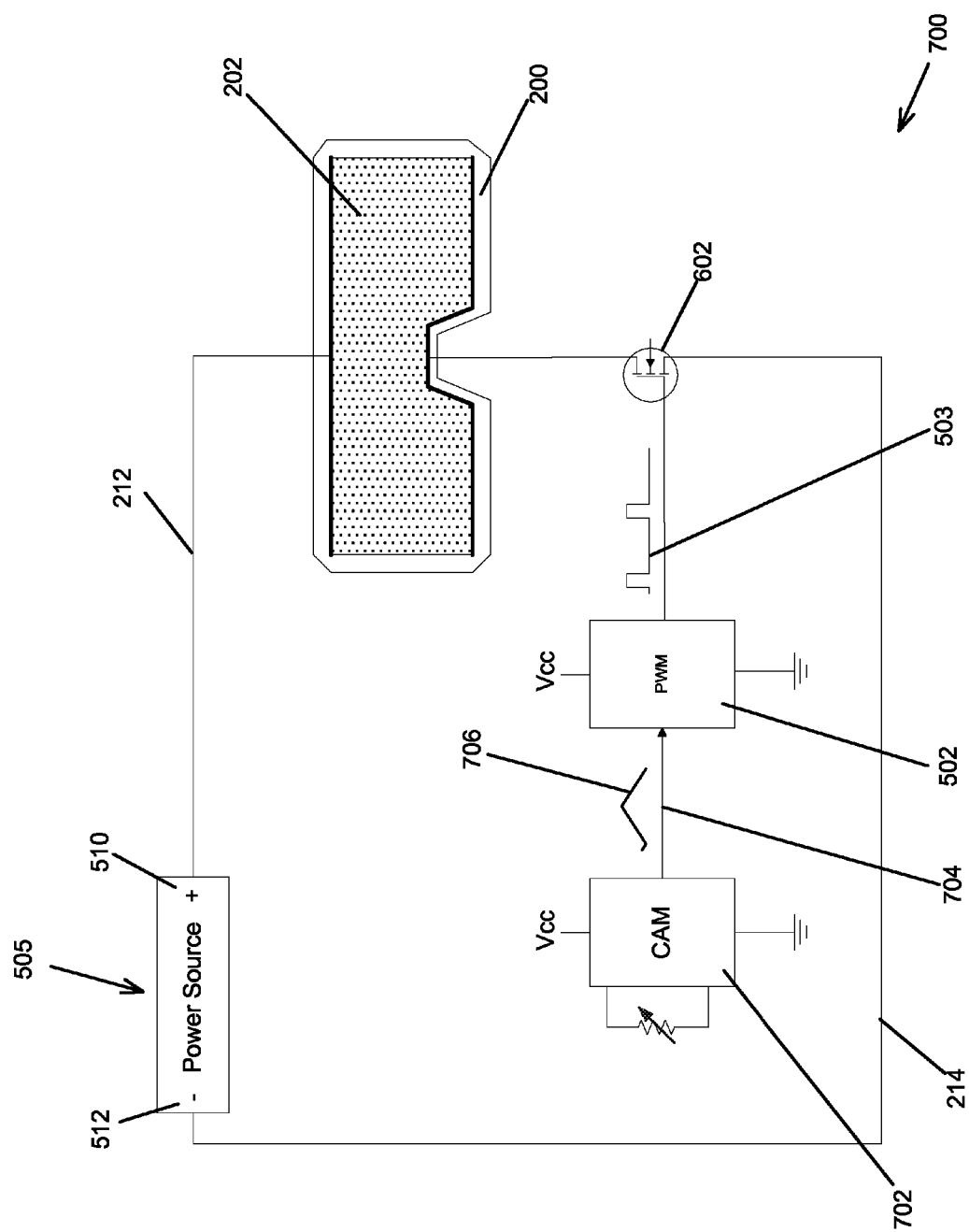
FIG. 7 is a schematic representation of another embodiment of a single-PWM, single-region eye-shield fog prevention system in accordance with an aspect of the invention.

Referring now to FIG. 7, a single-PWM, single-region fog prevention system 700 is shown comprising a battery power source 505 having positive and negative terminals 510, 512, circuit wires 212, 214, PWM 502 (which generates signal 503), MOSFET 602, eye-shield 200 and heating element 202 which system is the same as system 600 except the system 700 further comprises a current adjustment means (CAM) 702. In this embodiment of the invention, the CAM 702 is shown as a device which comprises a potentiometer and has an internal reference voltage (vref) that is lower than the battery minimum usable voltage and provides an output voltage (input voltage to the PWM), the output voltage from the CAM being some voltage between zero and the reference voltage (vref) based upon the setting of the potentiometer. Responsive to the CAM 702, the PWM 502 produces a corresponding percentage on/off signal that can be varied as a result of output from the CAM. In a preferred system using digital logic, as shown and further described below in connection with FIG. 11, a software control CAM responsive to a MORE (increase) button and responsive to a LESS (decrease) button directly varies the duty cycle of the PWM and thereby varies the amount of current delivered to the heating element 202 without requiring an intermediate voltage reference.

An output line 704 carrying the output voltage of the CAM 702 is operatively connected between the CAM and the PWM 502. The PWM 502 translates the output voltage from the CAM 702 into a signal having a duty cycle corresponding and proportional to the magnitude of the voltage into the PWM. The duty cycle of the PWM's 502 output will therefore vary in relation to the voltage in from the CAM 702 such that a near-zero input voltage from the CAM to the PWM will result in a near-zero percent on/near 100 percent off duty cycle output of the PWM. By contrast, where the voltage from the CAM 702 to the PWM 502 is near the maximum voltage (vref) of the CAM, a resulting near 100 percent on/near-zero percent off duty cycle output of the PWM would result. Further, and accordingly, for each intermediate setting of the CAM 702 between minimum and maximum output voltage to the PWM 502, a corresponding intermediate percentage on/percentage off duty cycle output of the PWM would result. Thus, the CAM 702 enables varied output duty cycles of the PWM 502.

Figure 9:
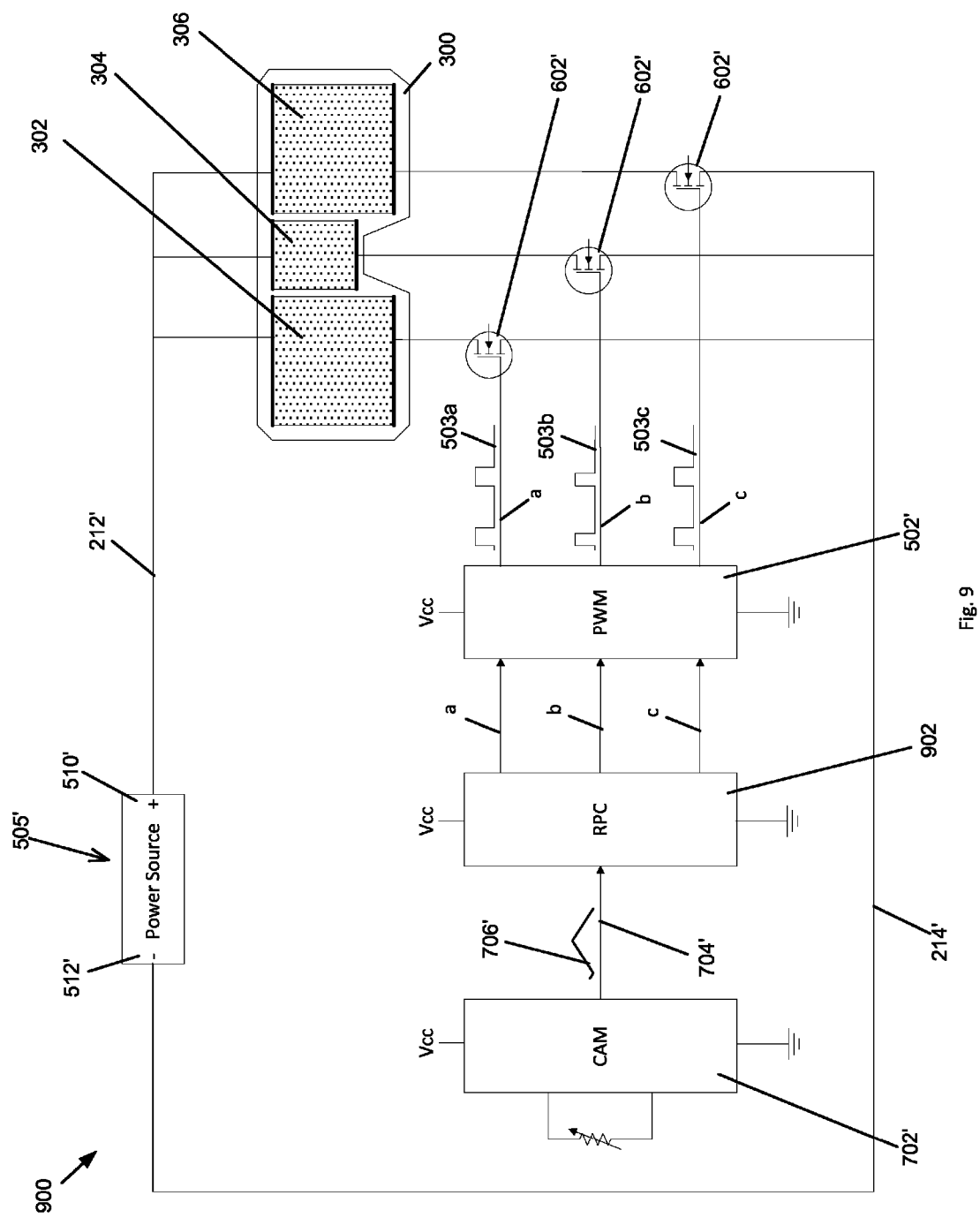
FIG. 9 is a schematic representation of still another embodiment of a multiple-PWM, multiple-region eye-shield fog prevention system in accordance with another aspect of the invention.

As further described below, a current adjustment means, such as CAM 702, may also be used with a multiple-region embodiment of the invention as shown in FIG. 9.

Dew Point Calculation and Automation

Figure 8:
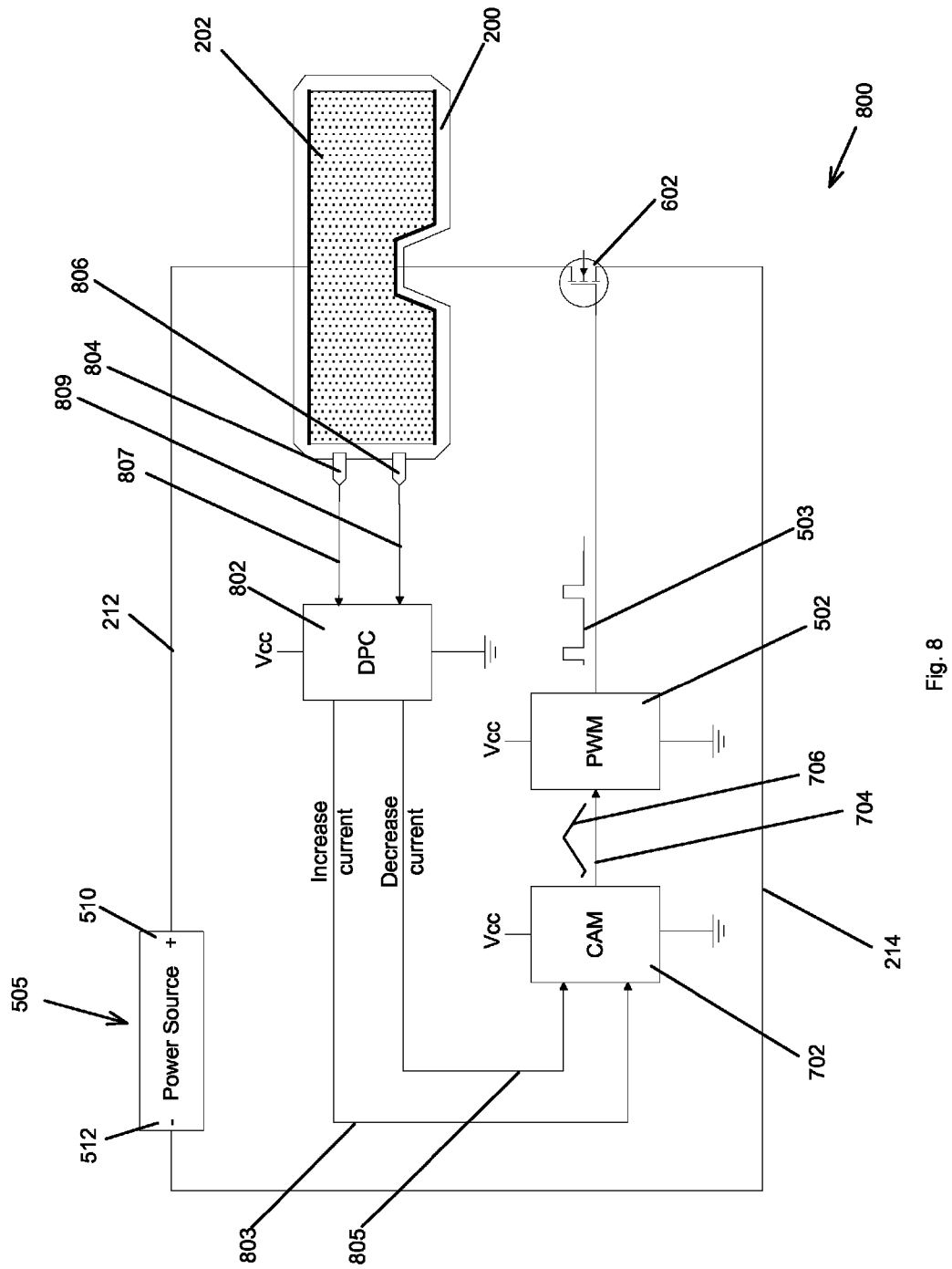
FIG. 8 is a schematic representation of yet another embodiment of an automated single-PWM, single-region eye-shield fog prevention system in accordance with another aspect of the invention.

Referring now to FIG. 8, a single-PWM, single-region fog prevention system 800 is shown comprising a power source 505 having positive and negative terminals 510, 512, circuit wires 212, 214, PWM 502 (which generates signal 503), MOSFET 602, eye-shield or lens 200 and heating element 202 which system is the same as system 700 except that system 800 further comprises means 802, preferably a microcomputer, for calculating dew point (dew point calculator, or DPC), a temperature sensor 804 and a relative humidity sensor 806 operatively connected to the DPC via signal means 807, 809 and in accordance with another aspect of the invention. This aspect of the invention enables automation of adjustment of the CAM based upon temperature sensor 804 and relative humidity sensor 806 inputs taken from sensing environmental conditions within the space defined between the eye-shield 200, near the heating element 202, and the user's eyes.

As shown, the DPC 802 is operatively connected with the CAM 702 via electrical signal means 803 to signal an increase in current and signal means 805 to signal a decrease in current such that the DPC signals the CAM when environmental conditions within the space defined by the eye-shield 200 have changed thus requiring an adjustment to the heating element 202 from the system 800. When the system 800 is initially started, the DPC 802 calculates the dew point temperature and compares it to the actual temperature within the space defined by the eye-shield 200 and signals the CAM 702 accordingly. If the dew point temperature, as calculated by the DPC 802, is greater than the temperature within a space defined between the eye-shield 200 and a user's eyes, then logic within the DPC signals to the CAM 700 to increase the voltage out to the PWM 502, which in turn increases the duty cycle of the PWM output, which in turn increases power to the heating element to increase the temperature of the eye-shield 200 and the space between the eye-shield and a user's eyes. Thus, subsequent sensory input to the system 800 from the temperature sensor 804, the relative humidity sensor 806, and calculations by the DPC 802, would all reflect not only changing ambient conditions, but temperature changes resulting from the aforementioned increase request from the system 800 as well. Further adjustments to the system 800 via the DPC 802 are made at regular intervals in the following manner: as temperature within the space defined by the eye-shield 200 falls below the dew point temperature threshold, the system 800 increases power to the heating element 202 via circuit wires 212, 214, and as temperature within the space defined by the eye-shield climbs above the dew point temperature threshold, the system decreases power to the heating element via the circuit wires. The aforementioned operation may employ hysteresis, such as used on a typical thermostat, between the increase and decrease states of the system 800 to avoid unwanted rapid switching.

Multiple-Region, Multiple-PWM Embodiment

Figure 3:
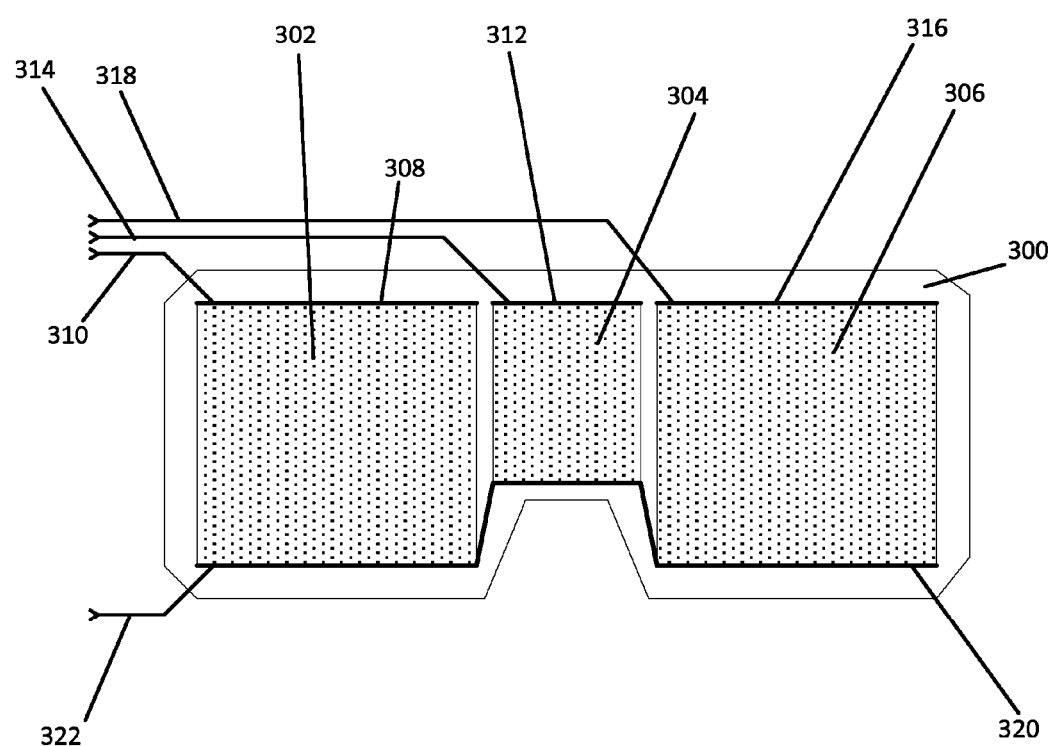
FIG. 3 is a front plan view schematic representation of an irregular-shaped eye-shield having a resistive heating element film heater thereon that is divided into a plurality of regions.

Referring to FIG. 3, there is provided in accordance with part of another, second, embodiment of the invention, an eye-shield lens or protective eyewear 300 adapted for at least partially defining an enclosure around a user's eyes and having thereon a plurality of regions or zones of resistive film heating elements or members 302, 304, 306. The film heating element 302 located over a user's right eye during use, is connected to the power source (not shown) by a bus-bar 308 positioned along an upper edge of the film and electrically connected between the film and a lead wire 310 leading to a terminal of the power source. The film heating element 304 located centrally of the eye-shield lens 300 just above a user's nose during use, is connected to the power source by a bus-bar 312 positioned along an upper edge of the film and electrically connected between the film and a lead wire 314 leading to a terminal of the power source. The film heating element 306, located over a user's left eye during use, is connected to the power source by a bus-bar 316 positioned along an upper edge of the film and electrically connected between the film and a lead wire 318 leading to a terminal of the power source. A buss-bar 320 positioned along the lower edge of each of the film elements 302, 304, 306 interconnects the film elements to the ground terminal of the power source.

As shown, the surface area of the film members 302, 306 is larger than the surface area of the film member 304, such that the resistance of the film member 304 is less than that of the other film members. Accordingly, in order to have even heating across the entire lens 300, less current should be applied to the film member 304 than the other film members. Or, alternatively, the divisions between the film members would allow independent heating of one or more of the film members, more or less, than the other film members.

Figure 4:
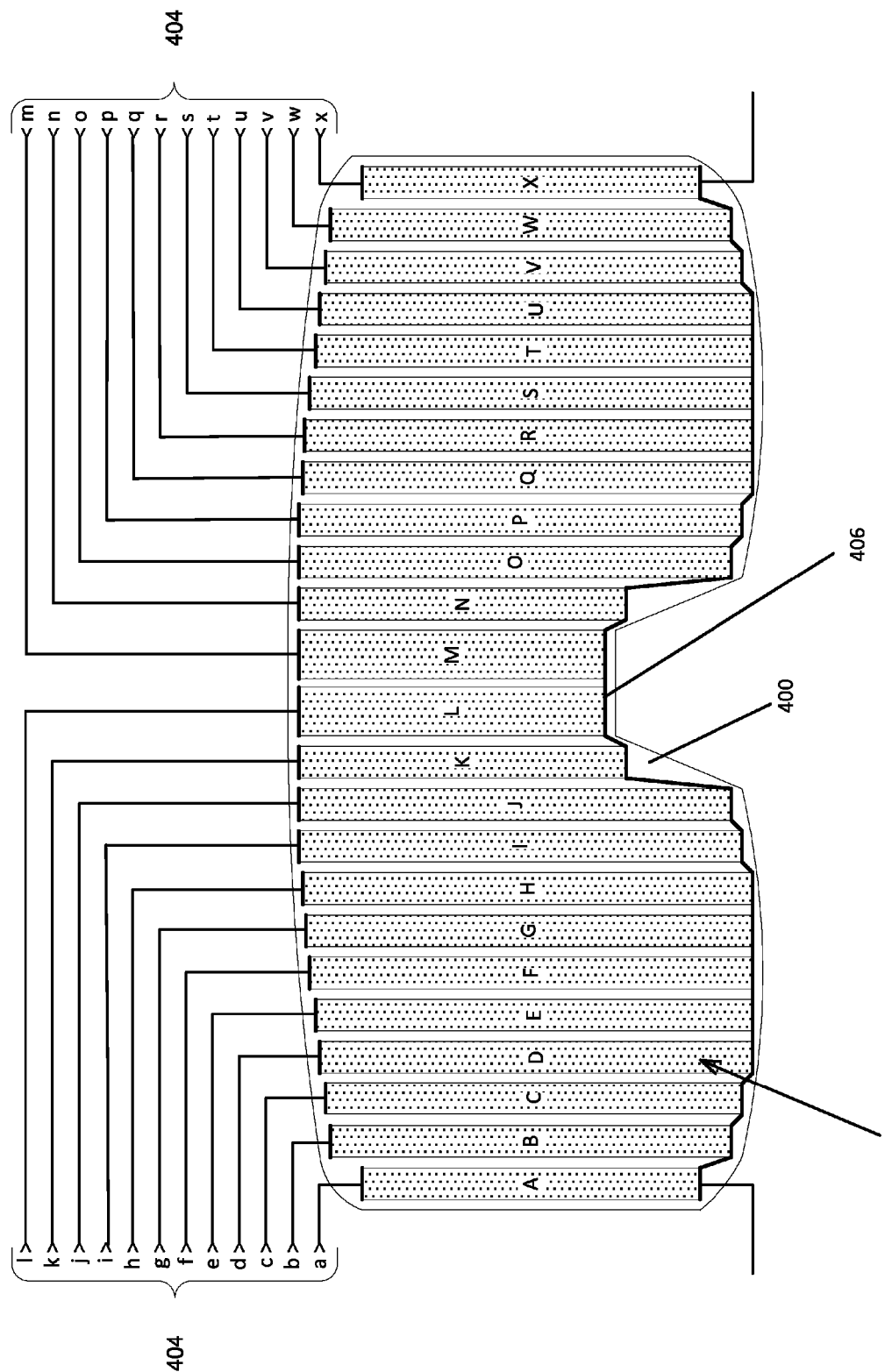
FIG. 4 is a front plan view schematic representation of an irregular-shaped eye-shield having a resistive heating element film heater thereon that is divided into a plurality of regions.

Referring to FIG. 4, an eye-shield lens 400 is provided in accordance with the second embodiment of the invention. The eye-shield 400 is adapted for at least partially defining an enclosure in front of the user's eyes and has deposited thereon a plurality (24 are shown in FIG. 4) of resistive heating film zones or regions 402 A-X. It will be appreciated that the resistive heating film may be divided into larger or smaller regions than shown without departing from the true scope and spirit of the invention. Each resistive film region 402 A-X is connected to a terminal of a power source via lead wires and discrete buss-bars 404 *a-x*. A single buss-bar 406, located along a lower edge of each resistive film region 402 A-X interconnects each of the lower ends of film regions to a ground terminal of the power source.

The resistive film regions of the fog prevention system of the present invention are preferably deposited on the inner surface of an eye-shield 200, 300, 400 with a process known as ion sputtering on a polycarbonate lens, but spray coating and other methods and materials known in the art may be used without departing from the true scope and spirit of the invention. The buss-bars are deposited on the lens 200, 300, 400 by stamping, adhesive backing, or in the case of a conductive silver epoxy buss-bar, it may be applied to a polycarbonate substrate. In the case of a dive mask, while attachment of the resistive film and buss-bars to the inner glass surface of the mask may be employed, a preferred alternative would be to apply these to an inner polycarbonate substrate within the mask. The methods and systems of application of the resistive film heaters and the buss-bars to various substrates are known in the art. Each buss-bar and its corresponding resistive film region are overlapped on edge portions of each so that they conduct electricity to and from the power source as is known in the art.

CAM and DPC in a Multiple-Region Embodiment

Figure 10:
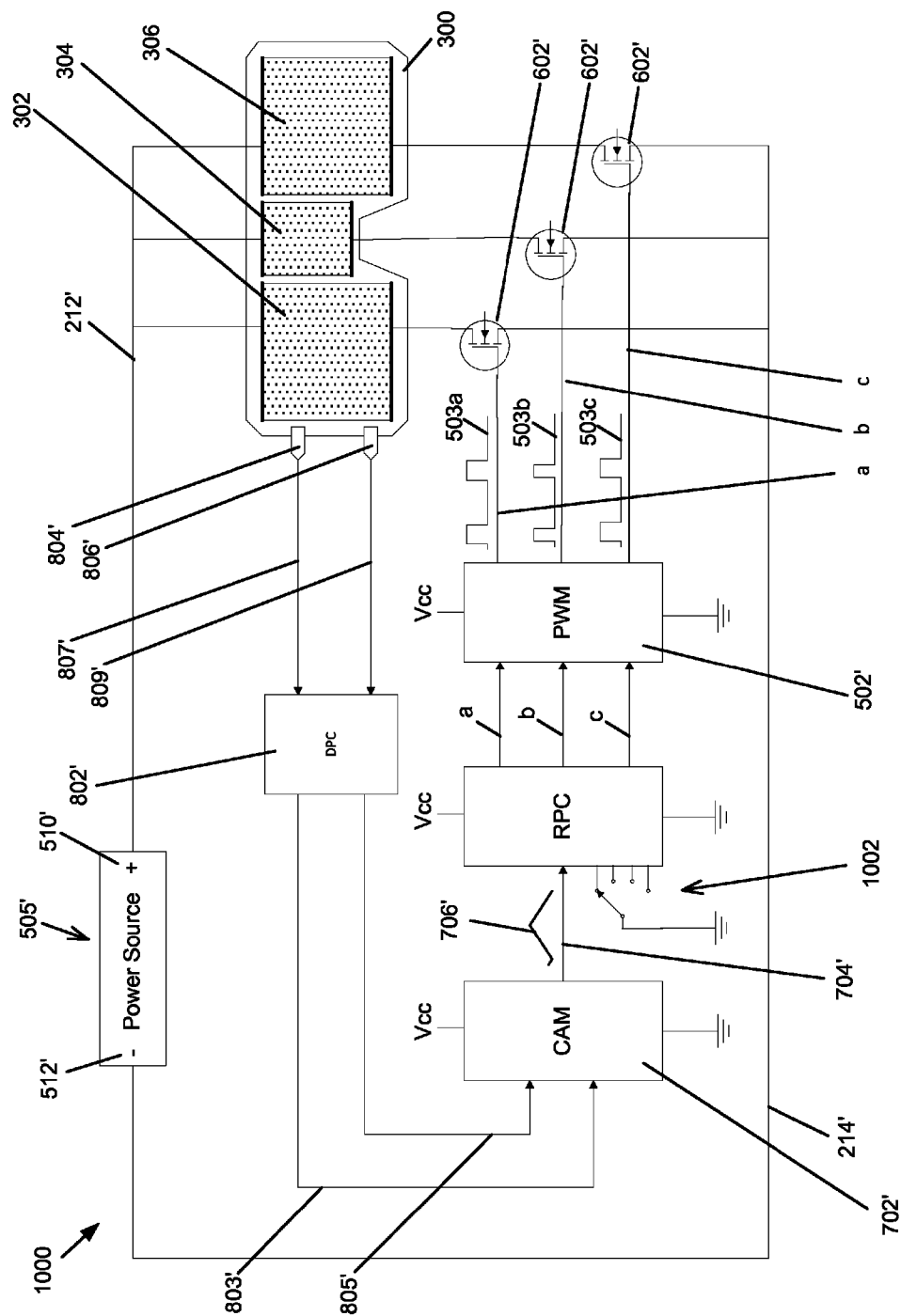
FIG. 10 is a schematic representation of another embodiment of an automated multiple-PWM, multiple-region eye-shield fog prevention system in accordance with yet another aspect of the invention.

The larger number of resistive film regions 302, 304, 306 in the multiple-region embodiment of the invention shown in FIG. 3, and alternatively the larger number of regions 402 A-X in the multiple-region embodiment of the invention shown in FIG. 4, enables more even heating of a wider variety of shapes and sizes of eye-shields 300, or alternatively 400, and requires a correspondingly larger number of Pulse-Width Modulators (PWMs), or PWM channels, in a multiple-region, multiple-PWM eye-shield fog prevention system as shown in FIGS. 9 and 10. Thus, it will be appreciated that, while a three-channel PWM system is shown in FIGS. 9 and 10, fewer or more channels may be provided to accommodate a like number of resistive heating element regions by using an appropriate number PWM channels to accommodate such a plurality of heating element regions.

As shown in FIGS. 9 and 10, a current adjustment means (CAM) may be employed with a multiple-region embodiment of the invention, and as shown in FIG. 10, a dew point calculation means (DPC) may also be incorporated into a multiple-region embodiment of the invention to enable automated adjustment of each region as described above. In the case of the CAM, the single output voltage of the CAM is received by a region profile control means (RPC) as further described below and used to adjust the input voltage to each of the multiple PWMs in that embodiment to allow varying of the current out of the PWM based upon user adjustment of a selector or to enable automation as further described below. The DPC of the multiple-region embodiment of the invention functions the same way as described above for the DPC in a single-region embodiment of the invention.

Balancing Profiles and Custom Profiles

Referring now to FIG. 9, a multiple-PWM, multiple-region fog prevention system 900 is shown comprising a power source 505' having positive and negative terminals 510', 512', circuit wires 212', 214', a multiple-channel PWM 502' which is shown generating signals 503a, 503b and 503c on channels a, b and c, respectively, a CAM 702', a plurality of MOSFETs 602', one MOSFET for each channel of the multiple-channel PWM, an eye-shield or lens 300 and heating element regions 302, 304, 306, which system is similar to the single-PWM systems described above, except that system 900 further comprises a region profile controller 902 primarily for balancing power delivered to different-sized and shaped resistive heating film regions (302, 304, 306, or alternatively, 402 A-X), on the eye-shield 300 or 400, respectively.

Differently shaped eye-shield lenses 300, 400 would require corresponding region profiles that reflect the shape of the lens and its individual regions such that the electrical characteristics of each region are appropriately weighted so that each region is assured the proper amount of power to keep it in balance with other regions. Thus a region profile is tied to the shape of a region (and the resulting electrical resistivity of that region) and the overall shape of the goggle. If one were to change the shape of a lens, then a different profile would be required for that lens.

Calculating the Resistance of Regions

Each of the regions 302, 304 and 306 have a calculated total electrical resistance (Rt) determined by a formula which considers the type of resistive coating used, and the area of the region where: Rt is the total resistance of the region in ohms, Ri is the resistance per square inch of the resistive thin film in ohms, H is the height of the region in inches and W is the width of the region in inches. Rt may be calculated using the following formula:

$$Rt = \frac{Ri * H}{W}$$

For example, considering the regions 302 and 306, given Ri is 10 ohms, H is 3 inches, and W is 3 inches. The total resistance (Rt) for each region 302 and 306 may be calculated as (10×3)/3 which equals 10 ohms. Now considering region 304, given an Ri of 10 ohms, H being 2 inches, and W being 1.6 inches, the total resistance (Rt) of the region 304 may be calculated as (10×1.6)/2 which equals 8 ohms. Thus, for a given voltage, due to a lower total resistance in 304 than in regions 302, 306, more power would be consumed in region 304 than in regions 302 and 306 causing a hot spot in region 304 as further verified below.

Calculating the Power Density of Regions

Each region 302, 304, 306 has a calculated Power Density (Pd) determined by a formula which considers the effective voltage (E) applied to the region, the resistance per square inch (Ri) of the resistive thin film in ohms, and the width (W) of the region in inches. Pd may be calculated using the following formula:

$$Pd = \frac{E^2}{Ri * W^2}$$

For example, considering regions 302 and 306, given an operating voltage of 10 volts for each region, Pd would equal $10^2/(10 \times 3^2)$ which equals 1.11 watts per square inch. Considering region 304, given the same operating voltage of 10 volts, region 304 Pd would equal $10^2/(10 \times 2^2)$ which equals 2.5 watts per square inch. These calculations show that, given an equal effective voltage for all regions, the center region 304 will be hotter than the outside region 302 and 306.

Determining Region Profile Proportional Control

Given the aforementioned determined hot spot over the nose of the user, proportional balancing of the regions is desirable. Such balancing requires a determination of an appropriate voltage level for region 304 which will provide the same power level output as regions 302 and 306 when powering regions 302 and 306 at 10 volts. Previously, according to the formula, $$\frac{E^2}{Ri * W^2} = 1.11 (Pd \text{ same as } 302)$$

and solving for E, $$E = \sqrt{Ri * W^2 * Pd}$$

and plugging in known values, E is equal to $\sqrt{10 * 2^2 * 1.11}$ which is equal to 6.66 volts.

Therefore, based on the width and height of the same material used in regions 302 and 306, to produce an equivalent power density, region 304 will need 0.666 times (or 66.6%) of the voltage applied to regions 302 and 304. This result is confirmed by re-calculating the power density (Pd) for region 304 as $6.66^2/(10 \times 2^2)$ which equals 1.11 watts per square inch.

Applying these calculations back to the reference output voltage produced by the CAM 702' on channels a and c, delivered to regions 302 and 306 respectively, will also require reduction of the reference output voltage on channel b by 66.6% compared to the values applied to channels a and c. In the case of analog circuitry this proportional control may be accomplished by use of a resistor network as will be appreciated by those of ordinary skill in the art. In the case of a digital implementation the values will be retrieved from a data table and the resulting power levels will be calculated and applied directly to the PWM channels using a microcomputer or equivalent digital circuitry as will be apparent to those of ordinary skill in the art.

Region Profile Matched to Shape or Region

Accordingly, it should be understood that when a larger region or regions receive 100% of the applied effective voltage, smaller regions should receive a proportionally smaller percentage of the applied effective voltage to balance the power density of all of the regions. While a specific example for a particularly shaped goggle has been provided, it will be appreciated that differently-shaped lens regions will require similar calculation and balancing profile determination. In the case of curved edge, or irregularly shaped regions, determination of region areas may require the application of known mathematical methods to determine the region area for use in the above-described calculations.

Balanced and Custom Profiles

The results in the foregoing example disclose a balancing profile. More precisely, these results yield the analog or digital proportional input voltages needed to power differing size regions on a specific goggle to the same power densities.

Region Custom Profile Switch and Automation

Referring to FIG. 10, a multiple-PWM, multiple-region fog prevention system 1000 similar to system 900 is shown comprising a power source 505' having positive and negative terminals 510', 512', circuit wires 212', 214', a multiple-channel PWM 502' which is shown generating signals 503a, 503b and 503c on channels a, b and c, respectively, a CAM 702', a plurality of MOSFETs 602', one MOSFET for each channel of the multiple-channel PWM, an eye-shield or lens 300 and heating element regions 302, 304, 306. System 1000 differs from system 900 in that in system 1000 the RCP 902 further comprises a user-selectable region profile control switch 1002 which enables a user to select a balanced profile or one of several custom profiles for customized power delivery as further described below to the different-sized and shaped resistive heating film regions (302, 304, 306, or alternatively 402 A-X) on the eye-shield 300 or 400, respectively.

A custom profile may be used to enable predetermined proportional input voltages to a particular resistive film region, or regions, necessary to achieve a desired power density pattern allowing one or more regions 302, 304, 306, or alternatively 402 A-X, to intentionally become hotter or cooler than other regions for specific intended purposes. Together with the DPC 802' and sensors 804', 806', the CAM 702' provides overall automatic variability between all the way cool to all the way hot for each of the regions 302, 304, 306, or alternatively regions 402 A-X, and it is the job of the RPC 902' cognizant of the profile to know how much power to apply proportionally to each of the regions in accordance with the overall adjustment. For example for a given dew point calculation, the CAM 702' may be set to a 50% overall power application or duty cycle, the RPC will put out a 50% adjustment for the largest region 302, 304, 306 (or alternatively 402 A-X) and a proportionally smaller output for smaller regions in accordance with a particular predetermined profile.

Examples of custom profiles may involve a profile for a snow boarder that may require added heat to one side of a goggle lens to prevent fogging or to reduce icing of that side depending upon which foot the rider usually leads downhill, or as another example, a particular lens or goggle shape and configuration may require added heating at the edges of the goggle to prevent fogging or icing. Alternatively, further it would be desirable to provide custom settings for particular weather conditions, such as a rainy day, a snowy day, a sunny day, or different depths and water temperatures for a dive mask, etc. Custom profiling may be user-selectable with the custom profile switch 1002.

The multiple-PWM, multiple-region fog prevention system 1000 shown in FIG. 10 also further comprises means for calculating dew point 802' (also known as the dew point calculator, or DPC), a temperature sensor 804' and a relative humidity sensor 806' operatively connected to the DPC via signal means 807', 809' for automated control of the system 1000. The DPC 802' and sensors 804', 806' are for the same purposes and function in the same way as the DPC 802 and sensors 804, 806 shown and described above in connection with the first embodiment of the invention, except the signals from the DPC 802' are used by the CAM and RPC to provide master controls for a plurality of signal lines a, b, c to the PWM 502'.

From the foregoing it can be seen that many of the aspects of the invention, such as dew point calculation, automation and current adjusting means may be employed to either of the first or second embodiments of the invention, whereas the RPC is primarily adapted for the second embodiment of the invention employing a plurality of regions on the eye-shield.

System Overview

While preferably the PWMs of either embodiment of the invention, and associated functions such as dew point calculation, profile table lookup, variable current adjustment mechanism, switching means, and the like, may be preferably accomplished with a microcomputer, any of these functions may be performed with other technology, such as a programmable logic array (PLA), a state machine, analog circuitry or other digital logic, without departing from the true scope and spirit of the invention.

Figure 11:
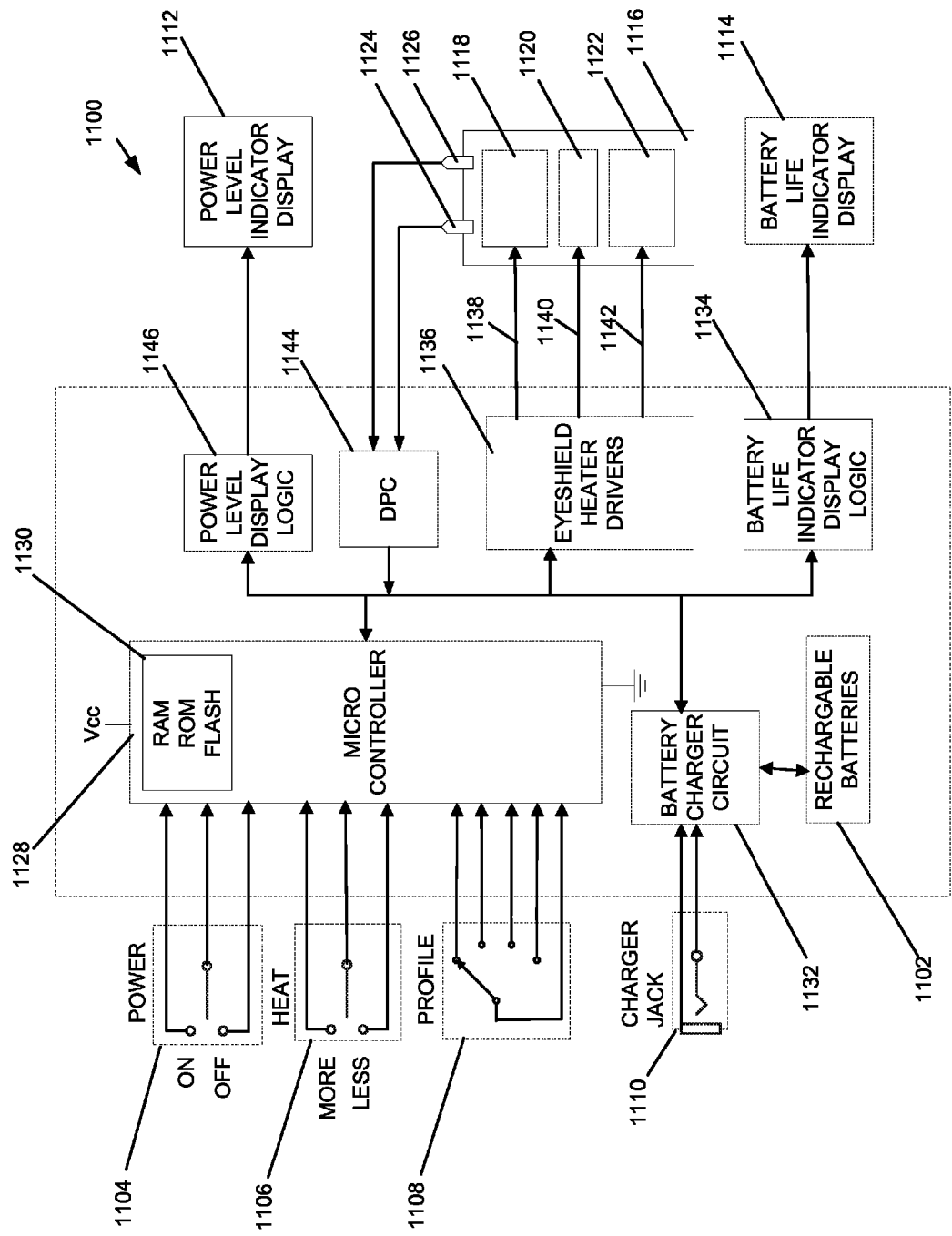
FIG. 11 is a schematic representation of a micro-computer controlled embodiment of an automated multiple-PWM, multiple-region eye-shield fog prevention system also including a charger.

Referring to FIG. 11, there is provided a preferred embodiment of a digital version of a multiple-channel PWM, multiple-region fog prevention system 1100. System 1100 comprises a power source, such as rechargeable batteries 1102, an on/off switch 1104, a heat control switch 1106, a profile selector 1108 and a charger jack 1110. Charger jack 1110 may comprise a mini-USB charger jack or other suitable charging system as known in the art. System 1100 further comprises a power level indicator display 1112 preferably comprising a plurality of LEDs configured as a bar graph to indicate a selected power level and a battery life indicator display 1114 preferably comprising a plurality of LEDs configured as a bar graph to indicate remaining battery life. System 1100 further comprises an eye-shield 1116 having deposited thereon a plurality of thin film heating elements 1118, 1120, 1122. The eye-shield 1116 is adapted for defining at least a partial enclosure in front of a user's eyes. A temperature sensor 1124 and a relative humidity sensor 1126 are positioned within the partial enclosure defined by the eye-shield 1116 for aiding with calculation of dew point temperature.

The system 1100 further preferably comprises a low-power microcontroller 1128 preferably further comprising PWM logic, other programmable logic and some combination of RAM/ROM/FLASH Memory 1130 as is known in the art of microelectronics. The microcomputer controller 1128 is operatively connected to a battery charger circuit 1132. The battery charger circuit 1132 is connected to the battery charger jack 1110 and rechargeable batteries 1102. The battery charger circuit 1132 is primarily responsible for maintaining the rechargeable batteries 1102, including routing a charge from the charger jack 1110 to the rechargeable batteries when required and turning off, disconnecting the charger from the batteries when they have been fully charged and reporting battery level to the microcontroller 1128. The system 1100 further comprises battery life indicator display logic 1134 such that when the microcontroller 1128 receives battery level information from the battery charger circuit as previously described, the microcontroller may signal the battery life indicator display logic upon user request or otherwise. The battery life indicator display logic 1134 converts the signal received from the microcontroller 1128 into the logic necessary to drive the battery life indicator display 1114. The battery life indicator display logic 1134 may include a latch to hold the latest value on the display, relieving the microcomputer to attend to other tasks.

The system 1100 further comprises an eye-shield heater driver 1136 comprising a plurality of driver channels 1138, 1140, 1142, each channel corresponding to a thin film heating element region or zone, such as regions 1118, 1120, 1122, respectively. The primary responsibility of the microcontroller 1128 is to keep the heater driver 1136 and related channels 1138, 1140, 1142 operating at an optimal and preferably balanced level to eliminate and prevent fogging while conserving battery life. The microcontroller 1128 may operate in manual heat control or automatic heat control modes. In the manual heat control mode, responsive to an input from the more or less heat switch 1106, the microcontroller 1128 adjusts power to the eye-shield heater driver 1136 according to a predetermined profile contained in microcontroller memory 1130 and which controls the duty cycle signal on each individual PWM channel in a manner consistent with the size, shape and electrical resistivity of each associated heating element 1118, 1120, 1122 to provide power density balancing.

In the situation where some other custom profile, other than power density balancing, is desired, responsive to input from profile selector switch 1108, the system 1100 may engage a custom profile, also stored in microcontroller memory 1130, resulting in application of a custom power density profile to the heater driver 1136 resulting in a desired portion of the eye-shield 1116 receiving more power than another portion.

The system 1100 further comprises a dew point calculator (DPC) 1144 which calculates dew point temperature from temperature sensor 1124 and relative humidity sensor 1126. During automatic mode balancing of heating levels of the system 1100, the system adjusts the heat to the regions in accordance with a calculated dew point from the DPC 1144. When the system 1100 is initially started, the DPC 1144 calculates the dew point temperature and compares it to the actual temperature within the space defined by the eye-shield 1116 and signals the microcontroller 1128 accordingly. If the dew point temperature, as calculated by the DPC 1144, is greater than the temperature within the space defined between the eye-shield 1116 and a user's eyes, then logic within the microcontroller signals to the eye-shield heater driver 1136 to increase the duty cycle of the PWM channels in accordance with the profile in effect to increase the temperature of the eye-shield 1116 and the space between the eye-shield and a user's eyes. Thus, subsequent sensory input to the DPC 1144 from the temperature sensor 1124, the relative humidity sensor 1126, and calculations by the microcontroller 1128, would all reflect not only changing ambient conditions, but temperature changes resulting from the aforementioned increase request from the system 1100 as well. Further adjustments to the system 1100 via the DPC 1144 are made by the microcontroller 1128 at regular intervals in the following manner: as temperature within the space defined by the eye-shield 1116 falls below the dew point temperature threshold, the system 1100 increases power to the heating elements 1118, 1120, 1122 via PWM channels 1138, 1140, 1142, and as temperature within the space defined by the eye-shield climbs above the dew point temperature threshold, the system 1100 decreases power to the heating elements via the PWM channels. The aforementioned operation may employ hysteresis, such as used on a typical thermostat, between the increase and decrease states of the system 1100 to avoid unwanted rapid switching.

In both the manual and automatic operation modes of the system 1100, it is preferable for the user to be apprised of the power level being supplied to the heating elements of the system. This is especially useful in the manual mode when the user may set the power at a predetermined level in accordance with visual feedback from the power level display. In response to manual changes from the more/less heat switch 1106, and/or at regular intervals, the microcontroller 1128 determines from memory 1130 the current operating power level being supplied to the heater driver 1136 and sends a power level signal to the power level display logic 1146, which in turn converts the signal received from the microcontroller 1128 into the logic necessary to drive the power level indicator display 1112. The power level indicator display logic 1146 may include a latch to hold the latest value on the display, relieving the microcomputer to attend to other tasks.

Prior Voltage Regulation System

Figure 12:
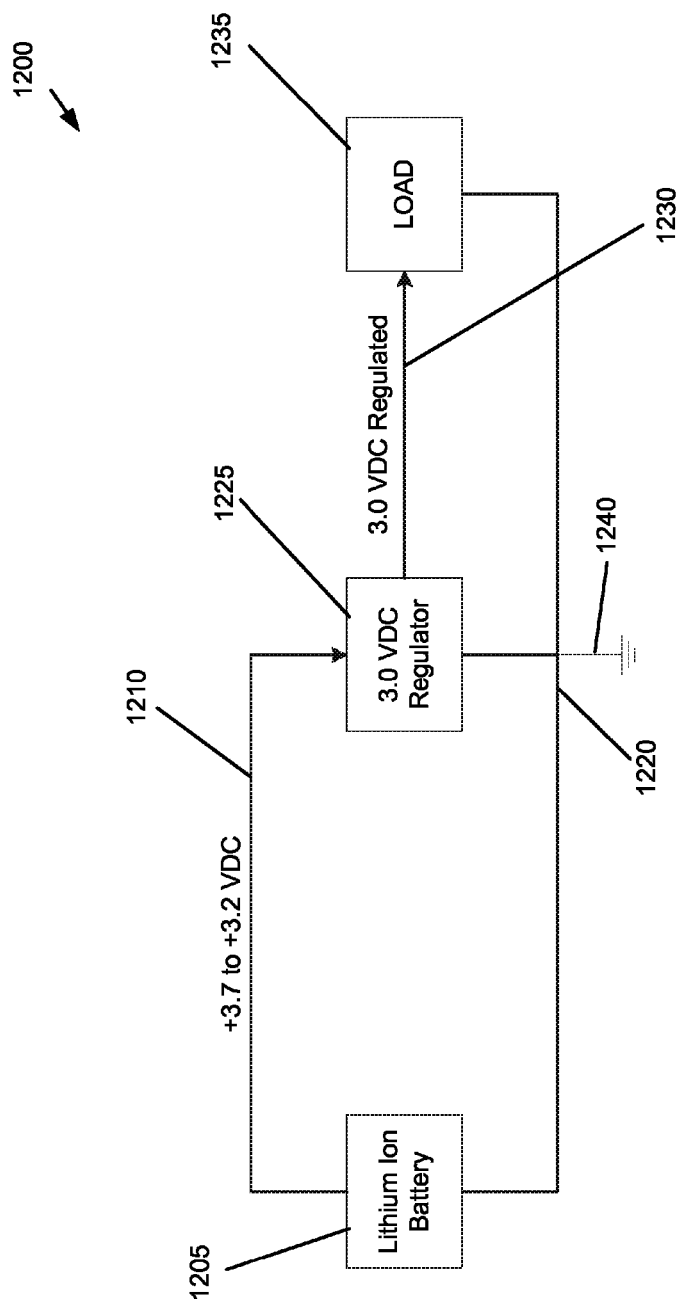
FIG. 12 is a block diagram of a prior system for regulating battery voltage that otherwise depletes over time in use.

Referring now to FIG. 12, a block diagram of a battery regulation system is illustrated for maintaining a constant regulated voltage to a hand-held electronic device, such as a cell phone (represented by load 1235), including a lithium-ion battery 1205, a positive circuit wire 1210 carrying 3.7 to 3.2 Volts DC, which is depleting with battery discharge over time in use as specified, to a voltage regulator 1225. The voltage regulator 1225 is set to supply a regulated, constant 3.0 Volts DC via line 1230 as specified to the load 1235. A typical voltage regulator supplies voltage at the desired output level only when the actual supply voltage from the battery is somewhat greater than the desired output voltage. Thus, for example, where the desired output voltage is to be 3.0 Volts DC, the battery voltage would need to be at least 3.2 Volts DC for the voltage regulator to produce the desired 3.0 Volts DC. The circuit back to the negative terminal of the battery 1205 is completed with circuit line 1220, and the system is grounded at 1240. Such a system is known to be important to provide constant voltage necessary to efficient functioning of cell phones.

Battery Compensation System Using PWM

Unlike the aforementioned battery regulation system 1200 shown and described above, a battery compensation system using PWM differs in that it does not maintain a constant voltage until the battery is discharged, but rather it varies the PWM cycle to maintain constant power to the load despite the voltage drop until the battery is discharged and no longer able to maintain that power level.

Figure 13:
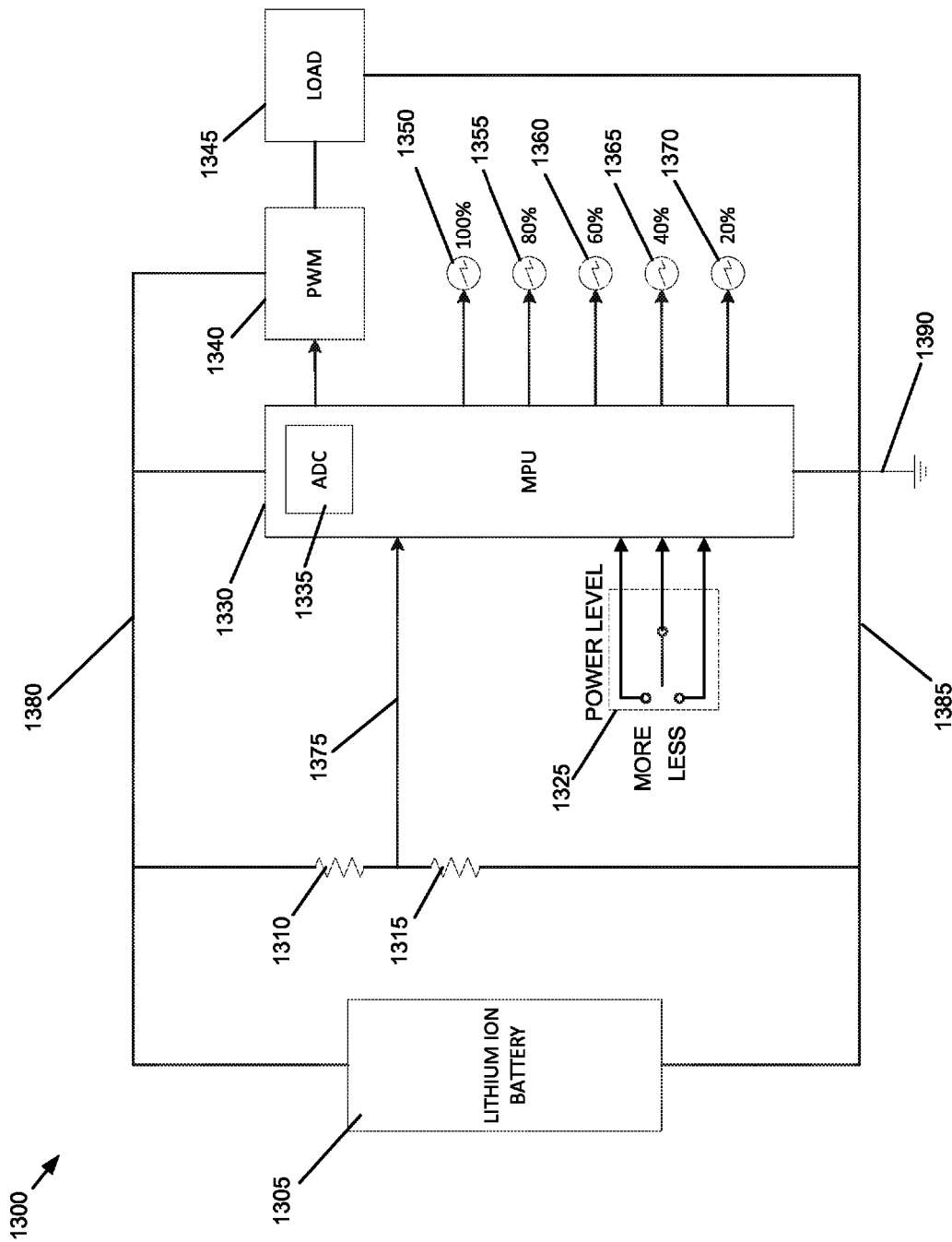
FIG. 13 is a block diagram of an alternate embodiment of a battery compensation system in accordance with an aspect of the invention.

Thus, referring now to FIG. 13, a battery compensation system 1300 using pulse-width modulation (PWM) 1340 is shown comprising a battery 1305, preferably a lithium-ion battery, having positive parallel circuit lines 1380 leading to a voltage divider circuit 1310, 1315 for proportionally adjusting the voltage to a measurable range, an analog to digital converter 1335 for receiving the output from the voltage divider and converting it into a digital voltage value, a microprocessing unit (MPU) 1330 and a single-channel pulse-width modulator (PWM) 1340. Preferably, the voltage divider circuit 1310, 1315 comprises two resistors 1310, 1315 in series between positive and negative terminals of the battery 1305 for proportionally adjusting the voltage to a measurable range, the voltage divider circuit preferably having a tap between the two resistors (shown as the intersection of lines between the two resistors 1310, 1315) adapted to provide the proportional voltage measurement to an I/O pin on the analog-to-digital converter 1335. Preferably, the user-determined, or provided, power setting comprises a power level setting set by a dial, a knob, or a push button system 1325, together with some form of visual feedback to the user (e.g., 1612 of FIG. 16) to further enable selection of the setting.

The PWM 1340 drives the load 1345, which represents a portable electronic device, or elements of a portable electronic device, such as for example heating elements on an anti-fog ski goggle, a heated diving mask, a heated medical or technical eye-shield, or the like. Alternatively, the load 1345 may represent a heater on a portable electronic device such as a hand-held GPS unit, a cell phone, a radio, an electronic tablet, a reader, or other portable computer or the like, to be driven by the PWM circuitry and battery of the device. A power level selector 1325 is provided with more and less controller for allowing user selection of a desired power setting, such as 20%, 40%, 60%, 80% 100%, corresponding to, for example, 2 Watts, 4 Watts, 6 Watts, 8 Watts and 10 Watts respectively 1350, 1355, 1360, 1365, 1370 respectively, for power to drive a heater (e.g., heating element 202 of FIG. 5) on the powered electronic device (e.g., an anti-fog goggle). The MPU 1330 is one of several possible means for receiving voltage input and user-determined power setting input for determining a compensating duty cycle 1350, 1355, 1360, 1365, 1370 for application to the PWM 1340 to drive the load consistently at the user-determined power setting despite decrease in voltage from the battery 1305 resulting from battery depletion.

Figure 14:
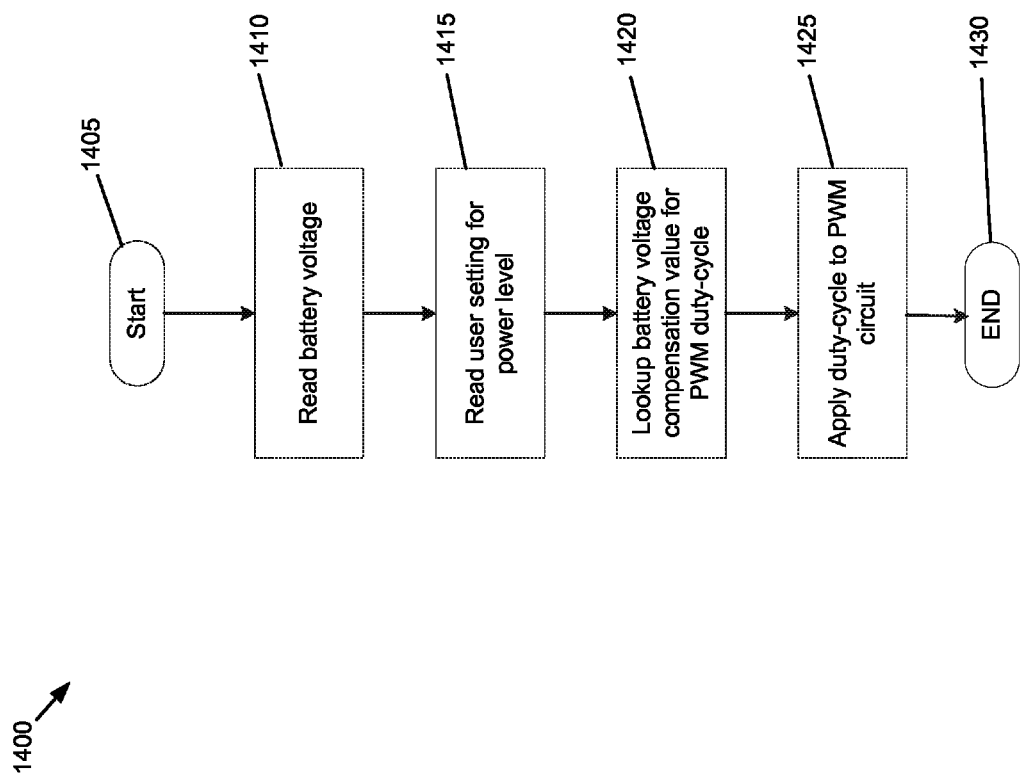
FIG. 14 is a flow diagram of software steps for performing the functions of a battery compensation system in accordance with the present invention.

Referring now also to FIG. 14, the MPU 1330 is capable of executing software code steps 1400 as set forth in the flow chart, to determine a compensating duty cycle 1350, 1355, 1360, 1365, 1370 for application by the software to the PWM 1340 to drive the load 1345 consistently at the user-determined power setting despite decrease in battery voltage resulting from depletion of the battery 1305. For this embodiment of the invention, preferably the MPU 1330 is battery-powered, and a readily-available microprocessing unit having on-board analog-to-digital conversion means 1335 may be used for the present invention.

The software steps as shown at 1405 for operation of the invention comprise, after starting at 1405, reading of the battery voltage 1410, reading the user setting for power level 1415, looking up the battery voltage compensation value for a PWM duty cycle 1420 to be applied to the PWM circuit 1425. The process ends at 1430, and the steps 1400 are repeated frequently as needed to maintain compensated power in accordance with the invention during operation of the system. While the portable electronic device 1345 (e.g., 200 of FIG. 5) is powered on, the compensation system of the invention may be operated continuously, or it may be controlled with an on/off switch to toggle between battery conservation mode and battery compensation mode. As indicated by line 1430 for as long as the device power is on and the battery is sufficiently charged and capable of supplying the power necessary to power the device in battery compensation mode. While battery conservation mode will use less battery power, battery compensation mode in accordance with the invention may be employed when extra battery power is available to compensate for a drop in voltage resulting from battery depletion by increasing the duty cycle 1350, 1355, 1360, 1365, 1370 to be applied to the PWM 1340 to overcome what would otherwise be a drop in power associated with the depleted battery 1305.

Still further, as shown in FIGS. 14 and 15, determination of a compensating duty cycle 1350, 1355, 1360, 1365, 1370 may comprise a data lookup table 1500 of PWM duty cycle values organized according to power setting (shown in Watts across the top of the table 1500) and battery depletion voltage drop (shown in the left-hand column of FIG. 15) and for use by the code steps 1410, 1415, 1420, 1425 run by the microprocessor to select a compensating duty cycle for application to the PWM to drive the load 1345 consistently at the user-determined power setting despite a decrease in voltage from the battery 1305 resulting from battery depletion. This embodiment of the invention preferably comprises a lookup table 1500 stored in microprocessor memory (e.g., 1630 of FIG. 16) which, as is true of software data table controls in general, provides generally faster operation and is easier to code than using floating-point calculations, though it will be appreciated that either may be used to implement the invention in accordance with its true spirit and scope. Further, while conceivably a discrete logic circuit could be used to perform the functions of the compensation system of the invention, such would likely be unduly expensive to implement and no more effective than the software and data table lookup functions that are preferred for the invention.

The data lookup table 1500 shown in FIG. 15 is organized by user heater level setting (shown in Watts across the top of the table 1500) and actual heater power for a given battery voltage ranging from 8.4 Volts DC (assuming two lithium-ion batteries of 3.7 Volts DC each in series) depleted down to 6.8 Volts DC (shown in the left-hand column of the table 1500). Thus, for example, when the battery 1305 is at full power (that is there has been no depletion of battery charge yet), and 2 Watts of total power has been selected by a user, 11.3 on cycles (out of 100.0 total cycles) will need to be on. As can be seen from the FIG. 15, the number of duty cycles increases as shown as a greater number of Watts is specified by the user, and a larger number of duty cycles is required to compensate for increasingly depleted charge in the battery. Thus for example, 86.5 duty cycles (that is PWW will switch the power on 86.5 cycles for every 100 cycles—or in other words the PWM controls transmission of power to allow power to the load 86.5 cycles out of a hundred, or 86.5 on and 13.5 off). Thus, as can be seen the number of duty cycles required increases as the battery depletes further and the higher the power level selected by the user. While the example data table 1500 is based upon a system using two lithium-ion batteries of 3.7 Volts DC each in series, the invention is not limited to a two-battery, or otherwise plural-battery, system, and the battery compensation system of the invention may be used with a single battery with an appropriately adjusted data table, or calculations as the case may be. Further, while the number of duty cycles is represented as an integer with a decimal portion, these numbers may be rounded to the nearest integer in an actual PWM implementation.

In an alternate embodiment, the software steps 1410, 1415, 1420, 1425 themselves may be used to calculate a compensating duty cycle 1350, 1355, 1360, 1365, 1370 for application to the PWM 1340 to drive the load 1345 consistently at the user-determined power setting despite decrease in voltage from the battery 1305 resulting from battery depletion. The formula for determining the compensating duty cycle 1350, 1355, 1360, 1365, 1370 for this embodiment of the invention, which is the same formula used to determine data table 1500 duty cycle values (from user input power settings—represented by the Watts settings across the top of table 1500—and measured voltage) used in the table is as follows:

$$\text{Duty Cycle} = \frac{\text{Desired Power} * \text{Load Resistance}}{(\text{Battery Voltage})^2} * 100$$

The compensation system 1300 in accordance with the invention enables maintenance of a user-selected and/or desired power setting to drive the load 1345 to consistently heat a portable device (e.g., goggle lens 200 of FIG. 5), such as anti-fog goggles or a hand-held GPS, radio or phone, despite partial depletion of a device battery 1305, as long as there is sufficient battery charge to maintain the system-compensated power output. Thus, as the voltage from the battery 1305 drops resulting from battery depletion from use over time, the system 1300 compensates by increasing the duty cycle 1350, 1355, 1360, 1365, 1370 of the PWM 1340 driver for the device 1345.

Figure 16:
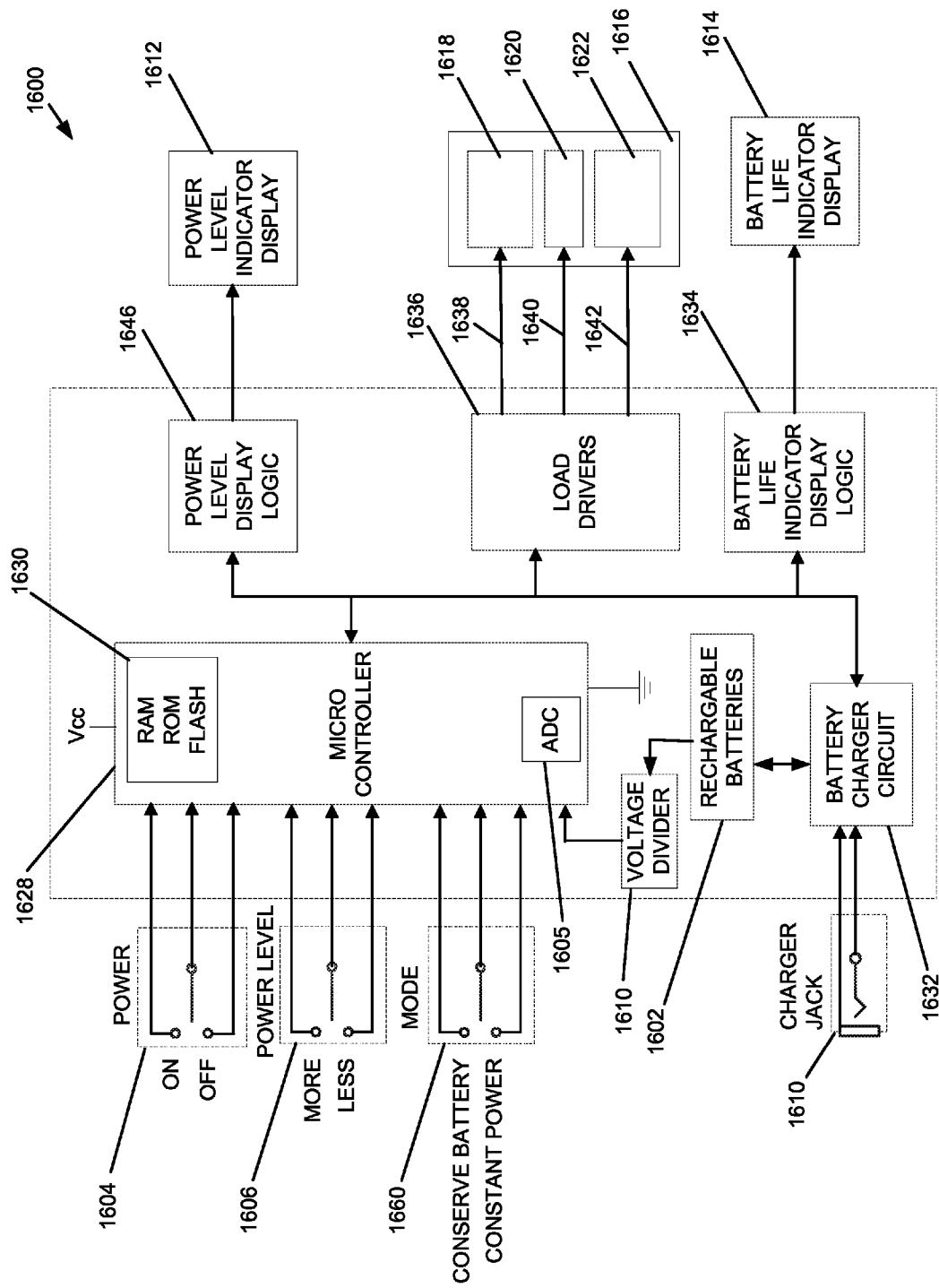
FIG. 16 is a block diagram of an alternate embodiment of a battery compensation system adapted for a multi-load device.

Referring now to FIG. 16, there is shown a compensation system 1600 adapted for use preferably in heating a plurality of devices, for example a plurality of loads 1618, 1620, 1622 of a portable electronic device 1616. The plurality of loads 1618, 1620, 1622 represent a portable electronic device, elements of a portable electronic device, or a plurality of such devices, such as heating elements on an anti-fog ski goggle, a heated diving mask, a heated medical or technical eye-shield, or the like. Alternatively, the load 1345 may represent a heater or other appropriately PWM driven element on a portable electronic device such as a hand-held GPS unit, a cell phone, a radio, an electronic tablet, a reader, or other portable computer or the like, to be powered by the PWM circuitry and battery of the device. The example compensation system 1600 comprises a power source, such as rechargeable batteries 1602, an on/off switch 1604, a power level control 1606 and a charger jack 1610. Charger jack 1610 may comprise a mini-USB charger jack or other suitable charging system as known in the art. System 1600 further comprises a power level indicator display 1612 preferably comprising a plurality of LEDs configured as a bar graph to indicate a selected power level and a battery life indicator display 1614 preferably comprising a plurality of LEDs configured as a bar graph to indicate remaining battery life. System 1600 further comprises a portable electronic device 1616 having illustrated therewith a plurality of loads 1618, 1620, 1622.

The system 1600 further preferably comprises a low-power microcontroller 1628 preferably further comprising PWM logic, other programmable logic and some combination of RAM/ROM/FLASH Memory 1630 as is known in the art of microelectronics. The microcomputer controller 1628 is operatively connected to a battery charger circuit 1632. The battery charger circuit 1632 is connected to the battery charger jack 1610 and rechargeable batteries 1602. The battery charger circuit 1632 is primarily responsible for maintaining the rechargeable batteries 1602, including routing a charge from the charger jack 1610 to the rechargeable batteries when required and disconnecting the charger from the batteries when they have been fully charged and reporting battery level to the microcontroller 1628. The system 1600 further comprises battery life indicator display logic 1634 such that when the microcontroller 1628 receives battery level information from the battery charger circuit as previously described, the microcontroller may signal the battery life indicator display logic upon user request or otherwise. The battery life indicator display logic 1634 converts the signal received from the microcontroller 1628 into the logic necessary to drive the battery life indicator display 1614. The battery life indicator display logic 1634 may include a latch to hold the latest value on the display, relieving the microcomputer to attend to other tasks.

The system 1600 further comprises drivers 1636 comprising a plurality of driver channels 1638, 1640, 1642, each channel corresponding to a load, such as loads 1618, 1620, 1622, respectively. Preferably, MOSFET for system 1600 is contained in the drivers 1636. The primary responsibility of the microcontroller 1628 is to keep the driver 1636 and related channels 1638, 1640, 1642 operating at an optimal and preferably balanced level while conserving battery life. Responsive to an input from the power level control 1606, the microcontroller 1628 adjusts power to the device driver 1636 according to a predetermined profile contained in microcontroller memory 1630 and which controls the duty cycle signal on each individual PWM channel in a manner consistent with the size, shape and electrical resistivity of each associated load 1618, 1620, 1622 to provide power density balancing.

In the situation where some other custom profile, other than power density balancing, is desired, the system 1600 may engage a custom profile, which may be stored in microcontroller memory 1630, resulting in application of a custom power level profile to the driver 1636 resulting in a desired portion of the portable electronic device 1616 receiving more or less power than another portion.

The system 1600 using pulse-width modulation (PWM) (contained in the microcontroller 1628 comprises a voltage divider circuit 1610 for proportionally adjusting the voltage to a measurable range, and an analog to digital converter (ADC) 1605 preferably contained in the microcontroller 1628 for receiving the output from the voltage divider and converting it into a digital voltage value. Preferably, the voltage divider circuit 1610 comprises two precision resistors in series (as described above in connection with FIG. 13) between positive and negative terminals of a battery or batteries 1602 for proportionally adjusting the voltage to a measurable range, the voltage divider circuit preferably having a tap between the two resistors adapted to provide the proportional voltage measurement to an I/O pin on microcontroller 1628 containing the analog-to-digital converter 1605. Preferably, the user-determined, or provided, power setting comprises a power level setting set by a dial, a knob, or a push button system (e.g., 1606), together with some form of visual feedback to the user (e.g., 1612) to further enable selection of the setting.

As part of system 1600, it is preferable for the user to be apprised of the power level being supplied to the load elements of the system. Thus, a user may select a desired power level in accordance with visual feedback from the power level display 1612. In response to manual changes from the power level control 1606, and/or at regular intervals, the microcontroller 1628 determines from memory 1630 the current operating power level being supplied to the driver 1636 and sends a power level signal to the power level display logic 1646, which in turn converts the signal received from the microcontroller 1628 into the logic necessary to drive the power level indicator display 1612. The power level indicator display logic 1646 may include a latch to hold the latest value on the display, relieving the microcomputer to attend to other tasks.

Referring now to FIG. 17, there is shown an alternate data lookup table 1700 stored in microprocessor memory 1630 for allowing software determination of an applied duty cycle corresponding to a custom power level profile, for example for each load of a plurality of different loads, in a portable electronic device, for example when less than full power to the device may be desirable. The data lookup table 1700 shown in FIG. 17 is organized by user heater level setting (shown in Watts across the top of the table 1700) and actual heater power for a given battery voltage ranging from 8.4 Volts DC (assuming two lithium-ion batteries of 3.7 Volts DC each connected in series) depleted down to 6.8 Volts DC (shown in the left-hand column of the table 1700). Thus, for example, when the battery 1602 is at full power (that is there has been no depletion of battery charge yet), and 1.5 Watts of total power has been selected by a user, 8.5 on cycles (out of 100.0 total cycles) will need to be on. As can be seen from the FIG. 17, the number of duty cycles increases as shown as a greater number of Watts is specified by the user, and a larger number of duty cycles is required to compensate for increasingly depleted charge in the battery. Thus for example, 64.9 duty cycles (that is PWW will switch the power on 64.9 cycles for every 100 cycles—or in other words the PWM controls transmission of power to allow power to the load 64.9 cycles out of a hundred, or 64.9 on and 35.1 off). Thus, as can be seen the number of duty cycles required increases as the battery depletes further and the higher the power level selected by the user. While the example data table 1700 is based upon a system using two lithium-ion batteries of 3.7 Volts DC each in series, the invention is not limited to a two-battery, or otherwise plural-battery, system, and the battery compensation system of the invention may be used with a single battery with an appropriately adjusted data table, or calculations as the case may be. Further, while the number of duty cycles is represented as an integer with a decimal portion, these numbers may be rounded to the nearest integer in an actual PWM implementation.

The table 1700 may be part of a more comprehensive data table and still fall within the true scope and spirit of the invention, however it is contemplated that the system 1600 will ascertain the battery voltage and the user-determined power level input, and determine the appropriate duty cycle according to those inputs and in harmony with either an even power level profile, or alternatively a custom power level profile, such as would the be case for example in an evenly-heated eye-shield device or a custom-heated eye-shield device described previously for example in connection with FIG. 11.

While a preferred embodiment of the present invention has been shown and described, it will be apparent to those skilled in the art that many changes and modifications may be made without departing from the invention in its broader aspects. For example, it will be appreciated that one of ordinary skill in the art may mix and match the various components of the various embodiments of the invention without departing from the true spirit of the invention as claimed. Thus, by way of example, it will be appreciated that while the system 1100 discloses a preferred way of accomplishing the purposes of invention, it will be appreciated by those of ordinary skill in the art that other combinations of microcontrollers and/or microcontrollers may be used to accomplish the purposes hereof without departing from the true scope and spirit of the invention. The appended claims are therefore intended to cover all such changes and modifications as fall within the true spirit and scope of the invention.

Battery Power-Saving Method and System

Exemplary embodiments of the present invention shown in FIGS. 18-21 provide various embodiments and aspects of a power-saving method and system for efficiently heating an eye-shield apparatus that is adapted for use with a thin-film heater, and that is powered by a power source which is used to efficiently and effectively clear and further prevent fogging of the eye-shield while, optionally, employing PWM to regulate power application and compensating for battery depletion to provide consistent power to the eye-shield.

Figure 18A:
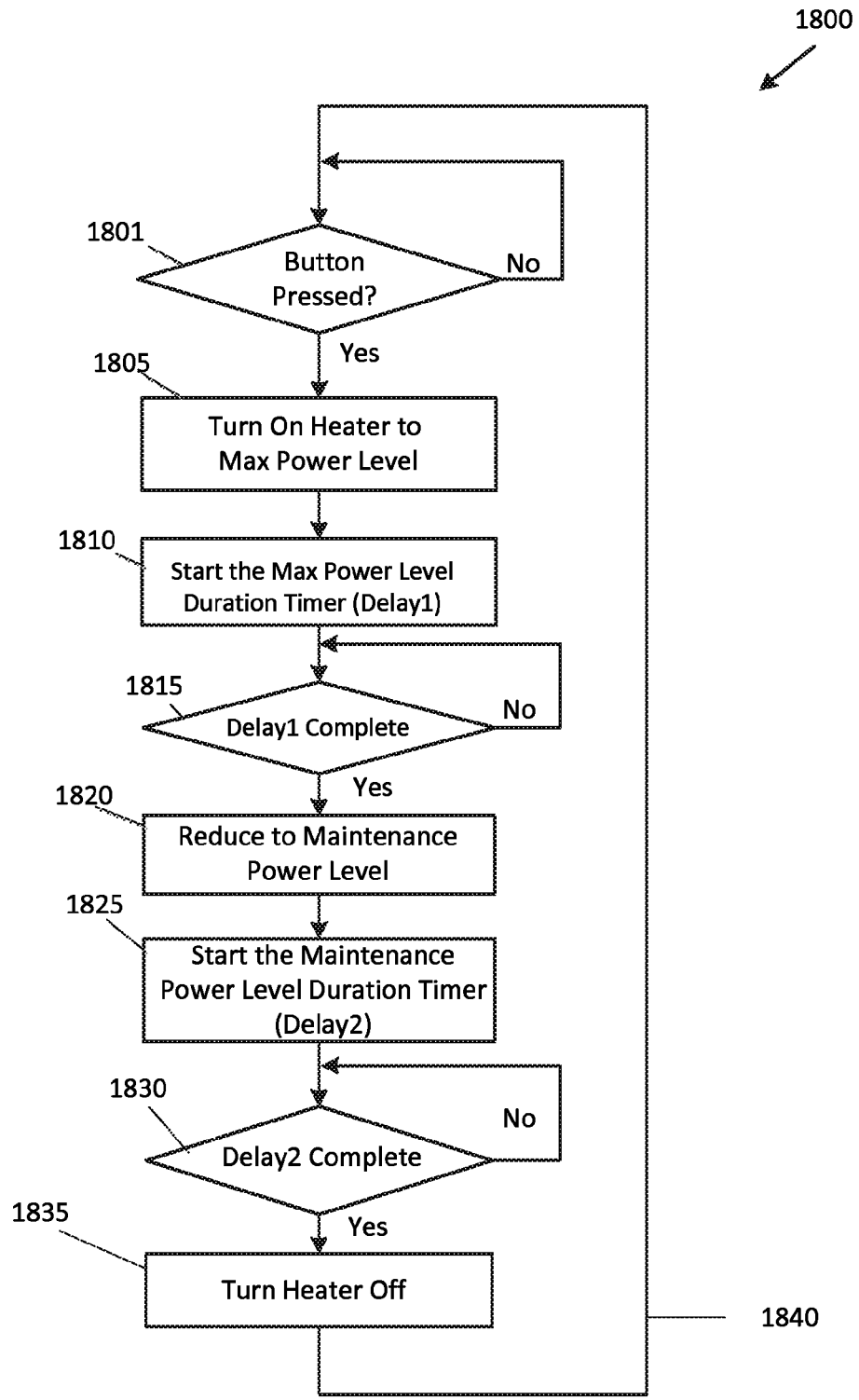
FIG. 18a is a flow diagram illustrating steps of a battery power-saving method and system in accordance with an aspect of the invention.

Referring specifically to FIG. 18a, a flow diagram illustrating an aspect of the method and system 1800 of the invention, referred to as an on-demand mode of the system. The on-demand mode system 1800 shown in FIG. 18a comprises the steps of activating the heater, which is preferably done by an electronic system on board the eye-shield frame, e.g., system 1100 shown in FIG. 11, detecting whether a button is pressed 1801 by the user. If the button is not pressed at decision diamond 1801, the heater will remain in the off position until it is detected that the button is pressed. The program for controlling the application of the method of this aspect of the invention is accomplished, for example, with a microcontroller 1128.

Once it is detected that the button is pressed at decision diamond 1801, the heater is turned on to one of a substantially higher, substantially highest, or maximum, power level 1805 (hereafter "max power level"), in a maximum heat, or maximum power, mode. Turning or setting the power on to a max power level 1805, and supplying a max power level to a heating element, e.g., 1118, 1120, 1122 on an eye-shield 1116 (or heater 202 of eye-shield 200 of FIG. 6 or 7), quickly raises the temperature of the eye-shield, dissipating fog and condensation rapidly. In accordance with one embodiment of this aspect of the present invention, the max power level comprises a maximum power level. Providing maximum power to the heater on the eye-shield accelerates heating of the eye-shield, and thus the rate at which fog and condensation dissipates.

After the heater is turned on to a max power level 1805, there begins a duration timer 1810 for the max power level. During the duration timer for the max power level 1810, a max power level is supplied to the heater that is available from the power source 1602 (FIG. 16). Sustaining the max power level assists in dissipating fog and condensation rapidly and fully from the eye-shield 1616. Powering the heater 1118, 1120, 1122 at max power level continues until a first duration of time (Delay1) is complete as shown at decision diamond 1815.

Once enough time lapses such that the first duration of time is complete at 1815, the power supplied then automatically lessens under program control by the microcontroller 1628 to the heater, and is turned on to an intermediate maintenance mode heating power level 1820, a level between the off power level and the max power level. The intermediate maintenance power level 1820 continues the process of dissipating any remaining fog or condensation on the eye-shield and additionally assists in preventing re-formation of fog and condensation on the eye-shield.

After the intermediate maintenance heating mode power level is turned on 1820, there begins a duration timer at 1825 for the intermediate maintenance heating power level. During the duration timer at 1825 for the intermediate maintenance mode heating power level, the intermediate power level is supplied to the heater from the power source. Sustaining the intermediate power level continues to prevent future fogging of the eye-shield, and additionally, preserves battery life, since it is an automatically-provided lower power level relative to the fog-burn-off power level, or max power level, applied to dissipate existing fog.

Powering the heater at the intermediate power level 1820 continues until a duration of time 1825 (Delay2) is complete as shown at decision diamond 1830. Once this duration of time 1825 is complete 1830, the heater returns to the off position 1835, where no power is supplied to the heater from the power supply. The heater will remain in the off position as indicated at 1840 until the user pushes the button 1801 to begin the power-saving method again. Each successive activation of the max power level in accordance with this aspect of the invention preferably restarts the max power level duration timer 1810, after which the maintenance level duration timer 1825 runs its course, in effect resetting the amount of time that the system will remain in this mode, which may be referred to as an on-demand mode.

Figure 18B:
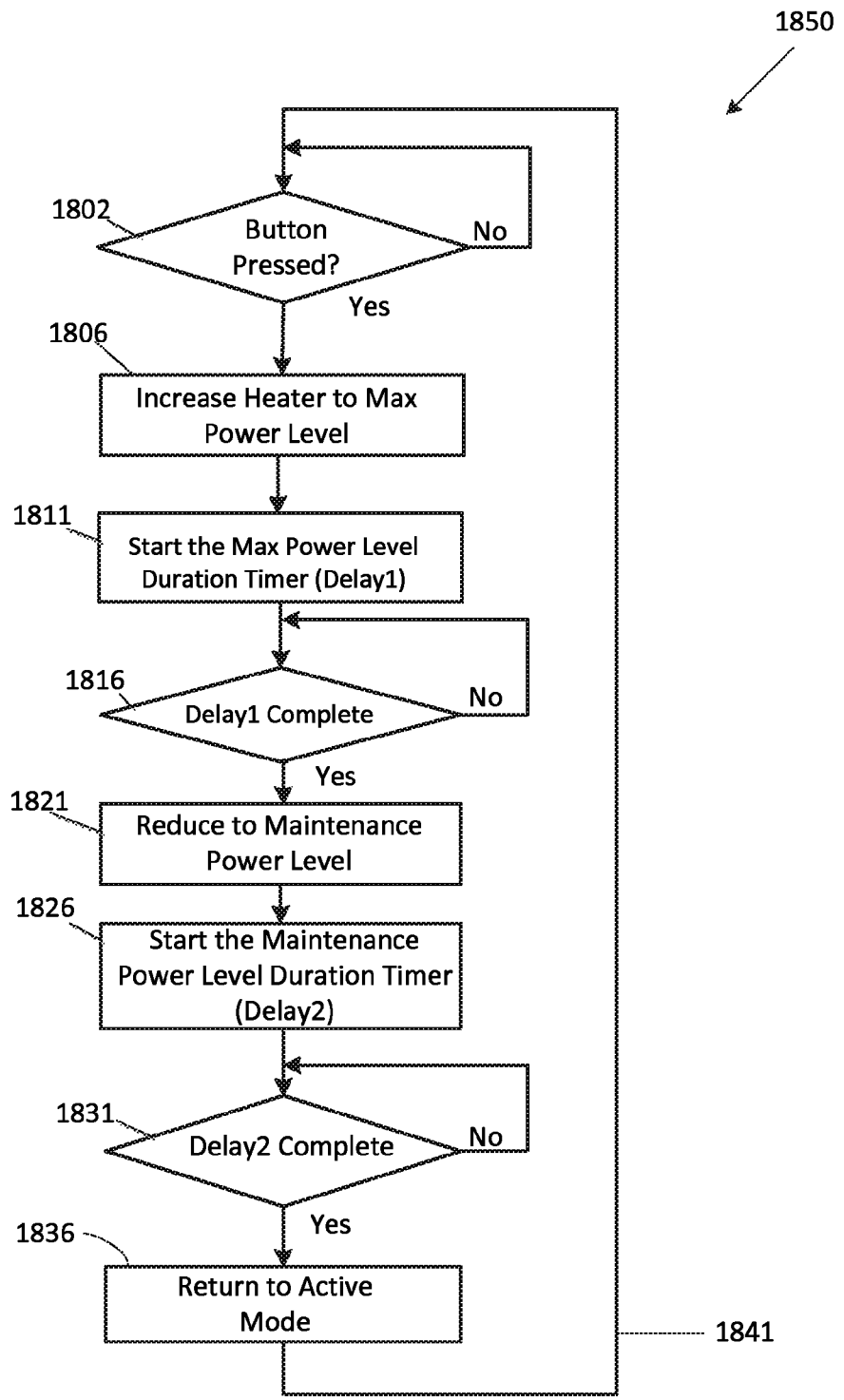
FIG. 18b is a flow diagram illustrating steps of a battery power-saving method and system in accordance with another aspect of the invention.

In another aspect of the method and system of the invention shown at 1850 in FIG. 18b, an active-on mode of the system as contrasted with the on-demand mode described previously. FIG. 18b shows a flow diagram illustrating an aspect of the method and system 1850 of the invention, comprising the steps of activating the heater, which is preferably done by an electronic system on board the eye-shield frame, e.g., system 1100 shown in FIG. 11, detecting whether a button is pressed 1802 by the user. If the button is not pressed, the heater will remain in the active-on state or mode until a button press is detected at 1802. The program for controlling the application of the method of this aspect of the invention is accomplished, for example, within microcontroller 1628.

Once it is detected that the button is pressed at 1802, the heater is turned on to one of a substantially higher, substantially highest, or maximum, power level 1806 (hereafter "max power level"), or maximum heat/power mode. Turning or setting the power on to a max power level 1806, and supplying a max power level to a heating element, e.g., 1118, 1120, 1122 on an eye-shield 1116 (or heating element 202 on eye-shield 200 of FIG. 7), quickly raises the temperature of the eye-shield, dissipating fog and condensation rapidly. In accordance with one embodiment of this aspect of the present invention, the max power level comprises a maximum power level. Providing maximum power to the heater on the eye-shield accelerates heating of the eye-shield, and thus the rate at which fog and condensation dissipates.

After the heater is turned on to a max power level 1806, there begins a duration timer 1811 for the max power level. During the duration timer for the max power level 1811, the max power level is supplied to the heater that is available from the power source 1102 (FIG. 11). Sustaining this max power level assists in dissipating fog and condensation rapidly and fully from an eye-shield 1616. Powering the heater 1118, 1120, 1122 at max power level continues until a first duration of time 1811 (Delay1) is complete as shown at decision diamond 1816.

Once enough time lapses such that the first duration of time is complete at 1816, the power supplied then automatically lessens under program control by the microcontroller 1628 to the heater, and is turned on to an intermediate maintenance mode heating power level 1821, a level between the off power level and the max power level. The intermediate power level 1821 continues the process of dissipating any remaining fog or condensation on the eye-shield and additionally assists in preventing re-formation of fog and condensation on the eye-shield.

After the intermediate maintenance heating mode power level is turned on at 1821, there begins a duration timer at 1826 for the intermediate maintenance heating power level. During the duration timer at 1826 for the intermediate maintenance heating power level, the intermediate power level is supplied to the heater from the power source. Sustaining the intermediate power level continues to prevent future fogging of the eye-shield, and additionally, preserves battery life, since this is an automatically supplied lower power level than would be the case if the user were simply trying to manually manage the defogging of the eye-shield.

Powering the heater at the intermediate power level 1821 continues until a duration of time 1826 (Delay2) is complete as shown at decision diamond 1831. Once this duration of time 1826 is complete at 1831, the heater returns to the active mode state 1836, where the preliminary intermediate power level is supplied to the heater from the power supply until either the battery becomes substantially fully depleted or the user turns the active mode of the system off. The heater will remain in the active mode position as indicated at 1841 until the user pushes the button as shown at decision diamond 1801 to begin the power-saving method again.

Alternatively, the method and system duration timer 1831 for the intermediate maintenance heating power level 1826 may be provided as indefinite, or infinite, such that the system stays at the intermediate power level indefinitely until either the battery becomes substantially fully depleted or the user reactivates the max power level at 1802, 1806. In either situation, the heater will remain in active-on position in accordance with this aspect of the invention shown in FIG. 18b until the user activates the max power level of the power-saving method again.

Entry into the on-demand mode may be determined by a short button press, whereas entry into the active-on mode may be determined by a longer button press. Further, a user may enter either the on-demand mode, or alternatively the active-on mode, from an off power position as determined, for example, by the length of the button press encountered.

Figure 19A:
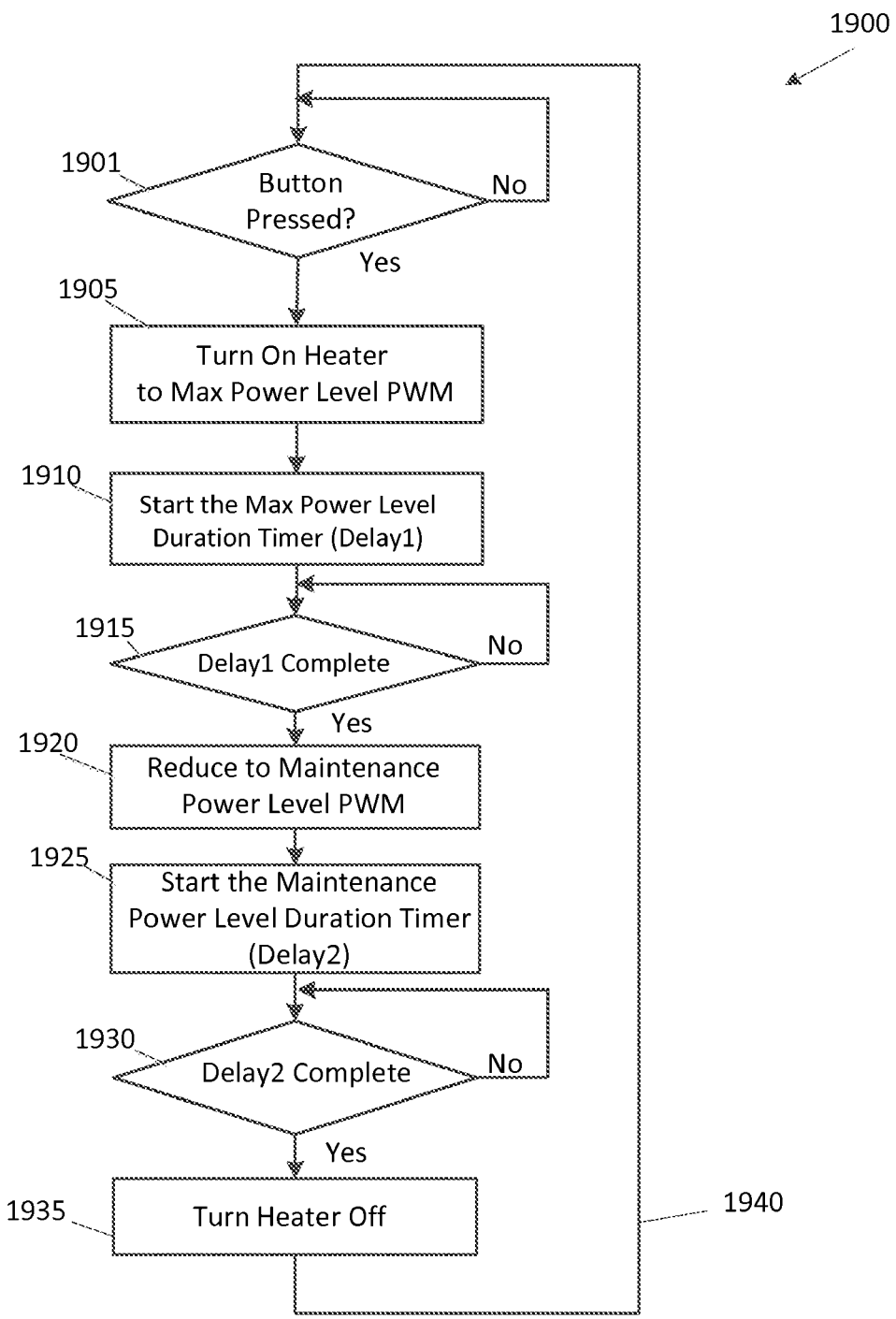
FIG. 19a is a flow diagram illustrating steps of a power-saving method and system in accordance with another embodiment of the aspect of the invention shown in FIG. 18a and including use of a pulse-width modulator.

Referring now to FIG. 19a, there is shown at 1900 another on-demand mode exemplary embodiment of the method and system including use of a pulse-width modulator (PWM) for performing the functions of effectively and efficiently heating an eye-shield while conserving battery power in accordance with the present invention. As illustrated in FIG. 19a, the heater is activated at 1901, 1905, which is preferably done by an electronic system on board the eye-shield frame, e.g., system 1100 shown in FIG. 11, detecting whether a button is pressed as shown at 1901, 1905, which is done by an electronic system detecting whether a button is pressed by the user. If the button is not pressed at decision diamond 1901, the heater will remain in the heater off position until it is detected by the system that the button is pressed.

Once the system detects that the button is pressed at 1901, the battery begins supplying power so that the heater is turned on to one of a substantially higher, a substantially highest, or a maximum, power level at 1905 (hereafter "max power level"), or maximum heat/power mode. Turning or setting the power on to a max power level 1905, by increasing power control to a higher percentage PWM on-time cycle, such as say 80%, 90% or 100% power on, and thus supplying a max power level to a heating element, e.g., 1118, 1120, 1122 on an eye-shield 1116 (or heater 202 of eye-shield 200 of FIG. 6 or 7), quickly raises the temperature of the eye-shield, dissipating fog and condensation rapidly. In accordance with one embodiment of this aspect of the present invention, the max power level comprises a maximum power level. Providing maximum power to the heater on the eye-shield accelerates heating of the eye-shield, and thus the rate at which fog and condensation dissipates.

After the heater is turned on to a max power level 1905, there begins a duration timer 1910 for the max power level. During the duration timer for the max power level 1910, a max power level is supplied to the heater that is available from the power source 1102 (FIG. 11). Sustaining the max power level assists in dissipating fog and condensation rapidly and fully from the eye-shield 1616. Powering the heater 1618, 1620, 1622 at max power level continues until a first duration of time (Delay1) is complete as shown at decision diamond 1915.

Once enough time lapses such that the first duration of time is complete at 1915, the power supplied then automatically lessens under program control by the microcontroller 1128 to the heater, by reducing the percentage of on-cycle PWM applied to an intermediate percentage level such as for example somewhere between 10% and 70% on-cycle PWM, and is turned on to an intermediate maintenance mode heating power level at 1920. The intermediate percentage level is provided to be any level between the off power level and the max power level, but preferably comprises a 50% PWM on-cycle power level. The intermediate maintenance power level 1920 continues the process of dissipating any remaining fog or condensation on the eye-shield and additionally assists in preventing re-formation of fog and condensation on the eye-shield.

Powering the heater at the intermediate power level using PWM at 1920 continues until a duration of time 1925 (Delay2) is complete as shown at decision diamond 1930. Once this duration of time 1925 is complete 1930, the heater returns to the off position 1935, where no power is supplied to the heater from the power supply. The heater will remain in the off position as indicated at 1940 until the user pushes the button 1901 to begin the power-saving method again. Each successive activation of the max power level in accordance with this aspect of the invention preferably restarts the max power level duration timer 1910, after which the maintenance level duration timer 1925 runs its course, in effect resetting the amount of time that the system will remain in this mode, which may be referred to as an on-demand mode.

Figure 19B:
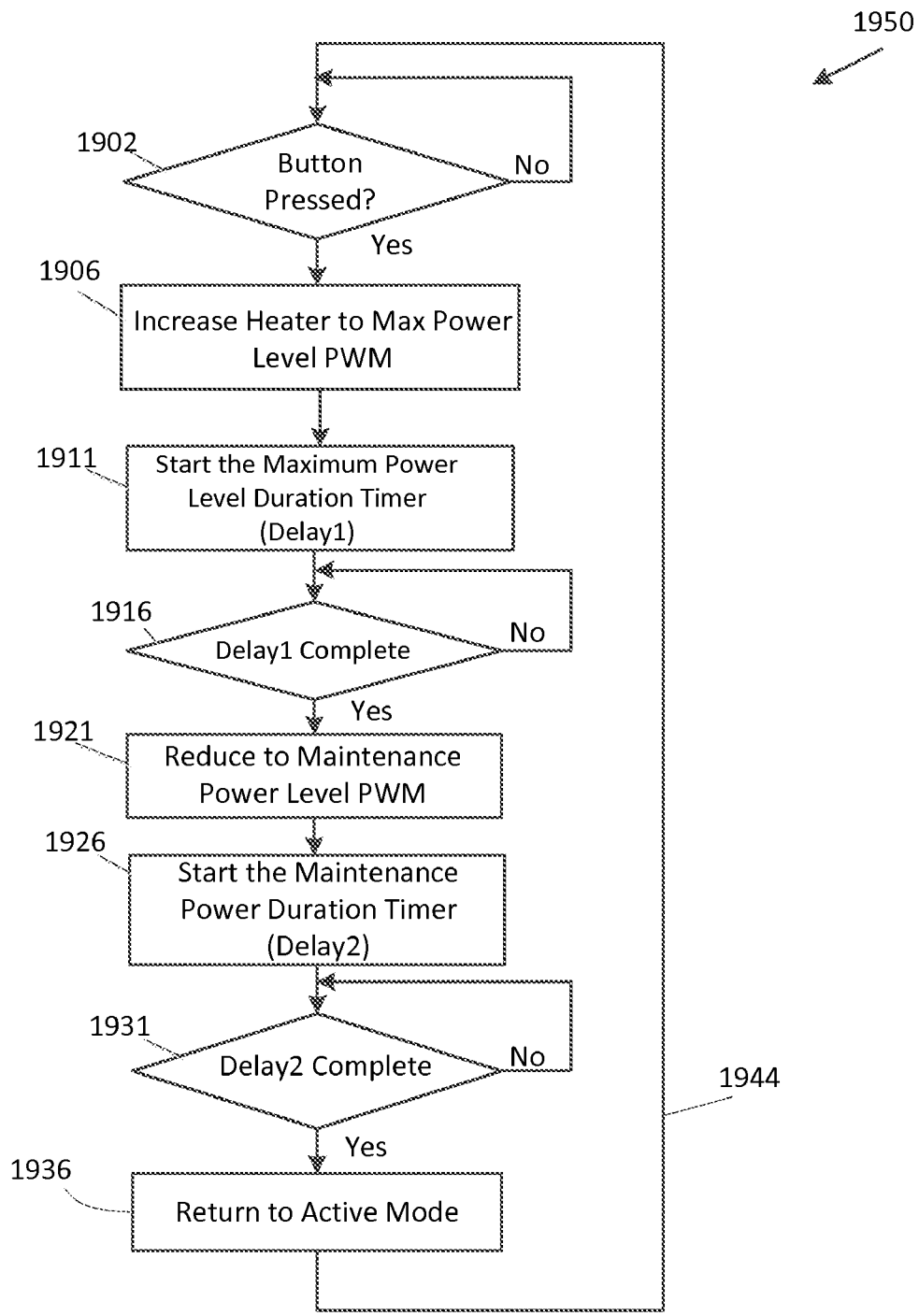
FIG. 19b is a flow diagram illustrating steps of a power-saving method and system in accordance with another embodiment of the aspect of the invention shown in FIG. 18b and including use of a pulse-width modulator.

In another aspect of the method and system of the invention shown at 1950 in FIG. 19*b*, an active-on mode of the system as contrasted with the on-demand mode described previously. FIG. 19*b* shows a flow diagram illustrating an aspect of the method and system 1950 of the invention, comprising the steps of activating the heater using PWM, which is preferably done by an electronic system on board the eye-shield frame, e.g., system 1100 shown in FIG. 11, detecting whether a button is pressed 1902 by the user. If the button is not pressed, the heater will remain in the active-on mode until a button press is detected at 1902. The program for controlling the application of the method of this aspect of the invention is accomplished, for example, within microcontroller 1128.

Once it is detected that the button is pressed at 1902, the heater is turned on to one of a substantially higher, substantially highest, or maximum, power level 1906 (hereafter "max power level"), or maximum heat/power mode using PWM. Turning or setting the power on to a max power level 1906 using PWM, for example to an 80%, 90%, or 100% or other substantially higher power level on-cycle setting of the PWM controller, and thus supplying a max power level to a heating element, e.g., 1118, 1120, 1122 on an eye-shield 1116 (or heating element 202 on eye-shield 200 of FIG. 7), quickly raises the temperature of the eye-shield, dissipating fog and condensation rapidly. In accordance with one embodiment of this aspect of the present invention, the max power level comprises a maximum power level. Providing maximum power to the heater on the eye-shield accelerates heating of the eye-shield, and thus the rate at which fog and condensation dissipates.

After the heater is turned on to a max power level 1906 using PWM, there begins a duration timer 1911 for the max power level. During the duration timer for the max power level 1911, the max power level is supplied to the heater that is available from the power source 1102 (FIG. 11). Sustaining this max power level assists in dissipating fog and condensation rapidly and fully from an eye-shield 1116. Powering the heater 1118, 1120, 1122 at max power level continues until a first duration of time 1911 (Delay1) is complete as shown at decision diamond 1916.

Once enough time lapses such that the first duration of time is complete at 1916, the power supplied then automatically lessens under program control by the microcontroller 1128 to the heater, and is reduced by way of PWM on-cycle level decrease to, for example, any level between 10% on-cycle to 70% on-cycle, but preferably around 50% on-cycle, for entry into an intermediate maintenance mode heating power level at 1921, at any level between the off power level and the max power level. The intermediate power level 1921 continues the process of dissipating any remaining fog or condensation on the eye-shield 1116 and additionally assists in preventing re-formation of fog and condensation on the eye-shield.

After the intermediate maintenance heating mode power level is turned on at 1921, there begins a duration timer at 1926 for the intermediate maintenance heating power level. During the duration timer at 1926 for the intermediate maintenance heating power level, the intermediate power level is supplied to the heater from the power source. Sustaining the intermediate power level continues to prevent future fogging of the eye-shield, and additionally, preserves battery life, since this is an automatically supplied lower, or reduced, power level than would be the case if the user were simply trying to manually manage the defogging of the eye-shield and had forgotten, for example, to turn the system off.

Powering the heater at the intermediate power level 1921 continues until a duration of time 1926 (Delay2) is complete as shown at decision diamond 1931. Once this duration of time 1926 is complete at 1931, the heater returns to the active mode state 1936, where the preliminary intermediate power level is supplied to the heater from the power supply using PWM regulation until either the battery becomes substantially fully depleted or the user turns the active mode of the system off. The heater will remain in the active mode position as indicated at 1941 until the user pushes the button as shown at decision diamond 1901 to begin the power-saving method again.

Alternatively, the method and system duration timer 1931 for the intermediate maintenance heating power level 1926 may be provided as indefinite, or infinite, such that the system stays at the intermediate power level indefinitely until either the battery becomes substantially fully depleted or the user reactivates the max power level at 1902, 1906. In either situation, the heater will remain in active-on position in accordance with this aspect of the invention shown in FIG. 19*b* until the user activates the max power level of the power-saving method again.

Entry into the on-demand mode may be determined by a short button press, whereas entry into the active-on mode may be determined by a longer button press. Further, a user may enter either the on-demand mode, or alternatively the active-on mode, from an off power position as determined by the length of the button press encountered.

Figure 20A:
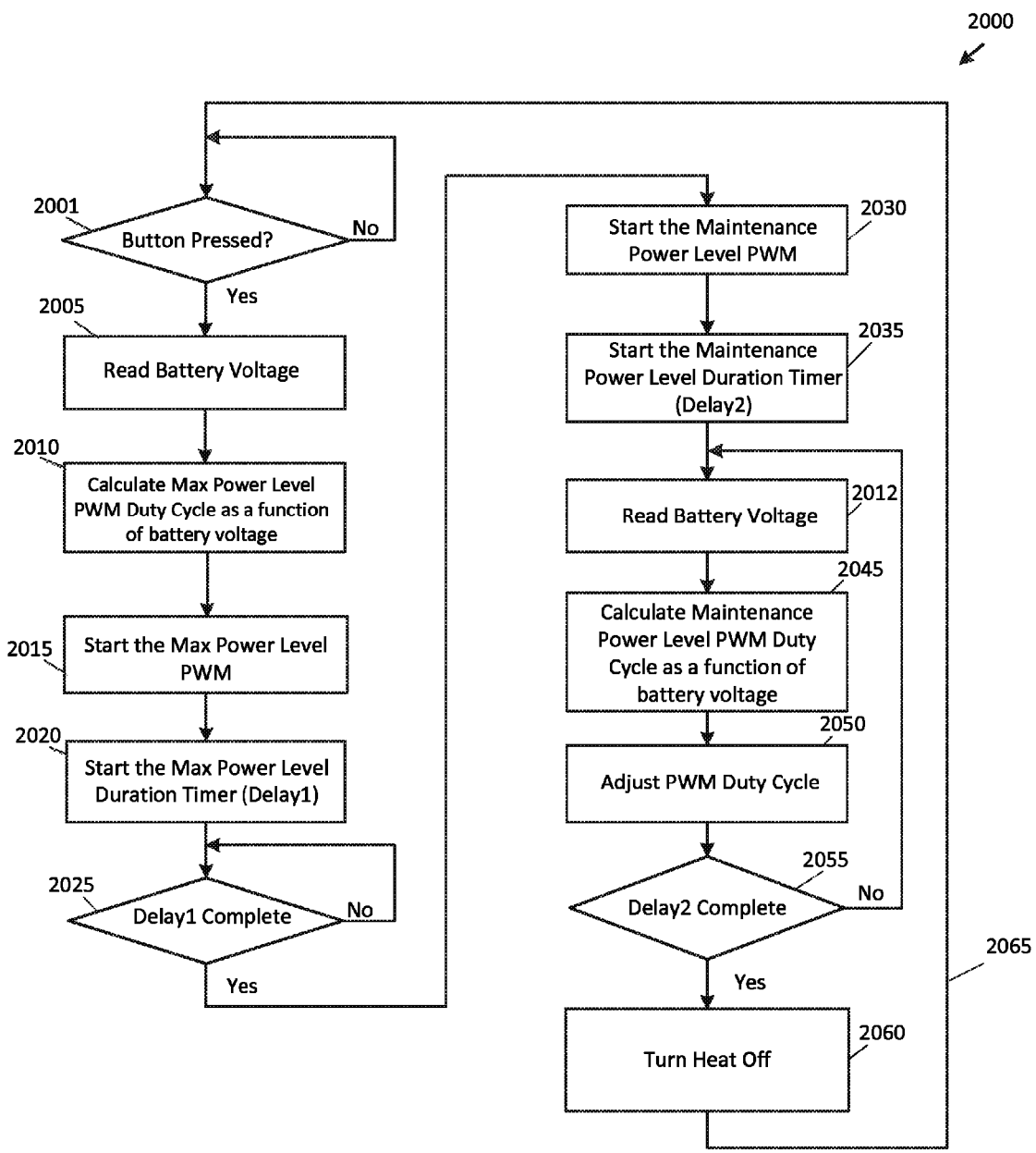
FIG. 20a is a flow diagram illustrating steps of a power-saving method and system in accordance with yet another embodiment of the aspect of the invention shown in FIG. 18a and including use of a pulse-width modulator and a battery compensation system.

Referring now to FIG. 20*a*, there is provided a flow diagram illustrating another alternate embodiment of a first aspect of the method and system 2000 of the invention, referred to as an on-demand mode of the system using PWM and a Battery Compensation System (BCS) as described herein. As shown in FIG. 20*a*, generally the on-demand mode method and system 2000 comprises the additional steps of reading the battery voltage 2005, 2012, calculating a max power level 2010, and calculating an intermediate maintenance power level 2045, both preferably using a PWM duty cycle chosen as a function of battery voltage per the BCS to compensate for battery depletion or loss prior to activating the heater.

Thus, upon detecting a button press at 2001, the system reads the battery voltage 2005 and calculates the desired max power level at 2010 using a PWM on-cycle level set as a function of the battery voltage determined to one of a substantially higher, substantially highest, or maximum, BCS compensated power level (hereafter "max power level"), or maximum heat/power mode using PWM at 2015. This is preferably done by an electronic system on board the eye-shield frame, e.g., system 1300 shown in FIG. 13 or system 1600 shown in FIG. 16, detecting whether a button is pressed at decision diamond 2001 by the user. If the button is not pressed at decision diamond 2001, the heater will remain in the off position until it is detected that the button is pressed. The program for controlling the application of the method of this aspect of the invention is accomplished, for example, with an MPU 1330 (FIG. 13) or microcontroller 1628 (FIG. 16). Turning or setting the power on to a max power level 2015, and supplying a max power level to a heating element, e.g., 1618, 1620, 1622 on an eye-shield 1616 (or alternatively heater 202 of eye-shield 200 of FIG. 6 or 7, or alternatively load 1345 of FIG. 13), quickly raises the temperature of the eye-shield and rapidly dissipates fog and condensation with a burst of power. In accordance with one embodiment of this aspect of the present invention, the max power level comprises a maximum power level. Providing maximum power to the heater on the eye-shield accelerates heating of the eye-shield, and thus the rate at which fog and condensation dissipates.

After the heater is turned on to the max power level 2015 using a BCS compensated PWM signal, there begins a duration timer 2020 for the max power level. During the duration timer for the max power level 2020, a BCS-compensated max power level using PWM is supplied to the heater that is available from the power source (e.g., Battery 1602 (FIG. 16)). Sustaining the max power level assists in dissipating fog and condensation rapidly and fully from the eye-shield 1616. Powering the heater (e.g., heaters 1618, 1620, 1622) at max power level continues until a first duration of time (Delay1) is complete as shown at decision diamond 2025.

Once enough time lapses such that the first duration of time is complete at 2025, the power supplied then automatically lessens to the heater under program control by the MPU 1330 or microcontroller 1628, by reducing the percentage of on-cycle PWM applied to an intermediate percentage level such as for example somewhere between 10% and 70% on-cycle PWM, and power is turned on to an intermediate maintenance mode heating power level at 2030 using PWM as a function of battery voltage per the BCS. The range of desirable intermediate power levels applied during this maintenance mode 2031 is any level between the off power level and the max power level, but preferably comprises a range of 40%-50% PWM on-cycle power level. The intermediate maintenance power level 2030 continues the process of dissipating any remaining fog or condensation on the eye-shield 1616 and additionally assists in preventing re-formation of fog and condensation on the eye-shield.

Powering the heater at the intermediate power level using PWM at 2030 in the maintenance mode continues until a duration of time (Delay2) 2035 is complete as shown at decision diamond 2055. During the maintenance mode wherein the intermediate power level is determined using a BCS compensated PWM on-cycle at 2030, a maintenance mode timer (Delay2) is begun at 2035. The maintenance mode further comprises the steps of reading battery voltage 2012, calculating an intermediate maintenance power level using a PWM on-cycle level compensated for voltage drop by the BCS at 2045, and automatically adjusting the required PWM duty cycle, until the maintenance mode timer (Delay2) is complete. Once this duration of time 2035 is complete 2055, the heater returns to the off position 2060, where no power is supplied to the heater from the power supply. It will be appreciated that power to the electronic system may preferably never be completely turned off, but rather would be reduced to an insignificant power level that would substantially maintain system memory intact while the system essentially idles while waiting for a button press at 2001. The heater will remain in the off position as indicated at 2065 until the user pushes the button 2001 to begin the power-saving method again. Each successive activation of the max power level in accordance with this aspect of the invention preferably restarts the max power level duration timer 2020, after which the maintenance level duration timer 2035 runs its course, in effect resetting the amount of time that the system will remain in this mode, which may be referred to as an on-demand mode.

Figure 20B:
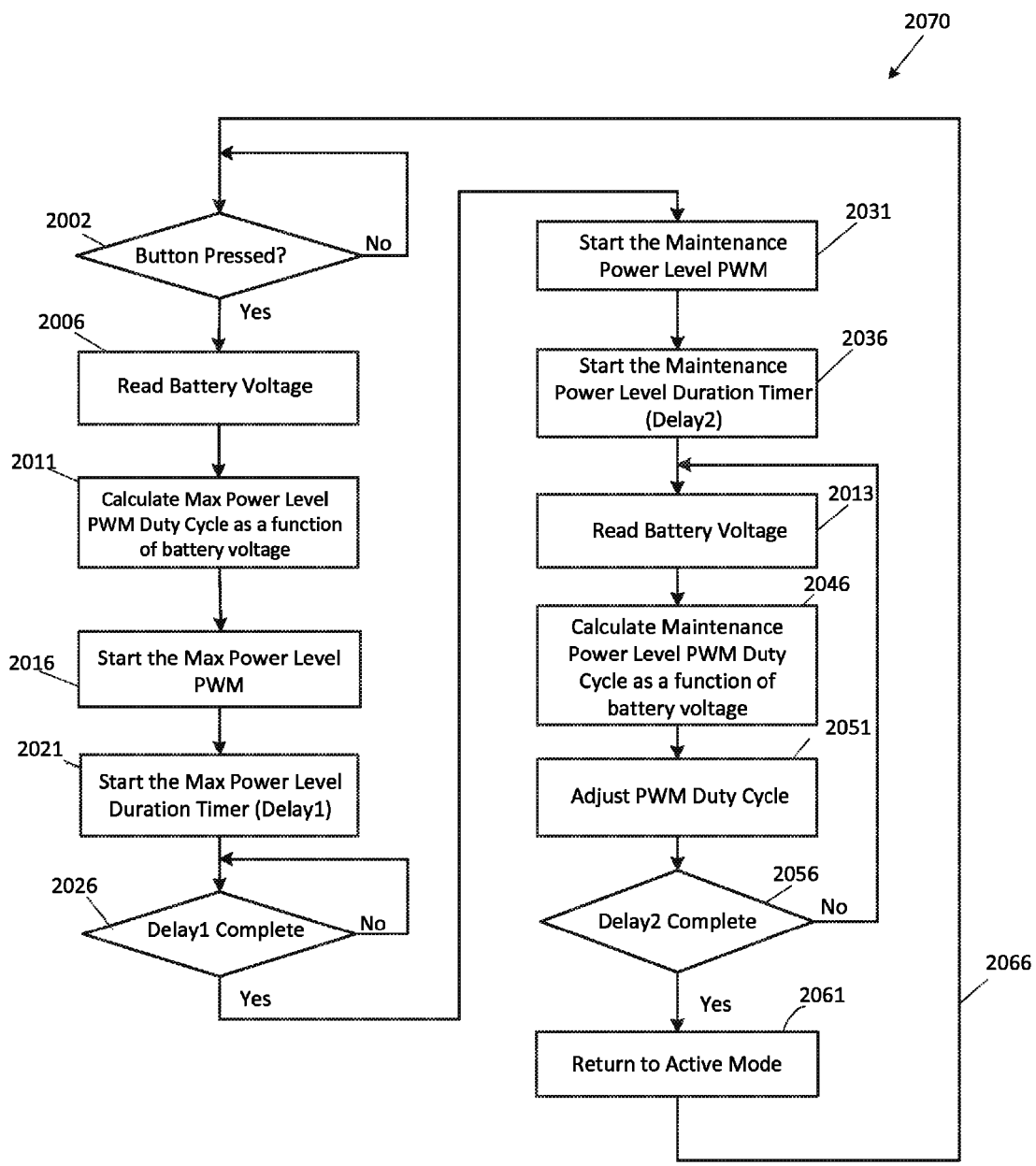
FIG. 20b is a flow diagram illustrating steps of a power-saving method and system in accordance with yet another embodiment of the aspect of the invention shown in FIG. 18b and including use of a pulse-width modulator and a battery compensation system.

Referring now to FIG. 20b, there is provided a flow diagram illustrating another alternate embodiment of a second aspect of the method and system 2000 of the invention, referred to as an active-on, or continuous power, mode of the system using PWM and a Battery Compensation System (BCS) as described herein. As shown in FIG. 20b, generally the active-on mode method and system 2070 comprises the additional steps of reading the battery voltage 2006, 2013, calculating a max power level 2011, and calculating an intermediate maintenance power level 2046, both preferably using a PWM duty cycle chosen as a function of battery voltage per the BCS to compensate for battery depletion or loss prior to activating the heater.

Thus, upon detecting a button press at 2002, the system reads the battery voltage 2006 and calculates the desired max power level at 2011 using a PWM on-cycle level set as a function of the battery voltage determined to one of a substantially higher, substantially highest, or maximum, BCS compensated power level (hereafter "max power level"), or maximum heat/power mode using PWM at 2016. This is preferably done by an electronic system on board the eye-shield frame, e.g., system 1300 shown in FIG. 13 or system 1600 shown in FIG. 16, detecting whether a button is pressed at decision diamond 2002 by the user. If the button is not pressed at decision diamond 2002, the heater will remain in active-on mode position where an intermediate level of power (e.g., any power level between 10% and 30%) which is continuously applied using a pre-determined desired PWM on-cycle level as described herein and adjusted by the BCS 1300, 1400 for battery depletion as described herein, until it is detected that the button is pressed. The program for controlling the application of the method of this aspect of the invention is accomplished, for example, with an MPU 1330 (FIG. 13) or microcontroller 1628 (FIG. 16). Turning or setting the power on to a max power level 2016, and supplying a max power level to a heating element, e.g., 1618, 1620, 1622 on an eye-shield 1616 (or alternatively heater 202 of eye-shield 200 of FIG. 6 or 7, or alternatively load 1345 of FIG. 13), quickly raises the temperature of the eye-shield and rapidly dissipates fog and condensation with a burst of power. In accordance with one embodiment of this aspect of the present invention, the max power level comprises a maximum power level. Providing maximum power to the heater on the eye-shield accelerates heating of the eye-shield, and thus the rate at which fog and condensation dissipates.

After the heater is turned on to the max power level using a BCS compensated PWM signal at 2016, there begins a duration timer (Delay1) at 2021 for the max power level. During the duration timer for the max power level 2021, the BCS-compensated max power level using PWM is supplied to the heater that is available from the power source (e.g., Battery 1602 of FIG. 16). Sustaining the max power level assists in dissipating fog and condensation rapidly and fully from the eye-shield 1616. Powering the heater (e.g., heaters

1618, 1620, 1622) at max power level continues until the first duration of time (Delay1) is complete as shown at decision diamond 2026.

Once enough time lapses such that the first duration of time is complete at 2026, the power supplied then automatically lessens to the heater under program control by the MPU 1330 or microcontroller 1628, by reducing the percentage of on-cycle PWM applied to an intermediate percentage level such as for example somewhere between 10% and 70% on-cycle PWM, and power is turned on to an intermediate heating power level at 2031 using PWM in an intermediate maintenance mode as a function of battery voltage per the BCS. The range of desirable intermediate power levels applied during this maintenance mode starting at 2031 is any level between the off power level and the max power level, but preferably comprises a range of 40%-50% PWM on-cycle power level adjusted per the BCS. The intermediate maintenance power level 2031 continues the process of dissipating any remaining fog or condensation on the eye-shield 1616 and additionally assists in preventing re-formation of fog and condensation on the eye-shield.

Powering the heater at the intermediate power level using PWM at 2031 in the intermediate maintenance mode continues until a duration of time (Delay2) 2036 is complete as shown at decision diamond 2056. During the maintenance mode wherein the intermediate power level is determined using a BCS compensated PWM on-cycle beginning at 2031, an intermediate maintenance mode timer (Delay2) is begun at 2036. The intermediate maintenance mode further comprises the steps of reading battery voltage 2013, calculating an intermediate maintenance power level using a PWM on-cycle level compensated for voltage drop by the BCS at 2046, and automatically adjusting the required PWM duty cycle with the BCS, for example by using a table as shown in FIG. 15 or 17 per BCS 1300, 1400, until the intermediate maintenance mode timer (Delay2) is complete. Once this duration of time 2036 is complete 2056, the heater returns to the active-on mode 2061, where power is supplied to the heater from the power supply preferably at the preliminary intermediate power level, or some other desired power level, until the button is pressed again at 2002, the battery runs out of power, or the user turns off the system or enters an on-demand mode as described previously. Thus, the heater will remain in the off position as indicated at 2066 until the user pushes the button 2001 to begin the power-saving method again.

Each successive activation of the max power level in accordance with this aspect of the invention preferably restarts the max power level duration timer 2021, after which the maintenance level duration timer 2036 runs its course, in effect resetting the amount of time that the system will remain in this mode, which may be referred to as an active-on mode.

Entry into the on-demand mode may be determined by a short button press, whereas entry into the active-on mode may be determined by a longer button press. Further, a user may enter either the on-demand mode, or alternatively the active-on mode, from an off power position as determined, for example, by the length of the button press encountered.

Application of Battery Compensation to the on-Demand and Active-on Modes

As described previously in connection with the Battery Compensation System, a system 1300 (of FIG. 13) and 1400 (of FIG. 14), or alternatively 1600 (of FIG. 16), using pulse-width-modulation (PWM) (contained in the MPU 1330, or alternatively contained in microcontroller 1628), preferably comprises a voltage divider circuit 1610 for proportionally adjusting the voltage to a measurable range, and an analog to digital converter (ADC) 1605 preferably contained in the MPU or microcontroller for receiving the output from the voltage divider and converting it into a digital voltage value. Preferably, the voltage divider circuit 1610 comprises two precision resistors in series (as described above in connection with FIG. 13) between positive and negative terminals of a battery or batteries 1602 for proportionally adjusting the voltage to a measurable range, the voltage divider circuit preferably having a tap between the two resistors adapted to provide the proportional voltage measurement to an I/O pin on MPU 1330, or microcontroller 1628 containing the analog-to-digital converter 1605.

The desired power levels of this aspect of the invention are preferably pre-determined and implemented automatically by program control using BCS and tables, as shown and described previously in connection with FIGS. 15 and 17, or via calculation as previously described. However, it will be appreciated that the desired power levels of this aspect of the invention may be otherwise determined in accordance with an automated system comprising a Dew Point Calculator 802/802' as described previously in connection with FIGS. 8 and 10 above as well, and which desired power levels may be implemented by varying the PWM on-cycle levels via program control by MPU 1330, or microprocessor 1628, driving load drivers 1636, all as described hereinabove. A visual feedback system may be optionally implemented in accordance with this aspect of the invention as described previously, or not, since control of the system is preferably at least partially automated.

In response to changes from the power level control (e.g., 1606 of FIG. 16), and/or at regular intervals as for example at the end of the max power level timer or the intermediate maintenance power level timer as described herein, the MPU 1330, or alternatively microcontroller 1628, uses the voltage level determined by reading the battery voltage at 2005 and 2012 for the on-demand mode method and system 2000, and at 2006 and 2013 for the active-on mode method and system 2070, and as described previously, to choose from a conversion table, such as table 1500 or table 1700, an appropriate PWM cycle level required to compensate for battery depletion as measured by the determined voltage of the battery. Reading battery voltage and determining/adjusting the PWM duty cycle as a function of the battery voltage allows for an optimal desired power to be supplied to the heater, depending upon the system mode involved, from the battery based on available battery power. In this way, power to the eye-shield system is enabled to remain consistent over time in use, from time-to-time and during a single use cycle, despite battery depletion over time.

For purposes of this embodiment of the method and system 2000 of the invention, the data lookup table 1500 shown in FIG. 15 may be used to compensate for battery voltage depletion over time in use in order to select an appropriate PWM duty cycle to be applied to achieve a desired power/heater level setting depending upon which mode, max power level mode or intermediate power level maintenance mode, is involved. The desired power level settings are shown in Watts across the top of the table 1500, and actual heater power for a given battery voltage ranging from 8.4 Volts DC (assuming two lithium-ion batteries of 3.7 Volts DC each in series) depleted down to 6.8 Volts DC (shown in the left-hand column of the table 1500). Thus, for example, when the battery 1305 is at full power (that is there has been no depletion of battery charge yet), and 2 Watts of total power is desired, 11.3 on cycles (out of 100.0 total cycles) will need to be on. As can be seen from the FIG. 15, the number of duty cycles increases as shown as a greater number of Watts is desired or needed by the system by predetermined power levels, and a larger number of duty cycles is required to compensate for increasingly depleted charge in the battery. Thus for example, 86.5 duty cycles (that is PWW will switch the power on 86.5 cycles for every 100 cycles—or in other words the PWM controls transmission of power to allow power to the load 86.5 cycles out of a hundred, or 86.5 on and 13.5 off) is required to produce 10 watts of power where the battery has depleted as indicated by a voltage reading of 6.8V from an 8.4 volt battery. Thus, as can be seen in the table, the number of duty cycles required increases as the battery depletes further and the higher the power level that is required by the system (e.g., at max power levels or at intermediate power levels of the system as described herein). While the example data table 1500 is based upon a system using two lithium-ion batteries of 3.7 Volts DC each in series, the invention is not limited to a two-battery, or otherwise plural-battery, system, and the battery compensation system of the invention may be used with a single battery with an appropriately adjusted data table, or calculations as the case may be. Further, while the number of duty cycles is represented as an integer with a decimal portion, these numbers may be rounded to the nearest integer in an actual PWM implementation.

Power Supplied Over Time Charts

Figure 21A:
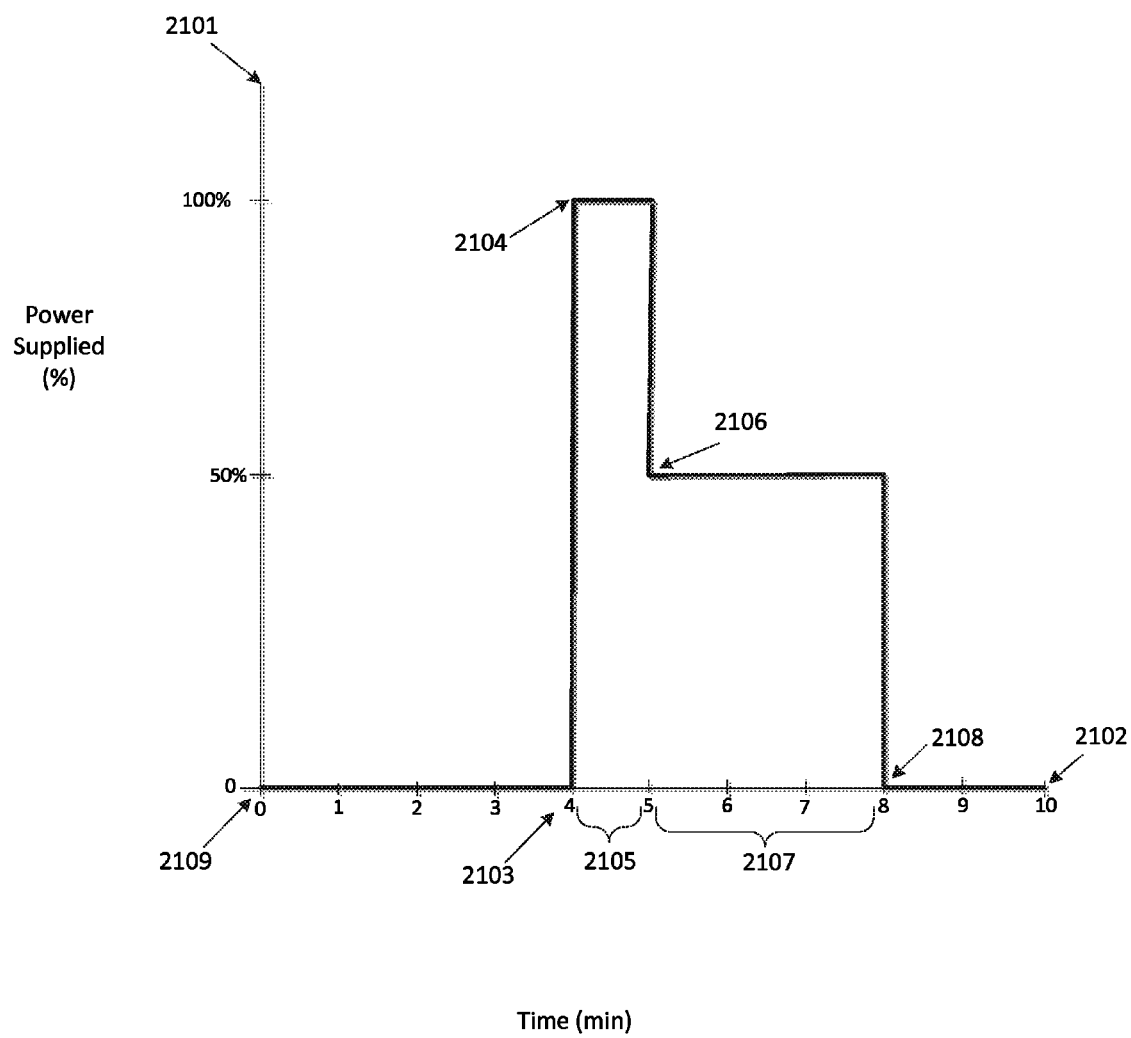

Referring to FIG. 21*a*, there is shown a graphical representation of one example of an on-demand battery power-saving method showing percentage of power supplied to a heater, with power supplied on one axis 2101 and time on the other axis 2102. In this representation, a power off power level is in effect for four minutes, as shown at 2109, thus conserving the battery of the system. At a time of four minutes at 2103 on the chart, a button is pressed, the method begins, and the heater in this example is turned on to a max power level 2104 (in this example the max power level 2104 is at 100% power level as, for example, determined by a 100% PWM signal). Of course it will be appreciated that a max power level of 90%, 80%, or some other substantially higher setting than an intermediate power level, would not depart from the true scope and spirit of the invention. After the heater is turned on to a max power level 2104, there begins a duration timer (Delay1) for the max power level that, in this example, lasts for one minute 2105. During the duration timer for the max power level 2104, the max power is supplied to the heater that is available from the power source.

Powering the heater at the max power level 2104 continues until a first duration of time 2105 (Delay1) is complete, at which point the power supplied lessens, and an intermediate, maintenance heating power level 2106 is turned on, which is a level between the off power level 2108 and the max power level 2104. After the intermediate, maintenance heating power level 2106 is set or turned on, there begins a duration timer 2107 (Delay2) for the intermediate, maintenance heating power level that, in this example, lasts for three minutes. During the duration timer 2107 for the intermediate maintenance mode, an intermediate power level 2106 is supplied to the heater from the power source.

Once this duration of time 2107 (Delay2) is complete, the heater returns to the off position as at 2108, where no power is supplied to the heater from the power supply. The heater will remain in the off position 2108 until the user pushes the button to re-start this or another power-saving method 1800, 1850, or alternatively in the PWM embodiment of the method and system 1900, 1950, or alternatively in the BCS compensated PWM embodiment of the method and system 2000, 2070.

Figure 21B:
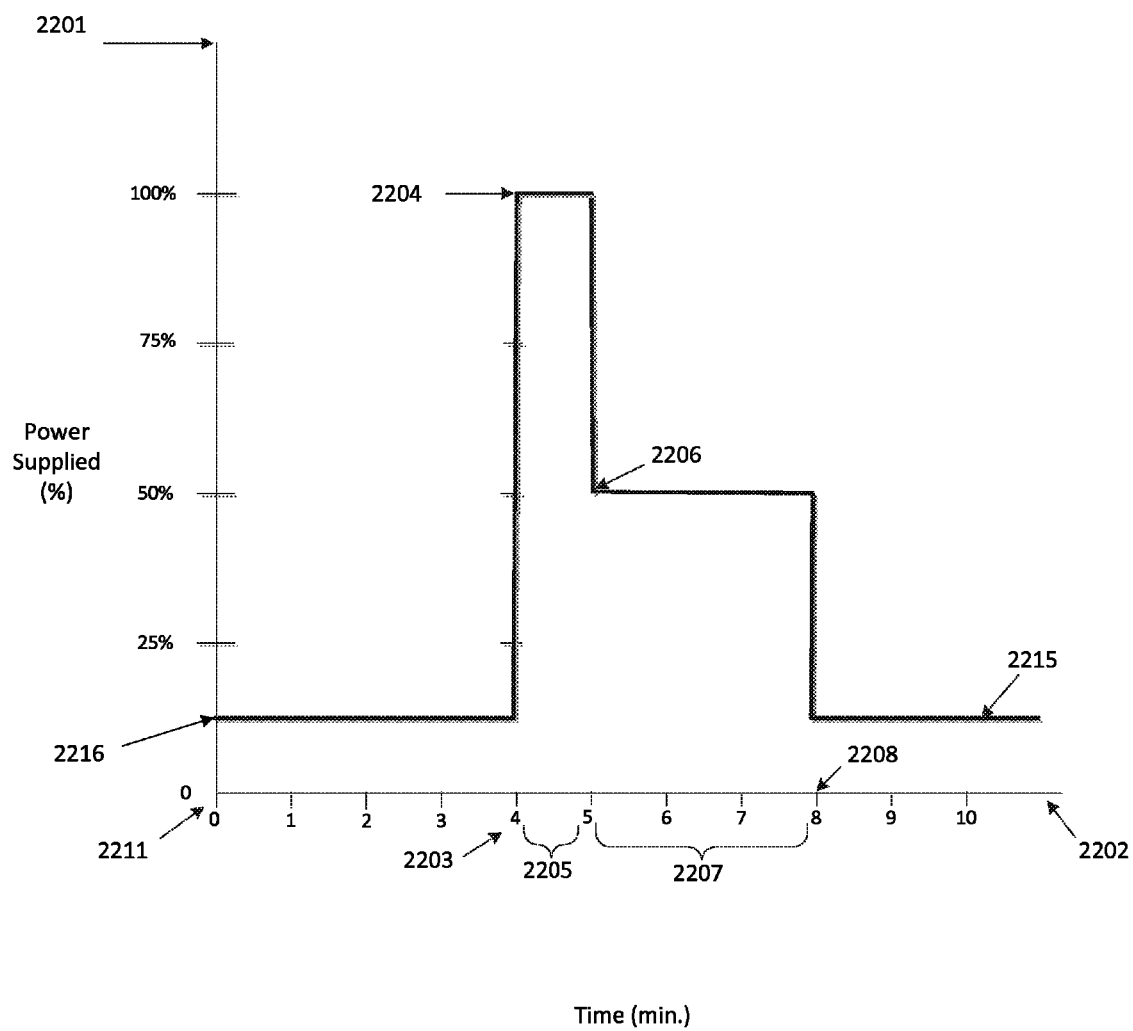
FIG. 21b is a graphical representation of another example of power supplied over time of a battery power-saving method and system in accordance with the aspect of the invention shown in FIG. 18b.

Referring now to FIG. 21*b*, there is shown a graphical representation of another example of a battery power-saving method showing percentage of power supplied to a heater, with power supplied on one axis 2201 and time on the other axis 2202. In this representation, at a time of zero minutes at 2211, the power is shown as being already on in a preliminary intermediate power level 2216, as in the case of an active-on embodiment of the invention before an additional button press. As shown in FIG. 21*b*, the system essentially idles for four minutes in this example at, for example, a 12% preliminary intermediate power level 2216 until a button is pressed at 2203 to enter into a power burst mode as shown at 1850, 1950, 2070 where the heater is set to a max power level 2204 (in this example at approximately 100% PWM). After the heater is turned on to a max power level 2204, there begins a duration timer for the max power level that, in this example, lasts for one minute 2205. During the duration timer 2205 for the max power level 2204, the max power level is supplied to the heater that is available from the power source. Thus, in the PWM embodiment of this aspect of the invention, the power level setting preferably will be determined by a microprocessor (e.g., MPU 1330 or microcontroller 1628) which determines the PWM on-cycle setting for application to the load (e.g., heater load 1345 or heaters 1618, 1620, 1622), whereas in the PWM and BCS embodiment, the power level preferably will be determined by the microprocessor which determines the PWM on-cycle setting determined as a function of the BCS as described previously and accordingly applies the power to the load.

Powering the heater at the max power level 2204 continues until a first duration of time 2205 (Delay1) is complete, at which point the power supplied is reduced, or lessens, and an intermediate, maintenance heating power level 2206 is turned on, which is a level between the preliminary intermediate maintenance power level 2216 and the max power level 2204. After the intermediate, maintenance heating power level 2206 is turned on, there begins a duration timer 2207 for the intermediate maintenance mode that, in this example, lasts for three minutes. During the duration of timer 2207 for the intermediate maintenance mode, the intermediate power level 2206 is supplied to the heater from the power source.

Once this duration of time 2207 (Delay2) is complete at 2208, the heater returns to the preliminary intermediate power level 2206, where that level of intermediate power, or another lesser or higher level of intermediate power, is supplied to the heater from the power supply during the active-on, or continuous-on, mode 2215 until either the battery becomes substantially fully depleted, the user turns the power off, or the user enters an on-demand mode. The user may activate a power burst at any time during the active-on mode by, for example, making a quick button press to indicate a desire for a quick burst of power to clear any fog that may be encountered. The heater remains in the most recent active-on position 2206 until the user pushes the button to re-start this or another power-saving method 1800, 1850, or alternatively in the PWM embodiment of the method and system 1900, 1950, or alternatively in the BCS compensated PWM embodiment of the method and system 2000, 2070.

While a preferred embodiment of the present invention has been shown and described, it will be apparent to those skilled in the art that many changes and modifications may be made without departing from the invention in its broader aspects. For example, it will be appreciated that one of ordinary skill in the art may mix and match the various components of the various aspects and embodiments of the invention without departing from the true spirit of the invention as claimed. The appended claims are therefore intended to cover all such changes and modifications as fall within the true spirit and scope of the invention.

The invention claimed is:

1. A power-saving method for efficiently heating an eye-shield apparatus adapted for use with a thin-film heater powered by a power source to prevent fogging of the eye-shield comprising the steps of:
   activating the heater from an off power level to a max power level on the eye-shield apparatus;
   continuing heating at the max power level for a first duration of time;
   lessening power supplied to the heater after the first duration of time to an intermediate power level between the off power level and the max power level;
   continuing heating at the intermediate power level for a second duration of time; and
   setting the power to the off power level after the second duration of time.

2. The power-saving method for efficiently heating an eye-shield apparatus of claim 1, wherein the max power level comprises a maximum power level.

3. The power-saving method for efficiently heating an eye-shield apparatus of claim 1, wherein said eye-shield apparatus further comprises a PWM system for regulating power from the power source to the heater and further comprising applying a desired pulse-width modulator duty cycle for at least one of the max power level, the intermediate power level and the off power level.

4. The power-saving method for efficiently heating an eye-shield apparatus of claim 3, wherein the eye-shield apparatus further comprises a battery compensation system, the power-saving method further comprising the steps of providing consistent power to the heater despite battery voltage drop resulting from battery depletion through use of a battery compensation system.

5. The power-saving method for efficiently heating an eye-shield apparatus of claim 4, wherein the battery compensation system further comprises a voltage divider, an analog to digital converter, and a processor, the power-saving method further comprising the steps of:
   proportionally adjusting the voltage to a measurable range using the voltage divider;
   receiving an analog voltage signal from the voltage divider and converting the analog voltage output into a digital voltage signal; and
   determining a compensating duty cycle to apply power to the heater using the digital voltage signal.

6. A power-saving method for efficiently heating an eye-shield apparatus adapted for use with a powered thin-film heater to prevent fogging of the eye-shield comprising the steps of:
   activating the heater to a max power level from a desired preliminary intermediate power level between a power off level and the max power level on the eye-shield apparatus;
   continuing heating at the max power level for a first duration of time;
   lessening power supplied to the eye-shield apparatus after the first duration of time to any power level intermediate between the off power level and the max power level;
   continuing heating at the any power level intermediate between the off power level and the max power level until either a user turns off the eye-shield apparatus or battery power is substantially fully depleted and the eye-shield apparatus shuts off.

7. The power-saving method for efficiently heating an eye-shield apparatus of claim 6, wherein the max power level comprises a maximum power level.

8. The power-saving method for efficiently heating an eye-shield apparatus of claim 6, wherein the eye-shield apparatus further comprises a PWM system for regulating power from the power source to the heater and further comprising the steps of:
   applying a desired pulse-width modulator duty cycle for at least one of the max power level, the preliminary intermediate power level, the any power level intermediate between the off power level and the max power level, and the off power level, from a pulse-width modulator system for controlling the amount of heat applied to the eye-shield apparatus.

9. The power-saving method for efficiently heating an eye-shield apparatus of claim 8, wherein the eye-shield apparatus further comprises a battery compensation system, the power-saving method further comprising the steps of providing consistent power to the heater despite battery voltage drop resulting from battery depletion through use of a battery compensation system.

10. The power-saving method for efficiently heating an eye-shield apparatus of claim 9, wherein the battery compensation system further comprises a voltage divider, an analog to digital converter, and a processor, the power-saving method further comprising the steps of:
    proportionally adjusting the voltage to a measurable range using the voltage divider;
    receiving an analog voltage signal from the voltage divider and converting the analog voltage output into a digital voltage signal; and
    determining a compensating duty cycle to apply power to the heater using the digital voltage signal.

11. A power-saving method for efficiently heating an eye-shield apparatus adapted for use with a powered thin-film heater to prevent fogging of the eye-shield comprising the steps of:
    activating the heater to a max power level from a power off level;
    continuing heating at the max power level for a first duration of time;
    lessening power supplied to the eye-shield apparatus after the first duration of time to an intermediate power level between the off power level and the max power level;
    continuing heating at the intermediate power level until either a user turns off the eye-shield apparatus or battery power is substantially fully consumed and the eye-shield apparatus shuts off.

12. The power-saving method for efficiently heating an eye-shield apparatus of claim 11, wherein the max power level comprises a maximum power level.

13. The power-saving method for efficiently heating an eye-shield apparatus of claim 11, wherein the eye-shield apparatus further comprises a PWM system for regulating power from the power source to the heater and further comprising the steps of:
    applying a desired pulse-width modulator duty cycle for at least one of the max power level, the intermediate power level, and the off power level, from a pulse-width modulator system for controlling the amount of heat applied to the eye-shield apparatus.

14. The power-saving method for efficiently heating an eye-shield of claim 13, wherein the eye-shield apparatus further comprises a battery compensation system, the power-saving method further comprising the steps of providing consistent power to the heater despite battery voltage drop resulting from battery depletion through use of a battery compensation system.

15. The power-saving method for efficiently heating an eye-shield apparatus of claim 14, wherein the battery compensation system further comprises a voltage divider, an analog to digital converter, and a processor, the power-saving method further comprising the steps of:
 proportionally adjusting the voltage to a measurable range using the voltage divider;
 receiving an analog voltage signal from the voltage divider and converting the analog voltage output into a digital voltage signal; and
 determining a compensating duty cycle to apply power to the heater using the digital voltage signal.

16. A power-saving method for efficiently heating an eye-shield apparatus adapted for use with a powered thin-film heater to prevent fogging of the eye-shield comprising the steps of:
 activating the heater to a max power level from a desired preliminary intermediate power level between a power off level and the max power level on the eye-shield apparatus;
 continuing heating at the max power level for a first duration of time;
 lessening power supplied to the eye-shield apparatus after the first duration of time to a secondary power level intermediate between the preliminary intermediate power level and the max power level;
 continuing heating at the secondary power level for a second duration of time;
 lessening power supplied to the eye-shield apparatus after the second duration of time to substantially the preliminary intermediate power level until either a user turns off the eye-shield apparatus or battery power is substantially fully consumed and the eye-shield apparatus shuts off.

17. The power-saving method for efficiently heating an eye-shield apparatus of claim 16, wherein the max power level comprises a maximum power level.

18. The power-saving method for efficiently heating an eye-shield apparatus of claim 16, wherein the eye-shield apparatus further comprises a PWM system for regulating power from the power source to the heater and further comprising the steps of:
 applying a desired pulse-width modulator duty cycle for at least one of the max power level, the preliminary intermediate power level, the secondary power level, and the off power level, from a pulse-width modulator system for controlling the amount of heat applied to the eye-shield apparatus.

19. The power-saving method for efficiently heating an eye-shield of claim 18, wherein the eye-shield apparatus further comprises a battery compensation system, the power-saving method further comprising the steps of providing consistent power to the heater despite battery voltage drop resulting from battery depletion through use of a battery compensation system.

20. The power-saving method for efficiently heating an eye-shield apparatus of claim 19, wherein the battery compensation system further comprises a voltage divider, an analog to digital converter, and a processor, the power-saving method further comprising the steps of:
 proportionally adjusting the voltage to a measurable range using the voltage divider;
 receiving an analog voltage signal from the voltage divider and converting the analog voltage output into a digital voltage signal; and
 determining a compensating duty cycle to apply power to the heater using the digital voltage signal.

* * * * *